US011898143B2

(12) United States Patent
Belayew et al.

(10) Patent No.: US 11,898,143 B2
(45) Date of Patent: Feb. 13, 2024

(54) AGENTS USEFUL IN TREATING FACIOSCAPULOHUMERAL MUSCULAR DYSTROPHY

(71) Applicant: Universite de Mons, Mons (BE)

(72) Inventors: Alexandra Belayew, Tilff (BE); Frederique Coppee, Havre (BE); Celine Vanderplanck, Asquillies (BE); Stephen Donald Wilton, Applecross (AU); Eugenie Ansseau, Dour (BE)

(73) Assignee: Universite de Mons, Mons (BE)

( * ) Notice: Subject to any disclaimer, the term of this patent is extended or adjusted under 35 U.S.C. 154(b) by 338 days.

(21) Appl. No.: 17/153,215

(22) Filed: Jan. 20, 2021

(65) Prior Publication Data
US 2021/0163942 A1    Jun. 3, 2021

Related U.S. Application Data

(60) Continuation of application No. 16/562,030, filed on Sep. 5, 2019, now Pat. No. 10,907,157, which is a continuation of application No. 15/873,751, filed on Jan. 17, 2018, now abandoned, which is a continuation of application No. 15/047,258, filed on Feb. 18, 2016, now Pat. No. 9,988,628, which is a continuation of application No. 14/078,133, filed on Nov. 12, 2013, now abandoned, and a division of application No. 13/225,384, filed on Sep. 2, 2011, now abandoned.

(30) Foreign Application Priority Data

Sep. 2, 2010  (EP) .................................... 10175125

(51) Int. Cl.
C12N 15/11       (2006.01)
C12N 15/113      (2010.01)

(52) U.S. Cl.
CPC .......... *C12N 15/113* (2013.01); *C12N 15/111* (2013.01); *C12N 2310/11* (2013.01); *C12N 2310/14* (2013.01); *C12N 2310/315* (2013.01); *C12N 2310/321* (2013.01); *C12N 2310/3233* (2013.01); *C12N 2310/3513* (2013.01); *C12N 2310/531* (2013.01); *C12N 2320/33* (2013.01)

(58) Field of Classification Search
CPC .............. C12N 15/113; C12N 2310/11; C12N 2320/33; C12N 15/111
See application file for complete search history.

(56) References Cited

U.S. PATENT DOCUMENTS

| 6,136,603 | A  | 10/2000 | Dean |
| 7,250,496 | B2 | 7/2007  | Bentwich |
| 7,655,785 | B1 | 2/2010  | Bentwich |
| 7,696,334 | B1 | 4/2010  | Bentwich |
| 2005/0255487 | A1 | 11/2005 | Khvorova et al. |
| 2007/0050146 | A1 | 3/2007 | Bentwich et al. |
| 2007/0105805 | A1 | 5/2007 | Kmiec et al. |
| 2008/0199960 | A1 | 8/2008 | Juliano et al. |
| 2009/0156533 | A1 | 6/2009 | McSwiggen et al. |
| 2009/0281164 | A1 | 11/2009 | McSwiggen et al. |
| 2012/0225034 | A1 | 9/2012 | Belayew |
| 2013/0288976 | A1 | 10/2013 | van der Maarel et al. |
| 2014/0105873 | A1 | 4/2014 | Belayew |

FOREIGN PATENT DOCUMENTS

| JP | 2006-129807   | 5/2006  |
| WO | WO 2009/124341 | 10/2009 |
| WO | WO 2012/024535 | 5/2012  |
| WO | WO 2013/016352 | 1/2013  |

OTHER PUBLICATIONS

Ansseau et al., "DUX4c is Up-regulated in FSHD. It Induces the MYF5 protein and Human Myoblast Proliferation," PLOS One, vol. 4(10), p. e7482 (11 pages), (Oct. 2009).
Arnett et al., "Therapy for Neuromuscular Disorders," Current Opinion in Genetics & Development, vol. 19(3), pp. 290-297, (Jun. 2009).
Bennett et al. "RNA Targeting Therapeutics: Molecular Mechanisms of Antisense Oligonucleotides as a Therapeutic Platform". The Annual Review of Pharmacology and Toxicology, pp. 259-293, 2010.
Bortolanza et al. "AAV6-mediated Systemic shRNA Delivery Reverses Disease in a Mouse Model of Facioscapulohumeral Muscular Dystrophy". Molecular Therapy vol. 19, No. 11 pp. 2055-2064, Nov. 2011.
Bosnakovski et al., "An Isogenetic Myoblast Expression Screen Identifies DUX4-mediated FSHDassociated Molecular Pathologies," The EMBO Journal, vol. 27, pp. 2766-2779, (Oct. 2008).
Bosnakovski et al., "DUX4c, an FSHD Candidate Gene, Interferes with Myogenic Regulators and Abolishes Myoblast Differentiation," Experimental Neurology, vol. 214(1), pp. 87-96, (Nov. 2008).
Chamberlain et al. "Validity of RNAi-based therapeutics as a treatment for FSHD as demonstrated in a mouse model of muscular dystrophy", Mar. 2011.

(Continued)

*Primary Examiner* — Dana H Shin
(74) *Attorney, Agent, or Firm* — Knobbe, Martens, Olson & Bear, LLP

(57)    ABSTRACT

Antisense agents and RNA interference agents useful for treating diseases and conditions the treatment of which can benefit from reducing the expression of double homeobox 4 and/or double homeobox 4c, more particularly facioscapulohumeral muscular dystrophy. Methods, uses and further products employing such agents are also described.

30 Claims, 27 Drawing Sheets

Specification includes a Sequence Listing.

(56) References Cited

OTHER PUBLICATIONS

Ding et al., "Characterization of a double homeodomain protein (DUX!) encoded by a cDNA homologous to 3.3kb dispersed repeated elements," Human Molecular Genetics, vol. 7(11), pp. 1681-1694, (1998).

Dixit et al., "DUX4, a candidate gene of facioscapulohumeral muscular dystrophy, encodes a transcriptional activator ofPITXI," PNAS, vol. 104(46), pp. 18157-18162, (Nov. 2007).

Gabriels et al., "Nucleotide sequence of the partially deleted D4Z4 locus in a patient with FSHD identifies a putative gene within each 3.3 kb element," Gene, vol. 236(1), pp. 25-32, (1999).

Geng et al., "DUX4 activates germline genes, retroelements, and immune-mediators: Implications for facioscapulohumeral dystrophy," Dev Cell, vol. 22(1), pp. 38-51, (Jan. 2012).

Kowaljow et al., "The DUX4 gene at the FSHDIA locus encodes a pro-apoptotic protein," Neuromuscular Disorders, vol. 17, pp. 611-623, (2007).

Lam et al. "siRNA Versus miRNA as Therapeutics for Gene Silencing". Molecular Therapy—Nucleic Acids, Sep. 15, 2015.

Lemmers et al., "A Unifying Genetic Model for Facioscapulohumeral Muscular Dystrophy," Science, vol. 329, pp. 1650-1653, (Sep. 2010).

Lemmers et al., "Facioscapulohumeral muscular dystrophy is uniquely associated with one of the two variants of the 4q subtelomere," Nature Genetics, vol. 32(2), pp. 235-236, (2002).

M Van der Maarel et al. "Facioscapulohumeral Muscular Dystrophy and DUX4: Breaking the Silence". Trends in Mol Medicine pp. 252-258, May 2011.

Snider et al. "Facioscapulohumeral Dystrophy: Incomplete Suppression of a Retrotransposed Gene". PLOS Genetics, vol. 6 Issue 10, Oct. 2010.

Snider et al. "RNA transcripts, miRNA-sized fragments and proteins produced from D4Z4 units: new candidates for the pathophysiology of facioscapulohumeral dystrophy". Human Molecular Genetics vol. 18, No. 13, Apr. 9, 2009.

Snider et al. "Facioscapulohumeral Dystrophy: Incomplete Suppression of a Retrotransposed Gene," Plos Genetics, vol. 6(10), Pg. eIOOI 181 (14 pages), (Oct. 2010).

Snider et al., "RNA transcripts, miRNA-sized fragments and proteins produced from D4Z4 units: new candidates for the pathophysiology offacioscapulohumeral dystrophy," Human Molecular Genetics, vol. 18, pp. 2414-2430, (2009).

Snimer et al., "Supplementary Tables 1, 2, and 3," Human Molecular Genetics, vol. 18, 3 pages, (2009).

Tawil et al., "Facioscapulohumeral dystrophy: the path to consensus on pathophysiology," Skeletal Muscle, vol. 4(12), pp. 1-15, (2014).

Troilet et al., Gene Therapy for muscular dystrophy: current progress and future prospects, Expert Opinion on Biological Therapy, vol. 9, pp. 849-866 (2009).

Tupil et al., "Monosomy of distal 4q does not cause facioscapulohumeral muscular dystrophy," Journal of Medical Genetics, vol. 33, pp. 366-370, (1996).

USPTO; Final Office Action in U.S. Appl. No. 13/225,384 dated Jun. 11, 2013.

USPTO; Final Office Action in U.S. Appl. No. 14/078,133 dated Aug. 20, 2015.

USPTO; Non-Final Office Action in U.S. Appl. No. 13/225,384 dated Jan. 16, 2013.

USPTO; Non-Final Office Action in U.S. Appl. No. 14/078,133 dated Dec. 24, 2014.

USPTO; Requirement for Restriction in U.S. Appl. No. 14/078, 133 dated Aug. 15, 2014.

USTPO; Requirement for Restriction in U.S. Appl. No. 13/225,384 dated Oct. 11, 2012.

USPTO; Non-Final Office Action in U.S. Appl. No. 16/562,030 dated May 18, 2020.

USPTO; Notice of Allowance in U.S. Appl. No. 16/562,030 dated Dec. 28, 2020.

Van der Maarel et al., "Facioscapulohumeral muscular dystrophy and DUX4: breaking the silence," Trends in Molecular Medicine, vol. 17, pp. 252-258, (2011).

Van Geel et al., Genomic analysis of human chromosome 10q and 4q telomeres suggests a common origin, vol. 79, pp. 210-217 (2002).

Vanderplanck et al. "Seventh Australasian Gene Therapy Society Meeting". The Journal of Gene Medicine, May 2011.

Vanderplanck et al. "Suppression of DUX4 or DUX4c protein expression by antisense strategies in a Therapeutic approach for FSHD", Mar. 2011.

Vanderplanck et al., "The FSHD Atrophic Myotube Phenotype is Caused by DUX4 Expression," Plos ONE, vol. 6(10), p. e26820 (14 pages), (Oct. 2011).

Wallace et al. "Magic Factor-1, a Partial Agonist of Met, Induces Muscle Hypertrophy by Protecting Myogenic Progenitors from Apoptosis". Molecular Therapy vol. 17, Supplement 1, May 2009.

Wallace et al., "DUX4, a Candidate Gene for Facioscapulohumeral Muscular Dystrophy, Causes p53-Dependent Myopathy In Vivo," Ann. Neurol., vol. 69(3), pp. 540-552, (Mar. 2011).

Wallace et al., "RNA interference inhibits DUX4-induced muscle toxicity in vivo: Implications for a targeted FSHD therapy," Molecular Therapy, vol. 20, pp. 1417-1423, (2012).

Wallace et al., Developing RNAi therapy for FSHD, Molecular Therapy, vol. 17, supplement 1, S151, abstract No. 387 (2009).

Kim et al. "Strategies for silencing human disease using RNA interference" Nature Reviews Genetics, vol. 8, pp. 173-184, Mar. 2007.

Yao et al. "DUX4-induced gene expression is the major molecular signature in FSHD skeletal muscle" Human Molecular Genetics, vol. 20, No. 24, pp. 5242-5352, 2014.

FIGURE 3

```
12001 agaaacggag gccccggggg agctggaggc ctcggaagag gccgcctcgc tggaagcacc
12061 cctcagcgag gaagaatacc gggctctgct ggaggagctt tag gacgcgg ggttgggacg
12121 gggtcgggtg gttcggggca gggccgtggc ctctctttcg cggggaacac ctggctggct
12181 acggaggggc gtgtctccgc cccgccccct ccaccgggct gaccggcctg ggattcctgc
12241 cttctaggtc taggcccggt gagagactcc acaccgcgga gaactgccat tctttcctgg
12301 gcatcccggg gatcccagag ccggcccagg tacctgcgca cgcgcgggtt tgcgggcagc
12361 cgcctgggct gtgggagcag cccgggcaga gctctcctgc ctctccacca gcccaccccg
12421 ccgcctgacc gccccctccc caccccccac cccccacccc cggaaaacgc gtcgtccccct
12481 gggctgggtg gagacccccg tcccgcgaaa caccgggccc cgcgcagcgt ccgggcctga
12541 ctccgctccg gcggctcgcc tcctgtgtgc cccgcgcca ccgtcgcccg cccgcccggg
12601 ccctgcagc ctcccagctg ccagcgcgga gctcctggcg gtcaaaagca tacctctgtc
12661 tgtctttgcc cgcttcctgg ctagacctgc gcgcagtgcg caccccggct gacgtgcaag
12721 ggagctcgct ggcctctctg tgcccttgtt cttccgtgaa attctggctg aatgtctccc
12781 cccaccttcc gacgctgtct aggcaaacct ggattagagt tacatctcct ggatgattag
12841 ttcagagata tattaaaatg cccctccct gtggatccta tagaagattt gcatcttttg
12901 tgtgatgagt gcagagatat gtcacaatat ccctgtaga aaagcctga aattggttta
12961 cataacttcg gtgatcagtg cagatgtgtt tcagaactcc atagtagact gaacctagag
13021 aatggttaca tcacttaggt gatcagtgta gagatatgtt aaaattctcg tgtagacaga
```

(SEQ ID NO: 1)

FIGURE 4

CCACCCCCCCCCCCCACCACCACCACCACCACCACCCCGCCGGCCGGCCCCAG
GCCTCGACGCCCTGGGTCCCTTCCGGGGTGGGGCGGGCTGTCCCAGGGGGCT
CACCGCCATTC[ATG]AAGGGGTGGAGCCTGCCTGCCTGTGGGCCTTTACAAGGG
CGGCTGGCTGGCTGGCTGGCTGTCCGGGCAGGCCTCCTGGCTGCACCTGCCGC
AGTGCACAGTCCGGCTGAGGTGCACGGGAGCCCGCCGGCCTCTCTCTGCCCGC
GTCCGTCCGTGAAATTCCGGCCGGGGCTCACCGCGATGGCCCTCCCGACACCC
TCGGACAGCACCCTCCCCGCGGAAGCCCGGGGACGAGGACGGCGACGGAGAC
TCGTTTGGACCCCGAGCCAAAGCGAGGCCCTGCGAGCCTGCTTTGAGCGGAAC
CCGTACCCGGGCATCGCCACCAGAGAACGGCTGGCCCAGGCCATCGGCATTCC
GGAGCCCAGGGTCCAGATTTGGTTTCAGAATGAGAGGTCACGCCAGCTGAGGC
AGCACCGGCGGGAATCTCGGCCCTGGCCCGGGAGACGCGGCCCGCCAGAAGG
CCGGCGAAAGCGGACCGCCGTCACCGGATCCCAGACCGCCCTGCTCCTCCGAG
CCTTTGAGAAGGATCGCTTTCCAGGCATCGCCGCCCGGGAGGAGCTGGCCAGA
GAGACGGGCCTCCCGGAGTCCAGGATTCAGATCTGGTTTCAGAATCGAAGGGC
CAGGCACCCGGGACAGGGTGGCAGGGCGCCCGCGCAGGCAGGCGGCCTGTGC
AGCGCGGCCCCGGCGGGGGTCACCCTGCTCCCTCGTGGGTCGCCTTCGCCCA
CACCGGCGCGTGGGGAACGGGGCTTCCCGCACCCCACGTGCCCTGCGCGCCTG
GGGCTCTCCCACAGGGGGCTTTCGTGAGCCAGGCAGCGAGGGCCGCCCCCGCG
CTGCAGCCCAGCCAGGCCGCGCCGGCAGAGGGGGTCTCCCAACCTGCCCCGGC
GCGCGGGGATTTCGCCTACGCCGCCCCGGCTCCTCCGGACGGGGCGCTCTCCC
ACCCTCAGGCTCCTCGGTGGCCTCCGCACCCGGGCAAAAGCCGGGAGGACCGG
GACCCGCAGCGCGACGGCCTGCCGGGCCCCTGCGCGGTGGCACAGCCTGGGCC
CGCTCAAGCGGGGCCGCAGGGCCAAGGGGTGCTTGCGCCACCCACGTCCCAGG
GGAGTCCGTGGTGGGGCTGGGGCCGGGGTCCCCAGGTCGCCGGGGCGGCGTG
GGAACCCCAAGCCGGGGCAGCTCCACCTCCCCAGCCCGCGCCCCGGACGCCT
CCGCCTCCGCGCGGCAGGGGCAGATGCAAGGCATCCCGGCGCCCTCCCAGGCG
CTCCAGGAGCCGGCGCCCTGGTCTGCACTCCCTGCGGCCTGCTGCTGGATGA
GCTCCTGGCGAGCCCGGAGTTTCTGCAGCAGGCGCAACCTCTCCTAGAAACGG
AGGCCCCGGGGGAGCTGGAGGCCTCGGAAGAGGCCGCCTCGCTGGAAGCACC
CCTCAGCGAGGAAGAATACCGGGCTCTGCTGGAGGAGCTT[TAG]GACGCGGGG
*TTGGGACGGGGTCGGGTGGTTCGGGGCAGGGCCGTGGCCTCTCTTTCGCGGGGAA*
*CACCTGGCTGGCTACGGAGGGGCGTGTCTCCGCCCCGCCCCTCCACCGGGCTGA*
*CCGGCCTGGGATTCCTGCCTTCTAG*GTCTAGGCCCGGTGAGAGACTCCACACC
GCGGAGAACTGCCATTCTTTCCTGGGCATCCCGGGGATCCCAGAGCCGGC
CCAGACCTGCGCGCAGTGCGCACCCCGGCTGACGTGCAAGGGAGCTCGCTGG
CCTCTCTGTGCCCTTGTTCTTCCGTGAAATTCTGGCTGAATGTCTCCCCCCACCT
TCCGACGCTGTCTAGGCAAACCTGGATTAGAGTTACATCTCCTGGATGATTAGT
TCAGAGATATATTAAAATGCCCCTCCCTGTG (SEQ ID NO: 42)

FIGURE 5

CCACCCCCCCCCCCACCACCACCACCACCACCACCCCGCCGGCCGGCCCCAG
GCCTCGACGCCCTGGGTCCCTTCCGGGGTGGGGCGGGCTGTCCCAGGGGGGCT
CACCGCCATTC[ATG]AAGGGGTGGAGCCTGCCTGCCTGTGGGCCTTTACAAGGG
CGGCTGGCTGGCTGGCTGGCTGTCCGGGCAGGCCTCCTGGCTGCACCTGCCGC
AGTGCACAGTCCGGCTGAGGTGCACGGGAGCCCGCCGGCCTCTCTGCCCGC
GTCCGTCCGTGAAATTCCGGCCGGGGCTCACCGCGATGGCCCTCCCGACACCC
TCGGACAGCACCCTCCCCGCGGAAGCCCGGGGACGAGGACGGCGACGGAGAC
TCGTTTGGACCCCGAGCCAAAGCGAGGCCCTGCGAGCCTGCTTTGAGCGGAAC
CCGTACCCGGGCATCGCCACCAGAGAACGGCTGGCCCAGGCCATCGGCATTCC
GGAGCCCAGGGTCCAGATTTGGTTTCAGAATGAGAGGTCACGCCAGCTGAGGC
AGCACCGGCGGGAATCTCGGCCCTGGCCCGGGAGACGCGGCCCGCCAGAAGG
CCGGCGAAAGCGGACCGCCGTCACCGGATCCCAGACCGCCCTGCTCCTCCGAG
CCTTTGAGAAGGATCGCTTTCCAGGCATCGCCGCCCGGGAGGAGCTGGCCAGA
GAGACGGGCCTCCCGGAGTCCAGGATTCAGATCTGGTTTCAGAATCGAAGGGC
CAGGCACCCGGGACAGGGTGGCAGGGCGCCCGCGCAGGCAGGCGGCCTGTGC
AGCGCGGCCCCGGCGGGGGTCACCCTGCTCCCTCGTGGGTCGCCTTCGCCCA
CACCGGCGCGTGGGGAACGGGGCTTCCCGCACCCCACGTGCCCTGCGCGCCTG
GGGCTCTCCCACAGGGGGCTTTCGTGAGCCAGGCAGCGAGGGCCGCCCCCGCG
CTGCAGCCCAGCCAGGCCGCGCCGGCAGAGGGGGTCTCCCAACCTGCCCCGGC
GCGCGGGGATTTCGCCTACGCCGCCCCGGCTCCTCCGGACGGGGCGCTCTCCC
ACCCTCAGGCTCCTCGGTGGCCTCCGCACCCGGGCAAAAGCCGGGAGGACCGG
GACCCGCAGCGCGACGGCCTGCCGGGCCCTGCGCGGTGGCACAGCCTGGGCC
CGCTCAAGCGGGGCCGCAGGGCCAAGGGGTGCTTGCGCCACCCACGTCCCAGG
GGAGTCCGTGGTGGGGCTGGGGCCGGGGTCCCCAGGTCGCCGGGGCGGCGTG
GGAACCCCAAGCCGGGGCAGCTCCACCTCCCCAGCCCGCGCCCCCGGACGCCT
CCGCCTCCGCGCGGCAGGGGCAGATGCAAGGCATCCCGGCGCCCTCCCAGGCG
CTCCAGGAGCCGGCGCCCTGGTCTGCACTCCCTGCGGCCTGCTGCTGGATGA
GCTCCTGGCGAGCCCGGAGTTTCTGCAGCAGGCGCAACCTCTCCTAGAAACGG
AGGCCCCGGGGGAGCTGGAGGCCTCGGAAGAGGCCGCCTCGCTGGAAGCACC
CCTCAGCGAGGAAGAATACCGGGCTCTGCTGGAGGAGCTT[TAG]GACGCGGGG
TCTAGGCCCGGTGAGAGACTCCACACCGCGGAGAACTGCCATTCTTTCCT
GGGCATCCCGGGGATCCAGAGCCGGCCCAGACCTGCGCGCAGTGCGCAC
CCCGGCTGACGTGCAAGGGAGCTCGCTGGCCTCTCTGTGCCCTTGTTCTTCCGT
GAAATTCTGGCTGAATGTCTCCCCCACCTTCCGACGCTGTCTAGGCAAACCTG
GATTAGAGTTACATCTCCTGGATGATTAGTTCAGAGATATATTAAAATGCCCCC
TCCCTGTG (SEQ ID NO: 43)

FIGURE 6 ggagggcgggctaccccgggaccttgggccccgagctcatgcatgttcataacgcggtgga
ggtggtaggtctttctaagggcctcctggctgcacctgccgcagtgcacaggccggctgag
gtgcacgggagcccgccggcctctctctgcccgcgtccgtccgtgaaattccggccggggc
tcaccgcgatggccctcccgacaccttcggacagcacctccccgcggaagcccggggac
gaggacggcgacggagactcgtttggaccccgagccaaagcgaggccctgcgagcctgctt
tgagcggaacccgtacccgggcatcgccaccagagaacggctggcccaggccatcggcatt
ccggagcccagggtccagatttggtttcagaatgagaggtcacgccagctgaggcagcacc
ggcgggaatctcggccctggccggggagacgcggcccgccagaaggccggcgaaagcggac
cgccgtcaccggatcccagaccgccctgctcctccgagcctttgagaaggatcgctttcca
ggcatcgccgccgggaggagctggccagagagacgggcctccggagtccaggattcaga
tctggtttcagaatcgaagggccaggcacccgggacagggtggcagggcgcccgcgcaggc
aggcggcctgtgcagcgcggcccccggcgggggtcaccctgctcctcgtgggtcgccttc
gcccacaccggcgcgtggggaacggggcttcccgcaccccacgtgccctgcgcgcctgggg
ctctcccacaggggctttcgtgagccaggcagcgagggccgccccgcgctgcagcccag
ccaggccgcgccggcagagggggatctcccaacctgccccggcgcgcggggatttcgcctac
gccgccccggctcctccggacggggcgctctcccaccctcaggctcctcggtggcctccgc
acccgggcaaaagccgggaggaccgggacccgcagcgcgacggcctgccgggcccctgcgc
ggtggcacagcctgggcccgctcaagcggggccgcagggccaagggtgcttgcgccaccc
acgtccaggggagtccgtggtggggctggggccggggtccccaggtcgccggggcggcgt
gggaaccccaagccggggcagctccacctcccagcccgcgccccggacgcctccgcggc
aagcacagatgccagccatccaggcgcctcccaacgctccaggagccggggcgctcgtct
acagtcacctccagcctgttatatgagctcctgtagacaccagagtttcagcaaaaggca
cgacctttcctagatccggcgccactgggggagctgaaggacgtggaagagcccgctctgc
tggaaccactcctcagccaggaagaacaccgggctctgctggaggagcaggttggagcggg
gttggggcggggtggggcaggacggcgccctctctttcgcggtgaacctctgactcggta
tggagaggcgtgccttcccttccagctgacctgtctaggatccctgagttccaggtccggt
gagagactccacacagaggagggctgtcattctttcctgagcatcccggggatcccagggc
ccgcccaggtaccgggaggtggactgtctactgcgcatgcgcaggtttgcaggcagcagcc
taggtttt (SEQ ID NO: 50)

FIGURE 7 ggagggcgggctaccccgggaccttgggccccgagctcatgcatgtt<u>cataa</u>cgcggtgga
ggtggtaggtcttctaagggcctcctggctgcacctgccgcagtgcacaggccggctgag
gtgcacgggagcccgccggcctctctctgcccgcgtccgtccgtgaaattccggccggggc
tcaccgcg<span style="border:1px solid">atg</span>gccctcccgacaccttcggacagcaccctcccgcggaagcccggggac
gaggacggcgacggagactcgtttggaccccgagccaaagcgaggccctgcgagcctgctt
tgagcggaacccgtaccgggcatcgccaccagagaacggctggcccaggccatcggcatt
ccggagcccagggtccagatttggtttcagaatgagaggtcacgccagctgaggcagcacc
ggcgggaatctcggccctggccggggagacgcggccgccagaaggccggcgaaagcggac
cgccgtcaccggatcccagaccgccctgctcctccgagcctttgagaaggatcgctttcca
ggcatcgccgcccggggaggagctggccagagagacgggcctcccggagtccaggattcaga
tctggtttcagaatcgaagggccaggcacccgggacagggtggcagggcgcccgcgcaggc
aggcggcctgtgcagcgcggcccccggcggggtcaccctgctcctcgtgggtcgccttc
gcccacaccggcgcgtggggaacggggcttcccgcaccccacgtgccctgcgcgcctgggg
ctctcccacagggggctttcgtgagccaggcagcgagggccgcccccgcgctgcagcccag
ccaggccgcgccggcagaggggatctcccaacctgccccggcgcgcggggatttcgcctac
gccgccccggctcctccggacggggcgctctcccacccctcaggctcctcggtggcctccgc
acccgggcaaaagccggggaggaccgggacccgcagcgcgacggcctgccgggcccctgcgc
ggtggcacagcctgggcccgctcaagcggggccgcagggccaaggggtgcttgcgccaccc
acgtcccaggggagtccgtggtggggctggggccggggtcccaggtcgccggggcggcgt
gggaaccccaagccggggcagctccacctcccagcccgcgcccccggacgcctccgcggc
aagcacagatgccagccatccaggcgcctcccaaccgctccaggagccggggcgctcgtct
acagtcacctccagcctgttatatgagctcctg<span style="border:1px solid">tag</span>acaccagagtttcagcaaaaggca
cgacctttcctagatccggcgccactggggggagctgaaggacgtggaagagcccgctctgc
tggaaccactcctcagccaggaagaacaccgggctctgctggaggagcaggttggagcggg
gttggggcggggtgggggcaggacggcgccctctctttcgcggtgaacctctgactcggta
tggagaggcgtgccttccttccagctgacctgtctaggatccctgagttccaggtccggt
gagagactccacacagaggagggctgtcattctttcctgagcatcccggggatcccagggc
ccgcccaggtaccgggaggtggactgtctactgcgcatgcgcaggtttgcaggcagcagcc
taggttttccaaccagcccaggcggagctctcattccttttccccagcgttcttcagtcg
agttggcggagacctcagtccgcgaagcgctgggccggggcagaagccaggccagttctcc
tttccgtggctcgactcctctgcctcttcgctcaccaacacttgccaaccccgtcccgcc
agcctcctcgccag (SEQ ID NO: 51)

FIGURE 8

ATGTCTTATCGTCACTTCCGTGTCATCCTATCCCTGACCTCCCCACAGCCCACA
GCTCTTGTCATAGGCCAGCGGGACCTCGCACTCCGGGAAAACGTGGGGTGCCC
GGTGCAGGCCGAGAGCTCGGCCCACAGCCGCGTCTGCTTGCGGGGCGCCCACC
AGCTCACCAGCCCTCCGGATCGCCGGCCCGGGGGACCTGTTGCTCGCGTGTCT
CCCGCCCCGAAAGCGCGACCACGTTGGCTGTTTCCCGAGCTCTGCGGGGACA
CAGAAACCTCCAGCGAAGCGTGGAAAAGCAGCATCGTGACTTCGCTCTCCTTT
CCGGTTTCCAGACCGGCCACAGTGGAGACTCCCCTTGTTGCAGGAAACAGGAA
TCCGTGGTCAGGCCAATTACTGGAGAACCTCAGAGAGCCAGCCCCGGAAGCCC
CTCTTTCCCCTCCAATCCGGCCCTGCACCCACCCACCCCACAAGGCCCTGGTCC
CTGTGGTTTTCGGCTTCGGAGGGCGGGCTACCCCGGGACCTTGGGCCCCGAGC
TCATGCATGTTCATAACGCGGTGGAGGTGGTAGGTCTTTCTAAGGGCCTCCTGG
CTGCACCTGCCGCAGTGCACAGGCCGGCTGAGGTGCACGGGAGCCCGCCGGCC
TCTCTCTGCCCGCGTCCGTCCGTGAAATTCCGGCCGGGGCTCACCGCG[ATG]GC
CCTCCCGACACCCTCGGACAGCACCCTCCCCGCGGAAGCCCGGGGACGAGGAC
GGCGACGGAGACTCGTTTGGACCCCGAGCCAAAGCGAGGCCCTGCGAGCCTGC
TTTGAGCGGAACCCGTACCCGGGCATCGCCACCAGAGAACGGCTGGCCCAGGC
CATCGGCATTCCGGAGCCCAGGGTCCAGATTTGGTTTCAGAATGAGAGGTCAC
GCCAGCTGAGGCAGCACCGGCGGGAATCTCGGCCCTGGCCCGGGAGACGCGG
CCCGCCAGAAGGCCGGCGAAAGCGGACCGCCGTCACCGGATCCCAGACCGCC
CTGCTCCTCCGAGCCTTTGAGAAGGATCGCTTTCCAGGCATCGCCGCCCGGGA
GGAGCTGGCCAGAGAGACGGGCCTCCCGGAGTCCAGGATTCAGATCTGGTTTC
AGAATCGAAGGGCCAGGCACCCGGGACAGGGTGGCAGGGCGCCCGCGCAGGC
AGGCGGCCTGTGCAGCGCGGCCCTGGCGGGGGTCACCCTGCTCCCTCGTGGG
TCGCCTTCGCCCACACCGGCGCGTGGGGAACGGGGCTTCCCGCACCCCACGTG
CCCTGCGCGCCTGGGGCTCTCCCACAGGGGGCTTTCGTGAGCCAGGCAGCGAG
GGCCGCCCCGCGCTGCAGCCCAGCCAGGCCGCGCCGGCAGAGGGGGTCTCCC
AACCTGCCCCGGCGCGCGGGGATTTCGCCTACGCCGCCCCGGCTCCTCCGGAC
GGGGCGCTCTCCCACCCTCAGGCTCCTCGGTGGCCTCCGCACCCGGGCAAAAG
CCGGGAGGACCGGGACGCGCAGCGCGACGGCCTGCCGGGCCCCTGCGCGGTG
GCACAGCCTGGGCCCGCTCAAGCGGGGCCGCAGGGCCAAGGGGTGCTTGCGC
CACCCACGTCCCAGGGGAGTCCGTGGTGGGGCTGGGGCCGGGGTCCCCAGGTC
GCCGGGGCGGCGTGGGAACCCCAAGCCGGGGCAGCTCCACCTCCCCAGCCCGC
GCCCCCGGACGCCTCCGCGGCAAGCACAGATGCCAGCCATCCAGGCGCCTCCC
AACCGCTCCAGGAGCCGGGGCGCTCGTCTACAGTCACCTCCAGCCTGTTATAT
GAGCTCCTG[TAG]ACACCAGAGTTTCAGCAAAAGGCACGACCTTTCCTAGATCC
GGCGCCACTGGGGGAGCTGAAGGACGTGGAAGAGCCCGCTCTGCTGGAACCA
CTCCTCAGCCAGGAAGAACACCGGGCTCTGCTGGAGGAGCAGAGGTGCCTGTT
GCTCAAGTCTCTGCCCCGCCCCCGAAAGTGTGACCATGTTGACTGTTTGTTT
CCCGAGCTCTGTGGGGACCCAGAAACTTCCAGGAATGCGTGGAACACCAGCAT
CGTTTGTCGAGTGCGCCCGTCCTGTGGTGGGAGCAGTGGCCCCGAGCGTGCC
CACGGGCCCCGGCTTGGGTTTCTCTCGTGTTTAGAATGGTATGGCCGTAGACAA
TGGCGGTGGCGCCTGGCTGGTCCAAGAGCCCGGTCCAGCTACGCGCGTCTGAT
TCCAGGCGTCACCACCAACCCGGGGCCGCGAGGCTGGGATCAGGCACCCCGG
AGCCGCTCGCCCGCGGCCGGGCTGCTCTCCCCTCTATACGCCCAAGCACCAG
TCGCCGCGCTGCGTTTTCCGCCGGCCTCGCAGAGCGTCCCGCTATCGCCGGCGG
CCAGACCACGCGCAGGACCGCTGA (SEQ ID NO: 52)

FIGURE 20

MKGWSLPACGPLQGRLAGWLAVRAGLLAAPAAVHSPAEVHGSPPASLCPRPSVKFRPG
LTAMALPTPSDSTLPAEARGRGRRRRLVWTPSQSEALRACFERNPYPGIATRERLAQAI
GIPEPRVQIWFQNERSRQLRQHRRESRPWPGRRGPPEGRRKRTAVTGSQTALLLRAFE
KDRFPGIAAREELARETGLPESRIQIWFQNRRARHPGQGGRAPAQAGGLCSAAPGGGH
PAPSWVAFAHTGAWGTGLPAPHVPCAPGALPQGAFVSQAARAAPALQPSQAAPAEGV
SQPAPARGDFAYAAPAPPDGALSHPQAPRWPPHPGKSREDRDPQRDGLPGPCAVAQP
GPAQAGPQGQGVLAPPTSQGSPWWGWRGPQVAGAAWEPQAGAAPPPQPAPPDAS
ASARQGQMQGIPAPSQALQEPAPWSALPCGLLLDELLASPEFLQQAQPLLETEAPGELE
ASEEAASLEAPLSEEEYRALLEEL (SEQ ID NO: 59)

FIGURE 21

MALPTPSDSTLPAEARGRGRRRRLVWTPSQSEALRACFERNPYPGIATRERLAQAIGIPE
PRVQIWFQNERSRQLRQHRRESRPWPGRRGPPEGRRKRTAVTGSQTALLLRAFEKDR
FPGIAAREELARETGLPESRIQIWFQNRRARHPGQGGRAPAQAGGLCSAAPGGGHPAP
SWVAFAHTGAWGTGLPAPHVPCAPGALPQGAFVSQAARAAPALQPSQAAPAEGISQPA
PARGDFAYAAPAPPDGALSHPQAPRWPPHPGKSREDRDPQRDGLPGPCAVAQPGPAQ
AGPQGQGVLAPPTSQGSPWWGWRGPQVAGAAWEPQAGAAPPPQPAPPDASAAST
DASHPGASQPLQEPGRSSTVTSSLLYELL (SEQ ID NO: 60)

FIGURE 27

GabriëlspLAM (SEQ ID NO: 62) corresponds to the DUX4 mRNA Dixit et al
TapscottpLAM (SEQ ID NO: 63) corresponds to the DUX4 mRNA Snider et al
D4Z4 junction (SEQ ID NO: 61) corresponds to the DUX4 mRNA Coppée et al Stop codon
start (GT or GC) and end (AG) of introns: inside donor and acceptor splice sites respectively
polyA signal

```
D4Z4junction    CTCTGCTGGAGGAGCTTACGACGCGGGGTTGGGACGGGGTCGGGTGGTTCGGGGCAGGG
GabriëlspLAM    CTCTGCTGGAGGAGCTTACGACGCGGGGTTGGGACGGGGTCGGGTGGTTCGGGGCAGGG
TapscottpLAM    CTCTGCTGGAGGAGCTTACGACGCGGGGTTGGGACGGGGTCGGGTGGTTCGGGGCAGGG
                ************************************************************

D4Z4junction    CCGTGGCCTCTCTTTCGCGGGGAACACCTGGCTGGCTACGGAGGGGCGTGTCTCCGCCCC
GabriëlspLAM    CCGTGGCCTCTCTTTCGCGGGGAACACCTGGCTGGCTACGGAGGGGCGTGTCTCCGCCCC
TapscottpLAM    CCGTGGCCTCTCTTTCGCGGGGAACACCTGGCTGGCTACGGAGGGGCGTGTCTCCGCCCC
                ************************************************************

D4Z4junction    GCCCCCTCCACCGGGCTGACCGGCCTGGGATTCCTGCCTTCTAGGTCTAGGCCCGGTGAG
GabriëlspLAM    GCCCCCTCCACCGGGCTGACCGGCCTGGGATTCCTGCCTTCTAGGTCTAGGCCCGGTGAG
TapscottpLAM    GCCCCCTCCACCGGGCTGACCGGCCTGGGATTCCTGCCTTCTAGGTCTAGGCCCGGTGAG
                ************************************************************

D4Z4junction    AGACTCCACACCGCGGAGAACTGCCATTCTTTCCTGGGCATCCCGGGGATCCCAGAGCCG
GabriëlspLAM    AGACTCCACACCGCGGAGAACTGCCATTCTTTCCTGGGCATCCCGGGGATCCCAGAGCCG
TapscottpLAM    AGACTCCACACCGCGGAGAACTGCCATTCTTTCCTGGGCATCCCGGGGATCCCAGAGCCG
                ************************************************************

D4Z4junction    GCCCAGGTACCAGCAGGTGGGCCGCCTACTGCGCACGCGGGTTTGCGGGCAGCCGCCT
GabriëlspLAM    GCCCAGGTACCTGCG-----------------------CACGCGGGTTTGCGGGCAGCCGCCT
TapscottpLAM    GCCCAGGTACCAGCAGGTGGGCCGCCTACTGCGCACGCGGGTTTGCGGGCAGCCGCCT
                ***********,**.                     ***************************

D4Z4junction    GGGCTGTGGGAGCAGCCCGGGCAGAGCTCTCCTGCCTCTCCACCAGCCCACCCCGCCGCC
GabriëlspLAM    GGGCTGTGGGAGCAGCCCGGGCAGAGCTCTCCTGCCTCTCCACCAGCCCACCCCGCCGCC
TapscottpLAM    GGGCTGTGGGAGCAGCCCGGGCAGAGCTCTCCTGCCTCTCCACCAGCCCACCCCGCCGCC
                ************************************************************

D4Z4junction    TGACCGCCCCCTCCCCACCCCCACCCCCCACCCCCGGAAAACGCGTCGTCCCCTGGGCT
GabriëlspLAM    TGACCGCCCCCTCCCCACCCCCACCCCCCACCCCCGGAAAACGCGTCGTCCCCTGGGCT
TapscottpLAM    TGACCGCCCCCTCCCCACCCCC-ACCCCCACCCCCGGAAAACGCGTCGTCCCCTGGGCT
                ********************** *************************************

D4Z4junction    GGGTGGAGACCCCCGTCCCGCGAAACACCGGGCCCCGCGCAGCGTCCGGGCCTGACACCG
GabriëlspLAM    GGGTGGAGACCCCCGTCCCGCGAAACACCGGGCCCCGCGCAGCGTCCGGGCCTGACTCCG
TapscottpLAM    GGGTGGAGACCCCCGTCCCGCGAAACACCGGGCCCCGCGCAGCGTCCGGGCCTGACACCG
                ******************************************************;***

D4Z4junction    CTCCGGCGGCTCGCCTCCTATGCGCCCCCGCGCCACCGTCGCCCGCCCGCCCGGGCCCCT
GabriëlspLAM    CTCCGGCGGCTCGCCTCCTGTGTGCCCCCGCGCCACCGTCGCCCGCCCGCCCGGGCCCCT
TapscottpLAM    CTCCGGCGGCTCGCCTCCTCTGCGCCCCCGCGCCACCGTCGCCCGCCCGCCCGGGCCCCT
                ******************* ** ************************************

D4Z4junction    GCAGCCGCCCAGGTGCCAGCACGGAGCGCCTGGCGGCGGAACGCAGACCCCAGGCCCGGC
GabriëlspLAM    GCAGCCTCCCAGCTGCCAGCGCGGAGCTCCTGGCGGTCAAAAGCATACCTCTGTCTG---
TapscottpLAM    GCAGCCTCCCAGCTGCCAGCGCGGAGCTCCTGGCGGTCAAAAGCATACCTCTGTCTG---
                ****** ***** *******.****** ******** .**.*** *** *;* *

D4Z4junction    GCACACCGGGGACGCTGAGCGTTCCAGGCGGGAGGGAAGGCGGGCAGAGATGGAGAGAGG
GabriëlspLAM    ------------TCTTTGCCCGCTTCCTG---
```

FIGURE 27 (Cont.)

```
TapscottpLAM        ---------------TCTTTGCCCGCTTCCTG-----------------------------
                                   :*   **. ** * *. *

D4Z4junction        AACGGGAGACCTAGAGGGGCGGAAGGACGGGCGGAGGGACGTTAGGAGGGACGGAGGGAG
GabriëlspLAM        ------------------------------------------------------------
TapscottpLAM        ------------------------------------------------------------

D4Z4junction        GCAGGGAGGCAGGGAGGAACGGAGGGAAAGACAGAGCGACGCAGGGACTGGGGGCGGGCG
GabriëlspLAM        --------------------------------------------GCTAGACCTGCGCGCAG---
TapscottpLAM        --------------------------------------------GCTAGACCTGCGCGCAG---
                                                                **.:.*** * **.*

D4Z4junction        GGAGGGAGCCGGGGAACGGGGGGAGGAAGGCAGGGAGGAAAAGCGGTCCTCCGCCTCCGG
GabriëlspLAM        ----------------------------------------TGCGCACCCCGGCTGACGT
TapscottpLAM        ----------------------------------------TGCGCACCCCGGCTGACGT
                                                            :*** :** ****  .**

D4Z4junction        GAGTAGCGGGACCCCCGCCCTCCGGGAAAACGGTCAGCGTCCGGCGCGGGCTGAGGGCTG
GabriëlspLAM        GCAAGGGAGCTCGCTGGCCTCTCTG--------TGCCCTTGTTCTTCCGTGAAATTCTGGCTG
TapscottpLAM        GCAAGGGAGCTCGCTGGCCTCTCTG--------TGCCCTTGTTCTTCCGTGAAATTCTGGCTG
                    *..:.* .* :* *  ***    * *        *  *;  **   ** *,..* . *****

D4Z4junction        GGCCCACAGCCGCCGCGCCGGCCGGCGGGGCACCACCCATTCGCCCCGGTTCCGTGGCCC
GabriëlspLAM        -----AATGTCTCCCCCCACCTTCCGACG-------------------------------
TapscottpLAM        -----AATGTCTCCCCCCACCTTCCGACG-------------------------------
                         ..:  :  * ** *.**   ***.**

D4Z4junction        AGGGAGTGGGCGGTTTCCTCCGGGACAAAAGACCGGGACTCGGGTTGCCGTCGGGTCTTC
GabriëlspLAM        ---------------CTGTCTAGGCAAACCTGGATTAGAGTT------------------
TapscottpLAM        ---------------CTGTCTAGGCAAACCTGGATTAGAGTT------------------
                                   * *   :...,*.*** *** *.*.***

D4Z4junction        ACCCGCGCGGTTCACAGACCGCACATCCCCAGGCTGAGCCCTGCAACGCGGCGCGAGGCC
GabriëlspLAM        ---------------------------ACATCTCCTGGATGATTAGT------TCAGAGATATATT
TapscottpLAM        ---------------------------ACATCTCCTGGATGATTAGT------TCAGAGATATATT
                                               ***** **:** ***   . *    *.*.*. * .

D4Z4junction        GACAGCCCCGGCCACGGAGGAGCCACACGCAGGACGACGGAGGCGTGATTTTGGTTTCCG
GabriëlspLAM        AAAATGCCCCCTCCCTGTGCATCCTATAGAAGATTTGCATCTTTTGTGTGATGAGTGCAG
TapscottpLAM        AAAATGCCCCCTCCCTGTGCATCCTATAGAAGATTTGCATCTTTTGTGTGATGAGTGCAG
                    .*.* ***   *.* *;*** **;..:.*.**.:   .*. .   .* ;**. * *.*

D4Z4junction        CGTGGCTTTGCCCTCCGCAAGGCGGCCTGTTGCTCACGTCTCTCCGGCCCCCGAAAGGCT
GabriëlspLAM        AG----------------------------------ATATGTCACAATATCCCTGTAG------
TapscottpLAM        AG----------------------------------ATATGTCACAATATCCCTGTAG------
                    .*                                  : * ***;*:.  **** *;*.

D4Z4junction        GGCCATGCCGACTGTTTGCTCCCGGAGCTCTGCGGGCACCCGGAAACATGCAGGGAAGGG
GabriëlspLAM        -AAAAAGCCTGAAATTGGTTTACATAACTTCGGTG-------------------------
TapscottpLAM        -AAAAAGCCTGAAATTGGTTTACATAACTTCGGTG-------------------------
                     ...*:***  ,.:.** * * .*. *.** *  *

D4Z4junction        TGCAAGCCCGGCACGGTGCCTTCGCTCTCCTTGCCAGGTTCCAAACCGGCCACACTGCAG
GabriëlspLAM        --------------------------------------ATCAGTGCAGATGTGTTTCAG
TapscottpLAM        --------------------------------------ATCAGTGCAGATGTGTTTCAG
                                                          ; **.: *.*.  .  * ***

D4Z4junction        ACTCCCCACGTTGCCGCACGCGGGAATCCATCGTCAGGCCATCACGCCGGGGAGGCATCT
GabriëlspLAM        AACTCCATAGTAGACTGAACCTAGAGAATGGTTACAT-----------------------
TapscottpLAM        AACTCCATAGTAGACTGAACCTAGAGAATGGTTACAT-----------------------
                    *.  **.:.**:*.*  *. * .**..:, .   :**

D4Z4junction        CCTCTCTGGGGTCTCGCTCTGGTCTTCTACGTGGAAATGAACGAGAGCCACACGCCTGCG
```

FIGURE 27 (Cont.)

```
GabriëlspLAM      ---------------CACTTAGGTGATCAGTGTAGAGAT--------------------
TapscottpLAM      ---------------CACTTAGGTGATCAGTGTAGAGAT--------------------
                                 *.** :*** :**:. **.**.**

D4Z4junction      TGTGCGAGACCGTCCCGGCAACGGCGACGCCCACAGGCATTGCCTCCTTCACGGAGAGAG
GabriëlspLAM      ------------------------------------------ATGTTAAAATTCTCGTGTAGACAG
TapscottpLAM      ------------------------------------------ATGTTAAAATTCTCGTGTAGACAG
                                                            . .**...:   **. * *** **

D4Z4junction      GGCCTGGCACACTCAAGACTCCCACGGAGGTTCAGTTCCACACTCCCCTCCACCCTCCCA
GabriëlspLAM      AGCCTAGACAATTGTTACATCACCTAGTG-------------------------ATCAGT
TapscottpLAM      AGCCTAGACAATTGTTACATCACCTAGTG-------------------------ATCAGT
                  .****.*...* * ::...**.*. .*:*                          .**. :

D4Z4junction      GGCTGGTTCTCCCTGCTGCCGACGCGTGGGAGCCCAGAGAGCGGCTTCCCGTTCCCGCG
GabriëlspLAM      GCAGGGATAAGTCATAAAGCCTCCTGTAGG------CAGAGTGTAGGCAAGTGTTCCC----
TapscottpLAM      GCAGGGATAAGTCATAAAGCCTCCTGTAGG--------CAGAGTGTAGGCAAGTGTTCCC----
                  * . **:*:. *.*..:*** .*  :**     *****:* .*  :. ******

D4Z4junction      GGATCCCTGGAGAGGTCCGGAGAGCCGGCCCCCGAAACGCGCCCCCCTCCCCCCTCCCCC
GabriëlspLAM      ----TCCCTGGGCTGATCAG--------------------TGCAGAGATATCTCACAAAGCCCCT
TapscottpLAM      ----TCCCTGGGCTGATCAG--------------------TGCAGAGATATCTCACAAAGCCCCT
                      *******. :*.**.*                    :.*. . . ***.*... ****

D4Z4junction      CTCTCCCCCTTCCTCTTCGTCTCTCCGGCCCCACCACCACCACCGCCACCACGCCCTCCC
GabriëlspLAM      ATAAGCCAAACCTTGACAAGGGTTACATCACCTGTTTGAGCAGTGGAAATATATATCACA
TapscottpLAM      ATAAGCCAAACCTTGACAAGGGTTACATCACCTGTTTGAGCAGTGGAAATATATATCACA
                  .*.:  **.. : * *  :  ..  End of D4Z4-D4Z4 transcript      . .*.

D4Z4junction      CCCCCCCCCCCCCCCCCACCACCACCACCACCACCCCGCCGGCCGGCCCCAGGCCTCGA
GabriëlspLAM      AAGCCCCTGTAGACAAAGCCCAGACAATTTTTACATCTCCTGAG----------------
TapscottpLAM      AAGCCCCTGTAGACAAAGCCCAGACAATTTTTACATCTCCTGAG----------------
                  .. *****    . .*.....**..  **.*  ; **. * ** *,.
```

FIGURE 31

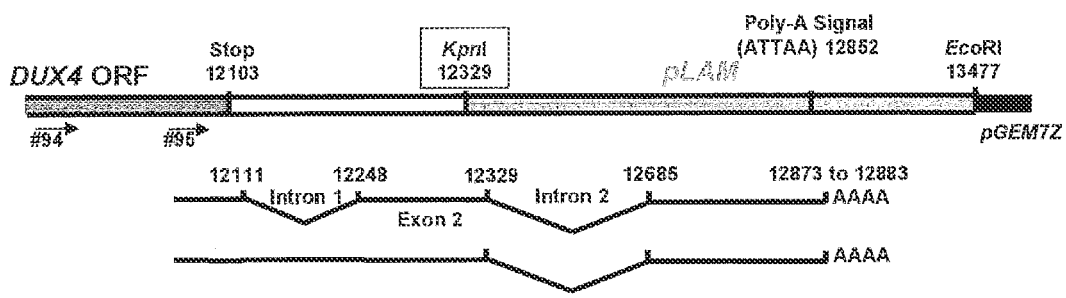

```
12001 agaaacggag gccccggggg agctggaggc ctcggaagag gccgcctcgc tggaagcacc
12061 cctcagcgag gaagaatacc gggctctgct ggaggagctt tag gacgcgg ggttgggacg
12121 gggtcgggtg gttcggggca gggccgtggc ctctctttcg cggggaacac ctggctggct
12181 acggaggggc gtgtctccgc ccgccccct ccaccgggct gaccggcctg ggattcctgc
12241 cttctaggtc taggccggt gagagactcc acaccgcgga gaactgccat tctttcctgg
12301 gcatcccggg gatcccagag ccggccagg tacctgcgca cgcgcggtt tgcgggcagc
12361 cgcctgggct gtgggagcag cccgggcaga gctctcctgc ctctccacca gcccaccccg
12421 ccgcctgacc gccccctccc caccccccac ccccaccccc cggaaaacgc gtcgtcccct
12481 gggctgggtg gagaccccg tcccgcgaaa caccgggccc cgcgcagcgt ccggcctga
12541 ctccgctccg gcggctcgcc tcctgtgtgc ccccgcgcca ccgtcgcccg cccgccggg
12601 cccctgcagc ctcccagctg ccagcgcgga gctcctggcg gtcaaaagca tacctctgtc
12661 tgtctttgcc cgcttcctgg ctagacctgc gcgcagtgcg caccccggct gacgtgcaag
12721 ggagctcgct ggcctctctg tgccttgtt cttccgtgaa attctggctg aatgtctccc
12781 cccaccttcc gacgctgtct aggcaaacct ggattagagt tacatctcct ggatgattag
12841 ttcagagata tattaaaatg ccccctccct gtggatccta tagaagattt gcatcttttg
12901 tgtgatgagt gcagagatat gtcacaatat ccctgtaga aaaagcctga aattggttta
12961 cataacttcg gtgatcagtg cagatgtgtt tcagaactcc atagtagact gaacctagag
13021 aatggttaca tcacttaggt gatcagtgta gagatatgtt aaaattctcg tgtagacaga
```

(SEQ ID NO: 1)

AGENTS USEFUL IN TREATING FACIOSCAPULOHUMERAL MUSCULAR DYSTROPHY

CROSS-REFERENCE TO RELATED APPLICATIONS

This application is a continuation of U.S. patent application Ser. No. 16/562,030, filed Sep. 5, 2019, which is a continuation of U.S. patent application Ser. No. 15/873,751, filed Jan. 17, 2018, which is a continuation of U.S. patent application Ser. No. 15/047,258 (now U.S. Pat. No. 9,988,628), filed Feb. 18, 2016, which is a continuation of U.S. patent application Ser. No. 14/078,133 (abandoned), filed Nov. 12, 2013, which is a divisional of U.S. application Ser. No. 13/225,384 (abandoned) filed Sep. 2, 2011, which claims priority to European Patent Application No. 10175125.3, entitled "Agents useful in treating facioscapulohumeral muscular dystrophy," filed on Sep. 2, 2010; which applications are each incorporated herein by reference in their entireties.

REFERENCE TO SEQUENCE LISTING

The material in the ASCII text filed submitted herewith, is incorporated herein by reference. The ACSII text file is named "SequenceListing.txt", created Sep. 5, 2019 and is 37 KB in size.

FIELD OF THE INVENTION

The invention generally relates to diseases and conditions the treatment of which can benefit from reducing the expression of double homeobox 4 and/or double homeobox 4c. Such diseases and conditions include inter alia those comprising increased levels and/or increased activity of double homeobox 4 and/or double homeobox 4c, and more particularly include facioscapulohumeral muscular dystrophy. Such diseases and conditions also include those comprising expression of a fusion protein between DUX4 or DUX4c and another, unrelated protein, more particularly wherein the disease or condition is a tumour, even more particularly a sarcoma such as Ewing's family tumours, paediatric undifferentiated soft tissue sarcomas and rhabdomyosarcomas. The invention concerns agents, more specifically antisense agents and RNA interference agents, capable of reducing or abolishing the expression of double homeobox 4 and/or double homeobox 4c, and elaborates methods, uses and further aspects employing such agents.

BACKGROUND OF THE INVENTION

Facioscapulohumeral muscular dystrophy (FSHD, FSHMD or FSH) also known as Landouzy-Dejerine muscular dystrophy is an autosomal dominant muscle disorder affecting about 1/20,000 births. It is characterised by progressive weakness and atrophy of the muscles from the face, the upper-arms and shoulder girdle to the lower limbs.

FSHD is genetically linked to contractions of the D4Z4 repeat array on the 4q35 subtelomeric region. Non-affected individuals typically have between 11-100 copies of the 3.3-kb D4Z4 element, while FSHD patients only have 1-10 copies. A typical feature associated with the genetic defect is a decrease in DNA methylation of the contracted D4Z4 array as compared to non-affected individuals (van Overveld et al. 2005 (Ann Neurol. 58: 569-76.)). Whereas a small group of patients with a typical FSHD phenotype does present more than 10 copies of the D4Z4 element, their DNA methylation level is low, similarly to that found in contracted D4Z4 arrays. DNA hypomethylation is typically associated with an open chromatin structure suitable for transcription (de Greef et al. 2009 (Hum Mutat. 30: 1449-59)).

Gabriëls et al. 1999 (Gene 236(1): 25-32) identified the double homeobox 4 (DUX4) gene within each D4Z4 element repeated in the array. The DUX4 sequence was later corrected as published by Kowaljow et al. 2007 (Neuromuscul Disord 17: 611-23) and is available under the NCBI Genbank accession number: AF117653.2. Subsequent studies showed that the encoded DUX4 protein was expressed in primary myoblasts and biopsies of patients with FSHD but not in non-affected individuals, and that the DUX4 protein is a transcription factor targeting a large set of genes including inter alia genes encoding further transcription factors, and that DUX4 gene activation at the FSHD locus initiates a transcription cascade leading to muscle atrophy, inflammation, decreased differentiation potential and oxidative stress, recapitulating the key features of FSHD (Bosnakowski et al. 2008 (EMBO J 27(20): 2766-79); Kowaljow et al. 2007 (Neuromuscul Disord 17: 611-23); Dixit et al. 2007 (Proc Natl Acad Sci USA 104: 18157-18162)). Double homeobox 4 is thus considered a major contributor to the pathology of FSHD muscles.

Dixit et al. 2007 (supra) also demonstrated in myoblast cultures that whereas transcription can initiate at any D4Z4 element within the repeat array, a prevalent stable DUX4 mRNA originates from the most distal D4Z4 unit and extends into the pLAM region which flanks the telomeric side of the D4Z4 array, whereby the pLAM region provides the DUX4 transcript with an intron and a polyadenylation signal (FIGS. 1 and 2). However, also additional transcripts were identified that span several D4Z4 units, may have various parts spliced out, and may also comprise the pLAM region (Snider et al. 2009. Hum Mol Genet 18: 2414-30; Coppée et al., unpublished, see FIGS. 26-28). Moreover, polymorphisms have been found in the pLAM region such as the presence or absence of a 1.6 kb sequence within its intron (Gabriëls et al. 1999, supra; van Deutekom et al. 2009. Hum Mutat 30: 1449-59).

Lemmers et al. 2010 (Science, August 19) propose a unifying genetic model for FSHD.

Furthermore, the homologous DUX4c gene was identified 42 kb centromeric of the D4Z4 array, within a truncated and inverted solitary D4Z4 unit. The DUX4c gene encodes a 47-kDa protein with a double homeodomain identical to DUX4 but divergent in the carboxyl-terminal region. The DUX4c protein is expressed at low levels in control muscles, it is induced in muscles of patients affected with Duchenne muscular dystrophy and is present at similar or yet higher levels in FSHD muscles. Additional experiments suggested that DUX4c could be involved in myoblast proliferation during muscle regeneration and that changes in its expression could contribute to the FSHD pathology (Ansseau et al. 2009 (PLoS One 4(10): e7482).

In certain tumour types a fusion gene is seen that includes the 3' region of the DUX4 gene as a result of chromosome rearrangements. Fusion between CIC, a human homolog of *Drosophila capicua*, and DUX4 was seen in Ewing's family tumours (EFTs) (Kawamura-Saito et al. 2006. Hum Mol Genet 15: 2125-2137) and paediatric undifferentiated soft tissue sarcomas (USTS) (Yoshimoto et al. 2009. Cancer Genet Cytogenet 195: 1-11), and rhabdomyosarcomas (RMS) showed fusion between the EWSR1 gene and DUX4. (Sirvent et al. 2009. Caner Genet Cytogenet 195:

12-08). As a consequence of fusion with the C-terminal fragment of DUX4 the resulting fusion proteins acquire an enhanced transcriptional activity, which leads to tumour formation.

SUMMARY OF THE INVENTION

The inventors postulate that down-regulating the expression of double homeobox 4 and/or double homeobox 4c can counteract the pathological effects thereof and allows muscle regeneration to occur in FSHD patients. The inventors further postulate that down-regulating the expression of double homeobox 4 and/or double homeobox 4c can counteract the enhanced transcriptional activity of DUX4-containing fusion proteins that is seen in certain tumours, particularly in certain types of sarcomas, and thereby have a therapeutic benefit, e.g., slow down formation and/or progression, of such tumours.

Having conducted extensive tests the inventors realised that antisense agents targeting sequence elements involved in splicing of DUX4 or DUX4c transcripts can reduce or abolish the production of the respective proteins. This finding is unexpected, since antisense agents targeting sequence elements required for splicing were previously contemplated for therapeutic exon skipping to at least partly restore the functionality of defective proteins, such as for example to remove nonsense mutations or restore the reading frame disrupted by genomic deletions or duplications in the dystrophin gene in Duchenne muscular dystrophy (DMD) (Wilton et al. 2007 (Mol Ther 15(7): 1288-96); Adams et al. 2007 (BMC Mol Biol 8: 57)). Moreover, the introns of the DUX4 transcript are located in its 3' untranslated region (3' UTR), which is unusual, and interference with splicing would therefore not be expected to alter the DUX4 coding sequence or the production of the DUX4 protein.

The inventors also realised that antisense agents targeting sequence elements involved in polyadenylation of DUX4 or DUX4c transcripts can reduce or abolish the production of the respective proteins.

In an aspect the invention thus generally provides an antisense agent capable of reducing or abolishing the production of DUX4 or DUX4c proteins. An antisense agent as intended herein may be capable of binding to (annealing with) DUX4 or DUX4c genes. In particular, such antisense agent may be capable of binding to (annealing with) a sequence region in DUX4 or DUX4c (pre-mRNA) sequence.

Double homeobox 4 emerges as particularly implicated in the aetiology of facioscapulohumeral muscular dystrophy (FSHD). Hence, preferably disclosed herein are: an antisense agent capable of reducing or abolishing the production of DUX4 protein; an antisense agent capable of binding to DUX4 gene; an antisense agent capable of binding to a sequence region in DUX4 (pre-mRNA) sequence.

Also preferably disclosed herein are: an antisense agent capable of reducing or abolishing the production of DUX4 protein but not of DUX4c protein; an antisense agent capable of binding to DUX4 gene but not to DUX4c gene; an antisense agent capable of binding to a sequence region in DUX4 (pre-mRNA) sequence but not to a sequence region in DUX4c (pre-mRNA) sequence.

In an alternative, disclosed herein are: an antisense agent capable of reducing or abolishing the production of DUX4c protein but not of DUX4 protein; an antisense agent capable of binding to DUX4c gene but not to DUX4 gene; an antisense agent capable of binding to a sequence region in DUX4c (pre-mRNA) sequence but not to a sequence region in DUX4 (pre-mRNA) sequence.

In a preferred aspect the invention provides an antisense agent capable of binding to a sequence element required for splicing of the double homeobox 4 (DUX4) or double homeobox 4c (DUX4c) genes (as explained elsewhere in this specification, a mention of splicing or splicing of a gene generally refers to splicing of a gene's pre-mRNA to remove intervening sequence(s)). The antisense agent can reduce or abolish the production of the respective DUX4 or DUX4c proteins. For example and without being bound by any theory, such antisense agents might interfere with splicing of the DUX4 or DUX4c genes (pre-mRNA) or might act through another mechanism.

Double homeobox 4 emerges as particularly implicated in the aetiology of facioscapulohumeral muscular dystrophy (FSHD). Hence, preferably disclosed herein is an antisense agent capable of binding to a sequence element required for splicing of the double homeobox 4 (DUX4) gene. The antisense agent can reduce or abolish the production of DUX4 protein.

Also preferably disclosed herein is an antisense agent capable of binding to a sequence element required for splicing of the DUX4 gene but not of the DUX4c gene. The antisense agent can reduce or abolish the production of DUX4 protein but does not reduce or abolish the production of DUX4c protein. In an alternative, disclosed is an antisense agent capable of binding to a sequence element required for splicing of the DUX4c gene but not of the DUX4 gene. The antisense agent can reduce or abolish the production of DUX4c protein but does not reduce or abolish the production of DUX4 protein.

Sequence elements required for splicing of the DUX4 or DUX4c genes as intended herein particularly denote cis sequence elements, i.e., those located within said DUX4 or DUX4c genes, respectively.

Sequence elements to be targeted by (i.e., selected to be bound by) antisense agents as disclosed herein may be preferably chosen from the group comprising or consisting of splice donor sites (i.e., 5' splice sites), splice acceptor sites (i.e., 3' splice sites), pyrimidine-rich or polypyrimidine tracts upstream of (i.e., 5' relative to) splice acceptor sites, exon-intron boundaries, intron-exon boundaries, branch sites and exonic splicing enhancer elements of the DUX4 or DUX4c genes. Splice donor sites and splice acceptor sites, exon-intron boundaries and intron-exon boundaries may be readily accessible for targeting and may thus constitute preferred sequence elements as intended herein. Further, particularly effective antisense agents as disclosed herein include those capable of binding to splice acceptor sites or intron-exon boundaries of the DUX4 or DUX4c genes.

Antisense agents as disclosed herein may preferably bind to a whole sequence element required for splicing DUX4 or DUX4c (i.e., may wholly overlap with or wholly anneal to such sequence element). Alternatively, antisense agents as disclosed herein may bind to one or more portions of a sequence element required for splicing DUX4 or DUX4c (e.g., may partly overlap with or partly anneal to such sequence element).

Reference to "binding to a sequence element required for splicing" also encompasses antisense agents that bind at a position sufficiently close to said element. For example, the antisense agents may bind at a position sufficiently close to said element to disrupt the binding and function of splicing machinery that would normally mediate a particular splicing reaction occurring at that element (e.g., such agents may bind to pre-mRNA at a position within about 3, about 6, or about 9 bases of said element).

In another preferred aspect the invention provides an antisense agent capable of binding to a sequence element required for polyadenylation of DUX4 or DUX4c genes (as explained elsewhere in this specification, a mention of polyadenylation or polyadenylation of a gene generally refers to polyadenylation of a gene's pre-mRNA). The antisense agent can reduce or abolish the production of the DUX4 or DUX4c proteins. For example and without being bound by any theory, such antisense agents might interfere with polyadenylation of the DUX4 or DUX4c genes (pre-mRNA) or might act through another mechanism.

Double homeobox 4 emerges as particularly implicated in the aetiology of FSHD. Preferably disclosed herein is thus an antisense agent capable of binding to a sequence element required for polyadenylation of the DUX4 gene. The antisense agent can reduce or abolish the production of DUX4 protein.

Also preferably disclosed herein is an antisense agent capable of binding to a sequence element required for polyadenylation of the DUX4 gene but not of the DUX4c gene. The antisense agent can reduce or abolish the production of DUX4 protein but does not reduce or abolish the production of DUX4c protein. In an alternative, disclosed is an antisense agent capable of binding to a sequence element required for polyadenylation of the DUX4c gene but not of the DUX4 gene. The antisense agent can reduce or abolish the production of DUX4c protein but does not reduce or abolish the production of DUX4 protein.

Also preferably disclosed herein is an antisense agent capable of binding to a sequence element required for polyadenylation of the DUX4 gene but not capable of binding to the DUX4c gene. The antisense agent can reduce or abolish the production of DUX4 protein but does not reduce or abolish the production of DUX4c protein. In an alternative, disclosed is an antisense agent capable of binding to a sequence element required for polyadenylation of the DUX4c gene but not capable of binding to the DUX4 gene. The antisense agent can reduce or abolish the production of DUX4c protein but does not reduce or abolish the production of DUX4 protein.

Sequence elements required for polyadenylation of the DUX4 or DUX4c genes as intended herein particularly denote cis sequence elements, i.e., those located within said DUX4 or DUX4c genes, respectively.

Sequence elements to be targeted by (i.e., selected to be bound by) antisense agents capable of binding to a sequence element required for polyadenylation of the DUX4 or DUX4c genes may be preferably polyadenylation signals (such as more preferably the polyadenylation signal ATTAAA) of the DUX4 or DUX4c genes.

Antisense agents capable of binding to a sequence element required for polyadenylation of the DUX4 or DUX4c genes may preferably bind to a whole sequence element required for polyadenylation of DUX4 or DUX4c (i.e., may wholly overlap with or wholly anneal to such sequence element). Alternatively, antisense agents capable of binding to a sequence element required for polyadenylation of the DUX4 or DUX4c genes may bind to one or more portions of a sequence element required for polyadenylation of DUX4 or DUX4c (e.g., may partly overlap with or partly anneal to such sequence element).

Reference to "binding to a sequence element required for polyadenylation" also encompasses antisense agents that bind at a position sufficiently close to said element (e.g., such agents may bind to pre-mRNA at a position within about 3, about 6, or about 9 bases of said element).

Antisense agents as intended herein preferably comprise or denote antisense molecules such as more preferably antisense nucleic acid molecules or antisense nucleic acid analogue molecules. Preferably, antisense agents may refer to antisense oligonucleotides or antisense oligonucleotide analogues. By means of an example and not limitation, such antisense agents or molecules may be between about 10 and about 100 nucleotides or nucleotide analogues in length, preferably between about 12 and about 80 nucleotides or nucleotide analogues in length, also preferably between about 15 and about 50 nucleotides or nucleotide analogues in length, more preferably between about 20 and about 40 (such as, e.g., between about 20 and about 30) nucleotides or nucleotide analogues in length.

Preferably disclosed herein are antisense agents including antisense nucleic acid analogue molecules, such as, e.g., antisense oligonucleotide analogues, more preferably antisense oligonucleotide analogues comprising a 2'-O-methylated phosphorothioate backbone or more preferably antisense oligonucleotide analogues comprising a phosphorodiamidate morpholino backbone as schematically illustrated in FIGS. 24 and 25, respectively. Splice-switching phosphorodiamidate morpholino oligomers have been successfully employed to restore dystrophin expression in DMD, thereby validating this oligonucleotide chemistry (Kinali et al. 2009 (Lancet Neurol 8: 918-28)).

Advantageously, an antisense agent as disclosed herein may be conjugated to a cell penetrating peptide (CPP) to enhance the cellular uptake of said antisense agents.

Further by means of an example and not limitation, such antisense agents or molecules may be configured to bind to (anneal with) a sequence region, more particularly a region in DUX4 or DUX4c (pre-mRNA) sequence, wherein said region is at least about 10 nucleotides in length, preferably at least about 12 nucleotides in length, also preferably at least about 15 nucleotides in length, more preferably at least about 20 nucleotides in length, even more preferably at least about 25 or at least about 30 nucleotides in length, such as for example between about 10 and about 100 nucleotides in length, preferably between about 12 and about 80 nucleotides in length, also preferably between about 15 and about 50 nucleotides in length, and more preferably between about 20 and about 40 (such as, e.g., between about 20 and about 30) nucleotides in length, wherein the reference to nucleotides may preferably denote consecutive nucleotides.

A DUX4 gene preferably intended for targeting by the antisense agents as disclosed herein resides in the distalmost D4Z4 unit which extends into the pLAM region flanking the telomeric side of the D4Z4 array. Such DUX4 gene leads to production of comparably stable mRNA(s) (Dixit et al. 2007, supra). As schematically illustrated in FIG. 2 with reference to an exemplary but non-limiting genomic sequence as shown in FIG. 3, such DUX4 gene comprises two introns which are located in its 3' UTR, namely intron 1 (or intron A) within the D4Z4 unit and intron 2 (or intron B) provided by the pLAM region. Such DUX4 gene further comprises a polyadenylation signal ATTAAA located within the pLAM region.

A DUX4 gene as intended herein may also denote a DUX4 transcription units that span several D4Z4 units, may display alternative splicing, and may comprise the pLAM region, in particular as disclosed by Snider et al. 2009, supra. As schematically illustrated in FIGS. 26 and 28, such DUX4 transcripts may comprise intron 1, intron ibis or intron 2a within the D4Z4 unit, intron 2 provided by the pLAM region or intron 2a bis provided by the D4Z4 unit and the pLAM region. Such DUX4 transcript further comprises a polyadenylation signal ATTAAA located within the pLAM region.

Hence, sequence elements to be targeted by anti-DUX4 antisense agents as disclosed herein, particularly sequence elements required for splicing of the DUX4 gene to be targeted by anti-DUX4 antisense agents capable of binding to such elements, preferably include those sequence elements (such as, e.g., splice donor sites, splice acceptor sites, exon-intron boundaries, intron-exon boundaries, pyrimidine-rich or polypyrimidine tracts, branch sites and/or exonic splicing enhancer elements) required for removal of said DUX4 intron 1, intron 1 bis, intron 2, intron 2a or intron 2a bis (preferably of intron 1 or 2) upon splicing of a DUX4 gene. Preferably, the targeted DUX4 sequence elements may be chosen from the group comprising or consisting of splice donor sites of said DUX4 intron 1, intron 1 bis, intron 2, intron 2a or intron 2a bis (preferably of intron 1 or 2) and splice acceptor sites of said DUX4 intron 1, intron 1 bis, intron 2, intron 2a or intron 2a bis (preferably of intron 1 or 2); more preferably from the group comprising or consisting of splice acceptor sites of said DUX4 intron 1, intron 1 bis, intron 2, intron 2a or intron 2a bis (preferably of intron 1 or 2); even more preferably may be the splice acceptor site of said DUX4 intron 2.

Sequence elements to be targeted by anti-DUX4 antisense agents as disclosed herein, particularly sequence elements required for polyadenylation of the DUX4 gene and to be targeted by anti-DUX4 antisense agents capable of binding to such elements, preferably include the polyadenylation signal ATTAAA.

As shown in an exemplary but non-limiting genomic sequence of the DUX4c gene (Genbank accession no. AY500824, sequence version 1, i.e., AY500824.1), the ORF encoding the DUX4c protein is found at positions 918-2042 of AY500824.1 and is not disrupted by introns. However, a larger exemplary but non-limiting genomic sequence of the DUX4c gene (Genbank accession no. NC_000004, sequence version 11, i.e., NC_000004.11, range 190940254 . . . 190945505 complement) indicates that the DUX4c ORF may be included within a larger DUX4c transcript containing six putative exons (denoted as exons 1 to 6) at respectively positions 1-65, 617-741, 966-1160, 1385-2945, 4034-4154 and 4911-5251 of NC_000004.11 (range 190940254 . . . 190945505, complement) (wherein putative exon 4 contains the DUX4c ORF) and corresponding five putative introns (denoted introns 1 to 5) at positions 66-616, 742-965, 1161-1384, 2946-4033 and 4155-4910 of NC_000004.11 (range 190940254 . . . 190945505, complement).

Hence, sequence elements to be targeted by anti-DUX4c antisense agents as disclosed herein, particularly sequence elements required for splicing of the DUX4c gene to be targeted by anti-DUX4c antisense agents capable of binding to such elements, preferably include those sequence elements (such as, e.g., splice donor sites, splice acceptor sites, exon-intron boundaries, intron-exon boundaries, pyrimidine-rich or polypyrimidine tracts, branch sites and/or exonic splicing enhancer elements) required for removal of said DUX4c introns, e.g., DUX4c introns 1, 2, 3, 4 or 5 upon splicing of such DUX4c gene. Preferably, the targeted DUX4c sequence elements may be chosen from the group comprising or consisting of splice donor sites of said DUX4c introns 1, 2, 3, 4 or 5 and splice acceptor sites of said DUX4c introns 1, 2, 3, 4 or 5; more preferably from the group comprising or consisting of splice acceptor sites of said DUX4c introns 1, 2, 3, 4 or 5.

Without limitation, where a targeted sequence element is a splice donor site in DUX4 or DUX4c genes, an antisense agent as disclosed herein may be configured to bind to a region in DUX4 or DUX4c sequence corresponding to positions about +30 to about −30, preferably about +25 to about −25, more preferably about +20 to about −20 relative to the respective exon-intron boundary (i.e., position +1 denoting the last base of the preceding exon and position −1 denoting the first base of the following intron). In particular, an antisense agent may be configured to bind to (anneal with) at least about 10 bases, preferably at least about 15 bases, more preferably at least about 20 bases, even more preferably at least about 25 bases or at least about 30 bases, such as to between about 10 and about 40 bases or to between about 20 and about 30 bases in any one of the above recited regions in DUX4 or DUX4c sequence, wherein said reference to bases may preferably denote consecutive bases. Preferably, such binding (annealing) will involve at least positions −1 or −2 (more preferably both positions −1 and −2) and/or positions +1 or +2 (more preferably both positions +1 and +2) relative to the respective exon-intron boundary. For example, such binding (annealing) may involve at least positions +1 to −1 or +1 to −2 or +2 to −1 or +2 to −2. These positions denote bases which adjoin the respective exon-intron boundary and which are particularly relevant for splicing. Hence, and without limitation, an antisense agent may be configured to bind to any one of the above recited regions in DUX4 or DUX4c sequence such that it anneals over (i.e., spans or crosses) the respective exon-intron boundary and base pairs with at least 1 base, preferably at least 2 bases, more preferably at least 5 bases and even more preferably at least 7 or at least 10 bases on each side of said exon-intron boundary, such as with between 1 and about 20 bases, preferably between 2 and about 15 bases or between 2 and about 10 bases on each side of said exon-intron boundary.

Without limitation, where a targeted sequence element is a splice acceptor site in DUX4 or DUX4c genes, an antisense agent as disclosed herein may be configured to bind to a region in DUX4 or DUX4c sequence corresponding to positions about −30 to about +30, preferably about −25 to about +25, more preferably about −20 to about +20 relative to the respective intron-exon boundary (i.e., position −1 denoting the last base of the preceding intron and position +1 denoting the first base of the following exon). In particular, an antisense agent may be configured to bind to (anneal with) at least about 10 bases, preferably at least about 15 bases, more preferably at least about 20 bases, even more preferably at least about 25 bases or at least about 30 bases, such as to between about 10 and about 40 bases or to between about 20 and about 30 bases in any one of the above recited regions in DUX4 or DUX4c sequence, wherein said reference to bases may preferably denote consecutive bases. Preferably, such binding (annealing) will involve at least positions −1 or −2 (more preferably both positions −1 and −2) and/or positions +1 or +2 (more preferably both positions +1 and +2) relative to the respective intron-exon boundary. For example, such binding (annealing) may involve at least positions −1 to +1 or −1 to +2 or −2 to +1 or −2 to +2. These positions denote bases which adjoin the respective intron-exon boundary and which are particularly relevant for splicing. Hence, and without limitation, an antisense agent may be configured to bind to any one of the above recited regions in DUX4 or DUX4c sequence such that it anneals over (i.e., spans or crosses) the respective intron-exon boundary and base pairs with at least 1 base, preferably at least 2 bases, more preferably at least 5 bases and even more preferably at least 7 or at least 10 bases on each side of said intron-exon boundary, such as with between 1 and about 20 bases, preferably between 2 and about 15 bases or between 2 and about 10 bases on each side of said intron-exon boundary.

In an example, an anti-DUX4 antisense agent may be configured to bind to (anneal with) at least about 10 bases, preferably at least about 15 bases, more preferably at least about 20 bases, even more preferably at least about 25 bases or at least about 30 bases, such as to between about 10 and about 40 bases or to between about 20 and about 30 bases, preferably wherein said reference to bases denotes consecutive bases, of any one of the following DUX4 sequences (SEQ ID NO: 2 to 9) or of variants thereof having at least about 80% and preferably at least about 90% or at least about 95% sequence identity to the respective sequences:

```
ggctctgctggaggagctttaggacgcggg | gttgggacggg
gtcgggtggttcggggcag
(SEQ ID NO: 2; positions +30 to -30 of
an exemplary DUX4 exon 1-intron 1 boundary;
the intron sequence is in italics);

gaggagctttaggacgcggg|gttgggacggggtcgggtgg
(SEQ ID NO: 3; positions +20 to-20 of an
exemplary DUX4 exon 1-intron 1 boundary; the
intron sequence is in italics);

gctgaccggcctgggattcctgccttctag | gtctaggccc
ggtgagagactccacaccgc
(SEQ ID NO: 4; positions -30 to +30
of an exemplary DUX4 intron 1-exon 2 boundary;
the intron sequence is in italics);

ctgggattcctgccttctag | gtctaggcccggtgagagac
(SEQ ID NO: 5; positions-20 to +20 of an
exemplary DUX4 intron 1-exon 2 boundary;
the intron sequence is in italics);

ggcatcccggggatcccagagccggcccag | gtacctgcgca
cgcgcgggtttgcgggcag (SEQ ID NO: 6; positions
+30 to -30 of an exemplary DUX4 exon
2-intron 2 boundary; the intron
sequence is in italics);

ggatcccagagccggcccag | gtacctgcgcacgcgcgggt
(SEQ ID NO: 7; positions +20 to -20 of
an exemplary DUX4 exon 2-intron 2 boundary;
the intron sequence is in italics);

tctgtctgtctttgcccgcttcctggctag | acctgcgcagt
gcgcacccggctgacg (SEQ ID NO: 8; positions -30
to +30 of an exemplary DUX4 intron 2-exon 3
boundary; the intron sequence is in italics).

tttgcccgcttcctggctag | acctgcgcagtgcgcacc
(SEQ ID NO: 9; positions -20 to +20 of
an exemplary DUX4 intron 2-exon 3 boundary;
the intron sequence is in italics).
```

Preferably, the anti-DUX4 antisense agent is capable of annealing over (i.e., span or cross) the respective exon-intron or intron-exon boundaries found in SEQ ID NO: 2 to 9 or in the variants thereof (indicated by the "|" symbol above). Also preferably, the anti-DUX4 antisense agent is capable of annealing with at least one and preferably both of the two intronic bases (indicated above in bold italics) adjacent to the respective exon-intron or intron-exon boundaries and/or (preferably "and") with at least one and preferably both of the two exonic bases (underlined above) adjacent to the respective exon-intron or intron-exon boundaries.

In non-limiting embodiments, an effective anti-DUX4 antisense agent may be configured to bind to (anneal with) any one of the following DUX4 sequences (SEQ ID NO: 10 to 15, 66) or to variants thereof having at least about 80% and preferably at least about 90% or at least about 95% sequence identity to the respective sequences, or to fragments thereof comprising at least 10 bases, or at least 12 bases, preferably at least about 15 bases, more preferably at least about 20 bases, even more preferably at least about 25 bases, preferably wherein said reference to bases denotes consecutive bases, of the respective sequences or variants. More specifically, such an anti-DUX4 antisense agent may comprise, consist essentially of or consist of a sequence (e.g., a nucleic acid sequence or nucleic acid analogue sequence) complementary to any one of said DUX4 sequences SEQ ID NO: 10 to 15, 66 or to variants thereof having at least about 80% and preferably at least about 90% or at least about 95% sequence identity to the respective sequences, or to fragments thereof comprising at least 10 bases, or at least 12 bases, preferably at least about 15 bases, more preferably at least about 20 bases, even more preferably at least about 25 bases, preferably wherein said reference to bases denotes consecutive bases, of the respective sequences or variants:

```
cttctaggtctaggcccggtgagag
(SEQ ID NO: 10; positions -7 to +18 of an
exemplary DUX4 intron 1-exon 2 boundary;
positions 12241-12265 of Genbank sequence
AF117653.2 (see FIG. 3); the
intron sequence is in italics);

tggctagacctgcgcgcagtgcgca
(SEQ ID NO: 11; positions -7 to +18 of an
exemplary DUX4 intron 2-exon 3 boundary;
positions 12678-12702 of AF117653.2; the
intron sequence is in italics);

cttcctggctagacctgcgcgcagt
(SEQ ID NO: 12; positions -12 to +13 of an
exemplary DUX4 intron 2-exon 3 boundary;
positions 12673-12697 of AF117653.2; the
intron sequence is in italics);

agacctgcgcgcagtgcgcaccccg
(SEQ ID NO: 13; positions -2 to +23 of an
exemplary DUX4 intron 2-exon 3 boundary;
positions 12685-12703 of AF117653.2; the
intron sequence is in italics);

cttcctggctagacctgcgcgcagtgcgca
(SEQ ID NO: 14; positions -12 to +18 of an
exemplary DUX4 intron 2-exon 3 boundary;
positions 12673-12702 of AF117653.2; the
intron sequence is in italics);

gcccgcttcctggctagacctgcgcgcagt
(SEQ ID NO: 15; positions -17 to +13 of an
exemplary DUX4 intron 2-exon 3 boundary;
positions 12668-12697 of AF117653.2; the intron
sequence is in italics).

acgcggggtttgggacggggtcgggt
(SEQ ID NO: 66; positions +7 to -18 of an
exemplary DUX4 exon 1-intron 1 boundary; positions
12105-12129 of AF117653.2; the intron sequence
is in italics).
```

For example, disclosed herein are anti-DUX4 antisense agents comprising, consisting essentially of or consisting of any one of sequences (e.g., nucleic acid sequences or nucleic acid analogue sequences) SEQ ID NO: 16 to 21, 64 or variants thereof having at least about 80% and preferably at least about 90% or at least about 95% sequence identity to the respective sequences, or fragments thereof comprising at least 10 bases, or at least 12 bases, preferably at least about 15 bases, more preferably at least about 20 bases, even more preferably at least about 25 bases, preferably wherein said reference to bases denotes consecutive bases, of the respective sequences or variants:

(SEQ ID NO: 16)
CUCUCACCGGGCCUAGACCUAGAAG;

(SEQ ID NO: 17)
UGCGCACUGCGCGCAGGUCUAGCCA;

(SEQ ID NO: 18)
ACUGCGCGCAGGUCUAGCCAGGAAG;

(SEQ ID NO: 19)
CGGGGUGCGCACUGCGCGCAGGUCU;

(SEQ ID NO: 20)
UGCGCACUGCGCGCAGGUCUAGCCAGGAAG;

(SEQ ID NO: 21)
ACUGCGCGCAGGUCUAGCCAGGAAGCGGGC;

(SEQ ID NO: 64)
ACCCGACCCCGUCCCAACCCCGCGU;

wherein U denotes uracil (which may be optionally replaced by thymine, T). In particular, the anti-DUX4 antisense agents comprising, consisting essentially of or consisting of any one of sequences SEQ ID NO: 16 to 21, 64 or the variants or fragments thereof display complementarity to, and are hence configured to bind to (anneal with), the above DUX4 sequences SEQ ID NO: 10 to 15, 66 or the variants or fragments thereof.

In an example, an anti-DUX4c antisense agent may be configured to bind to (anneal with) at least about 10 bases, preferably at least about 15 bases, more preferably at least about 20 bases, even more preferably at least about 25 bases or at least about 30 bases, such as to between about 10 and about 40 bases or to between about 20 and about 30 bases, preferably wherein said reference to bases denotes consecutive bases, of any one of the following DUX4c sequences (SEQ ID NO: 22 to 41) or of variants thereof having at least about 80% and preferably at least about 90% or at least about 95% sequence identity to the respective sequences:

```
acctccccacagcccacagctcttgtcata | gtgcgggaatagtgttctatcactacagga
(SEQ ID NO: 22; positions +30 to -30 of an exemplary
putative DUX4c exon 1-intron 1 boundary; positions 36-95 of
Genbank sequence NC_000004.11 range 190940254 . . . 190945505,
complement; the intron sequence is in italics);

agcccacagctcttgtcata | gtgcgggaatagtgttctat
(SEQ ID NO: 23; positions +20 to -20 of said
exemplary DUX4c exon 1-intron 1 boundary; the intron
sequence is in italics);

gcagagaggaaagcggtcttccgcctccag | ggccagcgggacctcgcactccgggaaaac
(SEQ ID NO: 24; positions -30 to +30 of an exemplary
putative DUX4c intron 1-exon 2 boundary; positions 587-646 of
NC_000004.11 range 190940254 . . . 190945505, complement; the
intron sequence is in italics);

aagcggtcttccgcctccag | ggccagcgggacctcgcact
(SEQ ID NO: 25; positions -20 to +20 of said
exemplary DUX4c intron 1-exon 2 boundary; the intron
sequence is in italics);

gctcaccagccctccggatcgccggcccgg | gtcacttcatcccggagcaattcggacgaa
(SEQ ID NO: 26; positions +30 to -30 of an exemplary putative
DUX4c exon 2-intron 2 boundary; positions 712-771 of
NC_000004.11 range 190940254 . . . 190945505, complement;
the intron sequence is in italics);

cctccggatcgccggcccgg | gtcacttcatcccggagcaa
(SEQ ID NO: 27; positions +20 to -20 of said
exemplary DUX4c exon 2-intron 2 boundary; the intron
sequence is in italics);

cgggttccacgctccttcgccctctgcaag | gggacctgttgctcgcgtgtctcccgcccc
(SEQ ID NO: 28; positions -30 to +30 of an exemplary
putative DUX4c intron 2-exon 3 boundary; positions 936-995 of
NC_000004.11 range 190940254..190945505, complement; the intron
sequence is in italics);

gctccttcgccctctgcaag | gggacctgttgctcgcgtgt
(SEQ ID NO: 29; positions -20 to +20 of said
exemplary DUX4c intron 2-exon 3 boundary; the intron
sequence is in italics);

ttgcaggaaacaggaatccgtggtcaggcc | gtgatgcaccgacgntcttttctctgca
(SEQ ID NO: 30; positions +30 to -30 of an exemplary
putative DUX4c exon 3-intron 3 boundary; positions 1131-1190 of
NC_000004.11 range 190940254.. 190945505, complement; the intron
sequence is in italics);
```

-continued caggaatccgtggtcaggcc | gtgatgcacccgacgtttct
(SEQ ID NO: 31; positions +20 to -20 of said
exemplary DUX4c exon 3-intron 3 boundary; the intron
sequence is in italics);

*agtcaagacagcggcttccagtttccat*ag | aattactggagaacctcagagagccagccc
(SEQ ID NO: 32; positions -30 to +30 of an exemplary
putative DUX4c intron 3-exon 4 boundary; positions 1355-1414 of
NC_000004.11 range 190940254 . . . 190945505, complement;
the intron sequence is in italics);

*gcggcttccagtttcccrt*ag | aattactggagaacctcaga
(SEQ ID NO: 33; positions -20 to +20 of said
exemplary DUX4c intron 3-exon 4 boundary; the intron
sequence is in italics);

gaagaacaccgggctctgctggaggagcag | *gt*tggagcggggttggggcggggtgggggc
(SEQ ID NO: 34; positions +30 to -30 of an exemplary
putative DUX4c exon 4-intron 4 boundary; positions 2916-2975 of
NC_000004.11 range 190940254 . . . 190945505, complement; the
intron sequence is in italics);

gggctctgctggaggagcag | *gt*tggagcggggttggggcg
(SEQ ID NO: 35; positions +20 to -20 of said
exemplary DUX4c exon 4-intron 4 boundary; the intron
sequence is in italics);

*ctggattccacgtttctttgccctctgc*ag | aggtgcctgttgctcaagtctctgccccg
(SEQ ID NO: 36; positions -30 to +30 of an exemplary
putative DUX4c intron 4-exon 5 boundary; positions 3404-4063 of
NC_000004.11 range 190940254 . . . 190945505, complement; the
intron sequence is in italics);

*cgtttctttgccctctgc*ag | aggtgcctgttgctcaagtc
(SEQ ID NO: 37; positions -20 to +20 of said exemplary
DUX4c intron 4-exon 5 boundary; the intron sequence
is in italics);

ttccaggaatgcgtggaacaccagcatcgt | *gt*cggtgctctcctttccagtttcaaacag
(SEQ ID NO: 38; positions +30 to -30 of an exemplary
putative DUX4c exon 5-intron 5 boundary; positions 4125-4184 of
NC_000004.11 range 190940254 . . . 190945505, complement;
the intron sequence is in italics);

gcgtggaacaccagcatcgt | *gt*cggtgctctcctttccag
(SEQ ID NO: 39; positions +20 to -20 of said
exemplary DUX4c exon 5-intron 5 boundary; the intron
sequence is in italics);

*ctgtcctcttggtgctgtgggtcctgaa*ag | ttgtcgagtgcgcccgtccctgtggtggga
(SEQ ID NO: 40; positions -30 to +30 of an exemplary putative
DUX4c intron 5-exon 6 boundary; positions 4881-4940 of
NC_000004.11 range 190940254 . . . 190945505, complement;
the intron sequence is in italics);

*ggtgctgtgggtcctgaa*ag | ttgtcgagtgcgcccgtccc
(SEQ ID NO: 41; positions -20 to +20 of said
exemplary DUX4c intron 5-exon 6 boundary; the intron
sequence is in italics).

Preferably, the anti-DUX4c antisense agent is capable of annealing over (i.e., span or cross) the respective exon-intron or intron-exon boundaries found in SEQ ID NO: 22 to 41 or in the variants thereof (indicated by the "1" symbol above). Also preferably, the anti-DUX4c antisense agent is capable of annealing with at least one and preferably both of the two intronic bases (indicated above in bold italics) adjacent to the respective exon-intron or intron-exon boundaries and/or (preferably "and") with at least one and preferably both of the two exonic bases (underlined above) adjacent to the respective exon-intron or intron-exon boundaries.

Without limitation, where a targeted sequence element is a polyadenylation signal in the DUX4 or DUX4c gene, such as preferably the polyadenylation signal ATTAAA, an antisense agent as disclosed herein may be configured to bind to a region in DUX4 or DUX4c sequence corresponding to positions about −30 to about +30, preferably about −25 to about +25, more preferably about −20 to about +20 relative to said polyadenylation signal (i.e., position −1 denoting the last base preceding the polyadenylation signal and position +1 denoting the first base following the polyadenylation signal). In particular, such antisense agent may be configured to bind to (anneal with) at least about 10 bases, preferably at least about 15 bases, more preferably at least about 20 bases, even more preferably at least about 25 bases or at least about 30 bases, such as to between about 10 and about 40 bases or to between about 20 and about 30 bases in any one of the above recited regions in the DUX4 or DUX4c sequence, wherein said reference to bases may preferably denote consecutive bases. Preferably, the antisense agent may be configured to bind such that it anneals with at least a portion of (e.g., 1, 2, 3, 4, 5 or 6 nucleotides) the polyadenylation signal or with the entire polyadenylation signal. For example but without limitation, such antisense agent may be configured to anneal over (i.e., to span or cross) the polyadenylation signal and to base pair with at least 1 base, preferably at least 2 bases, more preferably at least 5 bases and even more preferably at least 7 or at least 10 bases on each side of said polyadenylation signal, such as with between 1 and about 20 bases, preferably between 2 and about 15 bases or between 2 and about 10 bases on each side of said polyadenylation signal.

In an example, an anti-DUX4 antisense agent may be configured to bind to (anneal with) at least about 10 bases, preferably at least about 15 bases, more preferably at least about 20 bases, even more preferably at least about 25 bases or at least about 30 bases, such as to between about 10 and about 40 bases or to between about 20 and about 30 bases, preferably wherein said reference to bases denotes consecutive bases, of the following DUX4 sequences (SEQ ID NO: 67 or 68) or of variants thereof having at least about 80% and preferably at least about 90% or at least about 95% sequence identity to the respective sequences:

```
acatctcctggatgattagttcagagatatattaaa atgccccctccctgtggatcctatagaaga
(SEQ ID NO: 67; positions -30 to +30
of an exemplary DUX4 polyadenylation signal;
the polyadenylation signal is in italics);

gatgattagttcagagatatattaaaatgccccctc
cctgtggatc
(SEQ ID NO: 68; positions -20 to +20
of an exemplary DUX4 polyadenylation signal;
the polyadenylation signal is in italics);
```

Preferably, the anti-DUX4 antisense agent may be capable of annealing over (i.e., span or cross) the polyadenylation signal ATTAAA found in SEQ ID NO: 67 or 68 or in the variants thereof.

In non-limiting embodiments, an effective anti-DUX4 antisense agent may be configured to bind to (anneal with) the following DUX4 sequence (SEQ ID NO: 69) or to variants thereof having at least about 80% and preferably at least about 90% or at least about 95% sequence identity to said sequence, or to fragments thereof comprising at least 10 bases, or at least 12 bases, preferably at least about 15 bases, more preferably at least about 20 bases, even more preferably at least about 25 bases, preferably wherein said reference to bases denotes consecutive bases, of said sequence or variants. More specifically, such an anti-DUX4 antisense agent may comprise, consist essentially of or consist of a sequence (e.g., a nucleic acid sequence or nucleic acid analogue sequence) complementary to said DUX4 sequences SEQ ID NO: 69 or to variants thereof having at least about 80% and preferably at least about 90% or at least about 95% sequence identity to said sequence, or to fragments thereof comprising at least 10 bases, or at least 12 bases, preferably at least about 15 bases, more preferably at least about 20 bases, even more preferably at least about 25 bases, preferably wherein said reference to bases denotes consecutive bases, of the respective sequences or variants: agttcagagatatattaaaatgccc (SEQ ID NO: 69; positions −13 to +6 of an exemplary DUX4 polyadenylation signal; positions 12839-12863 of Genbank sequence AF117653.2 (see FIG. 3); the polyadenylation signal is in italics);

For example, disclosed herein is an anti-DUX4 antisense agents comprising, consisting essentially of or consisting of sequence (e.g., nucleic acid sequences or nucleic acid analogue sequences) SEQ ID NO: 65 or variants thereof having at least about 80% and preferably at least about 90% or at least about 95% sequence identity to said sequence, or fragments thereof comprising at least 10 bases, or at least 12 bases, preferably at least about 15 bases, more preferably at least about 20 bases, even more preferably at least about 25 bases, preferably wherein said reference to bases denotes consecutive bases, of said sequence or variants:

```
                                    (SEQ ID NO: 65)
GGGCAUUUUAAUAUAUCUCUGAACU
``` wherein U denotes uracil (which may be optionally replaced by thymine, T). In particular, the anti-DUX4 antisense agents comprising, consisting essentially of or consisting of any one of sequence SEQ ID NO: 65 or the variants or fragments thereof display complementarity to, and are hence configured to bind to (anneal with), the above DUX4 sequences SEQ ID NO: 69 or the variants or fragments thereof.

In a further aspect the invention provides an RNA interference (RNAi) agent capable of reducing or abolishing the production of DUX4 and/or DUX4c proteins.

In particular, the RNAi agent may be configured to target DUX4 and/or DUX4c messenger RNA (mRNA), respectively. Whereas the RNAi agent may be configured to target any part of DUX4 and/or DUX4c mRNA, such as for example the 5'-untranslated region (5' UTR), ORF or 3' UTR thereof, the RNAi agent may be preferably configured to target the 3' UTR of DUX4 and/or DUX4c mRNA. The inventors realised that targeting the 3' UTR of DUX4 and/or DUX4c mRNA allows for particularly effective RNAi-mediated downregulation of the production of DUX4 and/or DUX4c proteins. Moreover, targeting the 3' UTR of DUX4 or DUX4c mRNA allows for RNAi agents which are highly specific for either DUX4 or DUX4c mRNA, presumably but without limitation due to sequence differences in the distinct 3' UTRs.

DUX4 emerges as particularly implicated in the aetiology of FSHD. Hence, preferably disclosed herein is an RNAi agent capable of reducing or abolishing the production of DUX4 protein. Such RNAi agent is configured to target DUX4 mRNA.

Also preferably disclosed herein is an RNAi agent capable of reducing or abolishing the production of DUX4 protein but not of the DUX4c protein. Such RNAi agent is configured to target DUX4 mRNA but not DUX4c mRNA. In an alternative, disclosed is an RNAi agent capable of reducing or abolishing the production of DUX4c protein but not of the DUX4 protein. Such RNAi agent is configured to target DUX4c mRNA but not DUX4 mRNA.

RNAi agents as intended herein may particularly comprise or denote (i.e., may be selected from a group comprising or consisting of) RNAi nucleic acid molecules or RNAi nucleic acid analogue molecules, such as preferably short interfering nucleic acids and short interfering nucleic acid analogues (siNA) such as short interfering RNA and short interfering RNA analogues (siRNA), and may further denote inter alia double-stranded RNA and double-stranded RNA analogues (dsRNA), micro-RNA and micro-RNA analogues (miRNA), and short hairpin RNA and short hairpin RNA analogues (shRNA).

Advantageously, an RNAi agent as disclosed herein may be conjugated to a cell penetrating peptide (CPP), to enhance the cellular uptake of said RNAi agents.

An RNAi agent typically includes a double stranded portion (notwithstanding the optional and potentially preferred presence of any single-stranded overhands) comprising at least 16 bases, preferably at least 17 bases, more preferably at least 18 bases and still more preferably at least 19 bases, and usually between 18 and 35 bases, preferably between 19 and 30 bases, more preferably between 20 and 25 bases and even more preferably between 21 and 23 bases which are identical or almost identical to (e.g., showing 90% or more, e.g., at least 95%, sequence identity to, or showing maximum 2 and preferably only 1 mismatch with) an mRNA whose silencing is desired and which is thus targeted by said RNAi agent (such as, e.g., DUX4 and/or DUX4c mRNAs).

A DUX4 gene preferably intended for targeting by the RNAi agents as disclosed herein resides in the distal-most D4Z4 unit which extends into the pLAM region flanking the telomeric side of the D4Z4 array. Such DUX4 gene leads to production of comparably stable mRNA(s) (Dixit et al. 2007, supra). As schematically illustrated in FIG. 2 with reference to an exemplary but non-limiting genomic sequence as shown in FIG. 3, such DUX4 gene comprises two introns which are located in its 3' UTR, namely intron 1 (or intron A) within the D4Z4 unit and intron 2 (or intron B) provided by the pLAM region. Alternative splicing of intron 1 as schematically captured in FIG. 2 leads to alternative DUX4 mRNAs.

Exemplary but non-limiting DUX4 cDNA sequences including or not intron 1 are shown in FIGS. 4 (SEQ ID NO: 42) and 5 (SEQ ID NO: 43), respectively.

Accordingly, in an embodiment anti-DUX4 RNAi agents as intended herein may be configured to target DUX4 mRNA as represented by the DUX4 cDNA sequence set forth in SEQ ID NO: 42 or variants thereof having at least about 80% and preferably at least about 90% or at least about 95% sequence identity to SEQ ID NO: 42. Preferably, such anti-DUX4 RNAi agents may be configured to target the 3' UTR of said DUX4 mRNA or variants, such as for example to target 3' UTR sequences corresponding to or overlapping with exon 1, intron 1, exon 2 and/or exon 3.

In another embodiment anti-DUX4 RNAi agents as intended herein may be configured to target DUX4 mRNA as represented by the DUX4 cDNA sequence set forth in SEQ ID NO: 43 or variants thereof having at least about 80% and preferably at least about 90% or at least about 95% sequence identity to SEQ ID NO: 43. Preferably, such anti-DUX4 RNAi agents may be configured to target the 3' UTR of said DUX4 mRNA or variants, such as for example to target 3' UTR sequences corresponding to or overlapping with exon 1, exon 2 and/or exon 3.

In an example, an anti-DUX4 RNAi agent may be configured to target any one of the following DUX4 mRNA sequences (SEQ ID NO: 44 to 46) or variants thereof having at least about 80% and preferably at least about 90% or at least about 95% sequence identity to the respective sequences, or fragments thereof comprising at least 16 bases, preferably at least 17 bases, more preferably at least 18 bases and still more preferably at least 19 bases, and usually between 18 and 35 bases, preferably between 19 and 30 bases, more preferably between 20 and 25 bases and even more preferably between 21 and 23 bases, preferably wherein said reference to bases denotes consecutive bases, of the respective sequences or variants:

```
                                          (SEQ ID NO: 44)
CGCGGGGAACACCUGGCUGGCUACGGAGGGGCGUG (SEQ ID NO: 45)
GCCUUCUAGGUCUAGGCCCGGUGAGAGACUCCACA (SEQ ID NO: 46)
UAGGCAAACCUGGAUUAGAGUUACAUCUCCUGGAU
``` wherein U denotes uracil (which may be optionally replaced by thymine, T).

In exemplary but non-limiting embodiments, an anti-DUX4 RNAi agent as disclosed herein may comprise any one of the following sequences (SEQ ID NO: 47 to 49) or variants thereof having at least about 80% and preferably at least about 90% or at least about 95% sequence identity to (e.g., variants showing maximum 2 and preferably only 1 mismatch with) the respective sequences, or fragments thereof comprising at least 16 bases, preferably at least 17 bases and more preferably at least 18 bases, preferably wherein said reference to bases denotes consecutive bases, of the respective sequences or variants:

```
                                          (SEQ ID NO: 47)
         acaccuggcuggcuacgga;

(SEQ ID NO: 48)
         ggucuaggcccggugagag;

(SEQ ID NO: 49)
         ccuggauuagaguuacauc.
``` wherein U denotes uracil (which may be optionally replaced by thymine, T).

Exemplary but non-limiting DUX4c cDNA sequences are shown in FIGS. 6 (SEQ ID NO: 50) and 7 (SEQ ID NO: 51), including 3' UTR regions of distinct lengths.

Accordingly, in an embodiment anti-DUX4c RNAi agents as intended herein may be configured to target DUX4c mRNA as represented by the DUX4c cDNA sequence set forth in SEQ ID NO: 50 or variants thereof having at least about 80% and preferably at least about 90% or at least about 95% sequence identity to SEQ ID NO: 50. Preferably, such anti-DUX4c RNAi agents may be configured to target the 3' UTR of said DUX4c mRNA or variants.

In another embodiment anti-DUX4c RNAi agents as intended herein may be configured to target DUX4c mRNA as represented by the DUX4c cDNA sequence set forth in SEQ ID NO: 51 or variants thereof having at least about 80% and preferably at least about 90% or at least about 95% sequence identity to SEQ ID NO: 51. Preferably, such anti-DUX4c RNAi agents may be configured to target the 3' UTR of said DUX4c mRNA or variants.

As noted above, a further exemplary but non-limiting genomic sequence of the DUX4c gene (Genbank accession no. NC_000004 range 190940254 . . . 190945505, complement, sequence version 11, i.e., NC_000004.11 range 190940254 . . . 190945505, complement) predicts a longer DUX4c mRNA than those shown in FIGS. 6 and 7. In particular, such further exemplary but non-limiting DUX4c cDNA sequence is available in the Genbank database under accession no. XR_041199 (sequences version 2, i.e., XR_041199.2) and reproduced in FIG. 8 (SEQ ID NO: 52).

Hence, in an embodiment anti-DUX4c RNAi agents as intended herein may be configured to target DUX4c mRNA as represented by the DUX4c cDNA sequence set forth in SEQ ID NO: 52 or variants thereof having at least about 80% and preferably at least about 90% or at least about 95% sequence identity to SEQ ID NO: 52. Preferably, such anti-DUX4c RNAi agents may be configured to target the 3' UTR of said DUX4c mRNA or variants.

In an example, an anti-DUX4c RNAi agent may be configured to target any one of the following DUX4c mRNA sequences (SEQ ID NO: 53 to 55) or variants thereof having at least about 80% and preferably at least about 90% or at least about 95% sequence identity to the respective sequences, or fragments thereof comprising at least 16 bases, preferably at least 17 bases, more preferably at least 18 bases and still more preferably at least 19 bases, and usually between 18 and 35 bases, preferably between 19 and 30 bases, more preferably between 20 and 25 bases and even more preferably between 21 and 23 bases, preferably wherein said reference to bases denotes consecutive bases, of the respective sequences or variants:

```
                                         (SEQ ID NO: 53)
uguagacaccagaguuucagcaaaaggcacgaccu (SEQ ID NO: 54)
cacacagaggagggcugucauucuuuccugagcau (SEQ ID NO: 55)
uuucccagcguucuucagucgaguuggcggagac
``` wherein U denotes uracil (which may be optionally replaced by thymine, T).

In exemplary but non-limiting embodiments, an anti-DUX4c RNAi agent as disclosed herein may comprise any one of the following sequences (SEQ ID NO: 56 to 58) or variants thereof having at least about 80% and preferably at least about 90% or at least about 95% sequence identity to (e.g., variants showing maximum 2 and preferably only 1 mismatch with) the respective sequences, or fragments thereof comprising at least 16 bases, preferably at least 17 bases and more preferably at least 18 bases, preferably wherein said reference to bases denotes consecutive bases, of the respective sequences or variants:

```
                                         (SEQ ID NO: 56)
ccagaguuucagcaaaagg;

(SEQ ID NO: 57)
ggagggcugucauucuuuc;

(SEQ ID NO: 58)
gcguucuucagucgaguug;
``` wherein U denotes uracil (which may be optionally replaced by thymine, T).

Also disclosed herein is a method for producing any one anti-DUX4 and/or anti-DUX4c antisense agent or RNAi agent as taught herein, particularly wherein said agent comprises, consists essentially of or consists of a nucleic acid molecule or a nucleic acid analogue molecule, comprising synthesising said agent from its constituent nucleotides or nucleotide analogues, and optionally and preferably at least partly purifying the agent from the synthesis reaction.

Further disclosed herein is a nucleic acid, more specifically an isolated nucleic acid, encoding any one or more anti-DUX4 and/or anti-DUX4c antisense agent or RNAi agent as taught herein. Preferably, the nucleic acid may be operably linked to one or more regulatory sequences allowing for expression of the nucleic acid in an expression system, such as without limitation in vitro (e.g., in a cell-free expression system) or in a host cell or host organism.

As well disclosed is a recombinant nucleic acid construct (i.e., a vector) comprising a nucleic acid encoding any one or more anti-DUX4 and/or anti-DUX4c antisense agent or RNAi agent as taught herein. Such construct (vector) may allow inter alia to propagate the nucleic acid encoding said agent, e.g., in vitro or in a host cell or host organism. Also contemplated is a method for producing said recombinant nucleic acid construct (vector) comprising introducing the nucleic acid encoding said agent to a recipient nucleic acid construct (recipient vector).

Preferably, the recombinant nucleic acid construct may be an expression construct (i.e., an expression vector), hence may be capable of expressing (configured to express) the nucleic acid encoding the one or more anti-DUX4 and/or anti-DUX4c antisense agent or RNAi agent in an expression system, such as without limitation in vitro (e.g., in a cell-free expression system) or in a host cell or host organism. In an expression construct (expression vector), the nucleic acid encoding said agent is operably linked to one or more regulatory sequences allowing for expression of the nucleic acid in said expression system. Also contemplated is thus a method for producing said expression construct (expression vector) comprising introducing the nucleic acid encoding said agent to a recipient expression construct (recipient expression vector).

Also disclosed is thus a method for producing any one or more anti-DUX4 and/or anti-DUX4c antisense agent or RNAi agent as taught herein comprising expressing said agent from an expression construct (expression vector) as taught herein comprising a nucleic acid encoding said agent, in an expression system, and optionally at least partly purifying the agent.

Disclosed herein is as well a host cell comprising any one or more anti-DUX4 and/or anti-DUX4c antisense agent or RNAi agent, or an isolated nucleic acid encoding such an agent, or a recombinant construct (vector) (preferably an expression construct, expression vector) comprising a nucleic acid encoding such an agent, as taught herein. Also encompassed is a method for producing such a host cell comprising introducing into a recipient host cell the anti-DUX4 and/or anti-DUX4c antisense agent or RNAi agent, or the isolated nucleic acid encoding such an agent, or the recombinant construct (vector) (preferably an expression construct, expression vector) comprising a nucleic acid encoding such an agent. Preferably, the host cell may be a prokaryotic or eukaryotic cell, more preferably a bacterial, fungal, plant or animal cell, even more preferably a mammal cell or a primate cell, including very preferably human cells, as well as non-human mammal cells and non-human primate cells. For example, said human host cell may be a myoblast or a myoblast precursor derived from a patient, such as for example a myoblast derived from a muscle biopsy of said patient or derived from a mesangioblast of said patient, or said myoblast or myoblast precursor may be differentiated from an adult stem cell or an induced pluripotent stem (iPS) cell of said patient. The isolated nucleic acid or construct (vector) may be integrated, preferably stably integrated, into the genome of the host cell or may remain extra-genomic or extra-chromosomal. Insofar the host cell comprises said agent, isolated nucleic acid or construct (vector), it may be denoted a 'transgenic' or 'transformed' cell in that regard. Preferably, a host cell expresses or is under suitable conditions capable of expressing the isolated nucleic acid or vector comprised therein, thereby producing the anti-DUX4 and/or anti-DUX4c antisense agent or RNAi agent encoded thereby. Also contemplated is thus a method for producing any one or more anti-DUX4 and/or anti-DUX4c antisense agent or RNAi agent as taught herein comprising culturing or maintaining a host cell comprising an isolated nucleic acid encoding said agent or an expression construct (expression vector) comprising a nucleic acid encoding said agent, under conditions conducive to expression of said agent from said isolated nucleic acid or expression construct. The so-produced agent may be intended to exert its silencing effect in the host cell expressing it, or may by intended for use elsewhere in which case the method may further optionally and preferably comprise at least partly purifying the agent.

Disclosed herein is as well a host organism comprising any one or more anti-DUX4 and/or anti-DUX4c antisense agent or RNAi agent, or an isolated nucleic acid encoding such an agent, or a recombinant construct (vector) (preferably an expression construct, expression vector) comprising a nucleic acid encoding such an agent, or a host cell, as taught herein. Also encompassed is a method for producing such a host organism comprising introducing the anti-DUX4 and/or anti-DUX4c antisense agent or RNAi agent, or the isolated nucleic acid encoding such an agent, or the recombinant construct (vector) (preferably an expression construct, expression vector) comprising a nucleic acid encoding such an agent, into a recipient host organism, e.g., to a cell, tissue or organ of said host organism, or introducing the host cell as taught herein to a recipient host organism, or at least partly regenerating an organism from said host cell. Preferably, the host organism may be a multi-cellular organism, more preferably a plant or animal organism, even more preferably a mammal or primate, particularly including non-human mammals and non-human primates. The isolated nucleic acid or construct (vector) may be integrated, preferably stably integrated, into the genome of the host organism or may remain extra-genomic or extra-chromosomal. Insofar the host organism comprises said agent, isolated nucleic acid or construct (vector), it may be denoted a 'transgenic' or 'transformed' organism in that regard. Preferably, a host organism expresses or is under suitable conditions capable of expressing the isolated nucleic acid or vector comprised therein, thereby producing the anti-DUX4 and/or anti-DUX4c antisense agent or RNAi agent encoded thereby. Also contemplated is thus a method for producing any one or more anti-DUX4 and/or anti-DUX4c antisense agent or RNAi agent as taught herein comprising culturing or maintaining a host organism comprising an isolated nucleic acid encoding said agent or an expression construct (expression vector) comprising a nucleic acid encoding said agent, under conditions conducive to expression of said agent from said isolated nucleic acid or expression construct. The so-produced agent may be intended to exert its silencing effect in the host organism expressing it, or may by intended for use elsewhere in which case the method may further optionally and preferably comprise at least partly purifying the agent.

As well encompassed is a progeny of the host cell or host organism as taught herein. Particularly intended is progeny comprising the introduced agent, or isolated nucleic acid encoding the agent, or a construct (vector) comprising a nucleic acid encoding the agent, or comprising a replicated copy of said nucleic acid or construct (vector), i.e., progeny transgenic or transformed with regard to said nucleic acid or construct.

Also intended are compositions and formulations comprising any one or more anti-DUX4 and/or anti-DUX4c antisense agent or RNAi agent as taught herein, or an isolated nucleic acid encoding such an agent, a recombinant construct (vector) (preferably an expression construct, expression vector) comprising a nucleic acid encoding such an agent, or a host cell or host organism as taught herein, and one or more additional components, such as without limitation one or more solvents and/or one or more pharmaceutically acceptable carriers. Further provided are methods for producing the above compositions or formulations, comprising admixing said agent, isolated nucleic acid, construct (vector), host cell or host organism as taught herein with one or more additional components.

Particularly intended are pharmaceutical compositions and formulations comprising any one or more anti-DUX4 and/or anti-DUX4c antisense agent or RNAi agent as taught herein, or an isolated nucleic acid encoding such an agent, a recombinant construct (vector) (preferably an expression construct, expression vector) comprising a nucleic acid encoding such an agent, or a host cell or host organism as taught herein, one or more pharmaceutically acceptable carriers; and methods for producing said pharmaceutical compositions and formulations, comprising admixing said agent, isolated nucleic acid, construct (vector), host cell or host organism as taught herein with said one or more pharmaceutically acceptable carriers.

Further disclosed herein are kits of parts comprising any one or more anti-DUX4 and/or anti-DUX4c antisense agent or RNAi agent as taught herein, or an isolated nucleic acid encoding such an agent, a recombinant construct (vector) (preferably an expression construct, expression vector) comprising a nucleic acid encoding such an agent, or a host cell or host organism or progeny thereof as taught herein, or composition(s) or formulation(s) comprising any of such. The components of the kits may be in various forms, such as, e.g., lyophilised, free in solution or immobilised on a solid phase. They may be, e.g., provided in a multi-well plate or as an array or microarray, or they may be packaged separately and/or individually. A kit will further typically comprise instructions for its use. The kits may be advantageously employed in various applications, such as inter alia in therapeutic, diagnostic, compound-screening and research applications.

Further provided is:
  any one or more anti-DUX4 and/or anti-DUX4c antisense agent or RNAi agent as taught herein, or an isolated nucleic acid encoding such an agent, a recombinant construct (vector) (preferably an expression construct, expression vector) comprising a nucleic acid encoding such an agent, or a host cell or host organism or progeny thereof as taught herein, or composition(s) or formulation(s) comprising any of such, for use as a medicament; or for use in the treatment of a disease or condition the treatment of which can benefit from reducing the expression of double homeobox 4 and/or double homeobox 4c;
  use of any one or more anti-DUX4 and/or anti-DUX4c antisense agent or RNAi agent as taught herein, or an isolated nucleic acid encoding such an agent, a recombinant construct (vector) (preferably an expression construct, expression vector) comprising a nucleic acid encoding such an agent, or a host cell or host organism or progeny thereof as taught herein, or composition(s) or formulation(s) comprising any of such, for the manufacture of a medicament for the treatment of a disease or condition the treatment of which can benefit from reducing the expression of double homeobox 4 and/or double homeobox 4c; or
  a method for treating a disease or condition the treatment of which can benefit from reducing the expression of double homeobox 4 and/or double homeobox 4c in a subject, comprising administering to said subject a therapeutically or prophylactically effective amount of any one or more anti-DUX4 and/or anti-DUX4c antisense agent or RNAi agent as taught herein, or an isolated nucleic acid encoding such an agent, a recombinant construct (vector) (preferably an expression construct, expression vector) comprising a nucleic acid encoding such an agent, or a host cell or host organism or progeny thereof as taught herein, or composition(s) or formulation(s) comprising any of such.

Preferably, the diseases or conditions include ones comprising increased levels and/or increased activity of double homeobox 4 and/or double homeobox 4c, more preferably the disease or condition is facioscapulohumeral muscular dystrophy (FSHD). Double homeobox 4 emerges as particularly implicated in the aetiology of FSHD. Anti-DUX4 antisense and/or RNAi agents and the related or derived reagents are thus preferred.

It shall be appreciated that the reference herein to "any one or more anti-DUX4 and/or anti-DUX4c antisense agent or RNAi agent" covers not only such single agents, but also any combinations of two or more such agents. Expressly intended are without limitation a combination of two or more anti-DUX4 and/or anti-DUX4c antisense agents; a combination of two or more anti-DUX4 and/or anti-DUX4c RNAi agents; and a combination of one or more anti-DUX4 and/or anti-DUX4c antisense agent and one or more anti-DUX4 and/or anti-DUX4c RNAi agent. Agents in a combination of two or more agents may be typically provided as separate molecules, or may otherwise be covalently or non-covalently conjugated to one another, either directly or via a suitable linker or carrier. A non-limiting example of joined agents includes "weasel" agents of two or more co-joined antisense oligonucleotides as disclosed in WO 2006/000057, or in Aartsma-Rus et al. 2004 (Am J Hum Genet 74: 83-92).

The above and further aspects and preferred embodiments of the invention are described in the following sections and in the appended claims. The subject matter of appended claims 1 to 28 is hereby specifically incorporated in this specification.

BRIEF DESCRIPTION OF THE FIGURES

FIG. 3 illustrates the sequence (SEQ ID NO: 1) of an exemplary genomic fragment as schematically set out in FIG. 2, encompassing the 3' portion of the DUX4 ORF and its 3' UTR. This particular sequence reproduces positions 12001 to 13080 of the genomic sequence available in the NCBI Genbank database under accession number AF117653 (sequence version no. 2, i.e., AF117653.2). In this AF117653 sequence said DUX4 ORF extends from an ATG translation initiation codon at position 10829 (not shown) to the stop codon at positions 12101-12103 (boxed). Exon 1 ends at position 12111, intron 1 extends from position 12112 to 12247 within the D4Z4 unit (italics), exon 2 extends from position 12248 to 12329 (bold), the last D4Z4 unit ends at position 12329 continuing with the pLAM region, intron 2 extends from position 12330 to 12684 (larger) (italics) or alternatively 12338-12682 (smaller), and exon 3 extends from position 12685 to 12873 (bold).

FIG. 4 illustrates the sequence (SEQ ID NO: 42) of an exemplary DUX4 cDNA. The DUX4 ORF, demarcated by the translation initiation codon (bold, boxed) and the stop codon (boxed), and the 5' UTR upstream of the ATG codon correspond to these portions in the exemplary DUX4 cDNA sequence available in Genbank under accession no. NM_033178 (sequence version 2, i.e., NM_033178.2). The 3' UTR downstream of the stop codon (i.e., starting from position 1576 of SEQ ID NO: 42) is compiled from the DUX4 genomic sequence AF117653.2 (see FIG. 3 and legend thereto) and includes the remainder of exon 1, intron 1 (italics), exon 2 (bold) and exon 3 (underlined).

FIG. 5 illustrates the sequence (SEQ ID NO: 43) of an exemplary DUX4 cDNA. The DUX4 ORF, demarcated by the translation initiation codon (bold, boxed) and the stop codon (boxed), and the 5' UTR upstream of the ATG codon correspond to these portions in the exemplary DUX4 cDNA sequence available in Genbank under accession no. NM_033178 (sequence version 2, i.e., NM_033178.2). The 3' UTR downstream of the stop codon (i.e., starting from position 1576 of SEQ ID NO: 43) is compiled from the DUX4 genomic sequence AF117653.2 (see FIG. 3 and legend thereto) and includes the remainder of exon 1, exon 2 (bold) and exon 3 (underlined).

FIG. 6 illustrates the sequence (SEQ ID NO: 50) of an exemplary putative DUX4c cDNA. This sequence corresponds to positions 727 to 2440 of an exemplary but non-limiting genomic sequence of the DUX4c gene (Genbank accession no. AY500824, sequence version 1, i.e., AY500824.1). Indicated are the putative GC-box (underlined) at positions 1-13 of SEQ ID NO: 50 (positions 727-739 of AY500824.1), the putative TATA-box variant (double underlined) at positions 48-52 of SEQ ID NO: 50 (positions 774-778 of AY500824.1), the DUX4c ORF demarcated by the translation initiation codon (bold, boxed) at positions 192-194 of SEQ ID NO: 50 (positions 918-920 of AY500824.1) and the stop codon (boxed) at positions 1314-1316 of SEQ ID NO: 50 (positions 2040-2042 of AY500824.1). The 3' UTR as experimentally detected extends downstream of the stop codon (i.e., starting from position 1317 of SEQ ID NO: 50; position 2043 of AY500824.1) down to position 1714 of SEQ ID NO: 50 (position 2440 of AY500824.1).

FIG. 7 illustrates the sequence (SEQ ID NO: 51) of an exemplary putative DUX4c cDNA. This sequence corresponds to positions 727 to 2629 of an exemplary but non-limiting genomic sequence of the DUX4c gene (Genbank accession no. AY500824, sequence version 1, i.e., AY500824.1). Indicated are the putative GC-box (underlined) at positions 1-13 of SEQ ID NO: 51 (positions 727-739 of AY500824.1), the putative TATA-box variant (double underlined) at positions 48-52 of SEQ ID NO: 51 (positions 774-778 of AY500824.1), the DUX4c ORF demarcated by the translation initiation codon (bold, boxed) at positions 192-194 of SEQ ID NO: 51 (positions 918-920 of AY500824.1) and the stop codon (boxed) at positions 1314-1316 of SEQ ID NO: 51 (positions 2040-2042 of AY500824.1). The 3' UTR as experimentally detected in an FSHD patient extends downstream of the stop codon (i.e., starting from position 1317 of SEQ ID NO: 51; position 2043 of AY500824.1) down to position 1903 of SEQ ID NO: 51 (position 2629 of AY500824.1).

FIG. 8 illustrates the sequence (SEQ ID NO: 52) of an exemplary putative DUX4c cDNA. This sequence corresponds to predicted DUX4c mRNA as available in the Genbank database under accession no. XR_041199 (sequences version 2, i.e., XR_041199.2). Indicated are the DUX4c ORF demarcated by the translation initiation codon (bold, boxed) at positions 688-670 and the stop codon (boxed) at positions 1810-1812. The predicted 3' UTR extends downstream of the stop codon (i.e., starting from position 1813.

FIG. 20 illustrates an exemplary sequence of DUX4 protein.

FIG. 21 illustrates an exemplary sequence of DUX4c protein.

FIG. 27 illustrates exemplary genomic sequence of the DUX4 transcripts of FIG. 26. Snider et al. reported a different sequence for the beginning of the pLAM region that contains the intron 2 donor splicing site (boxed sequence GGTACC). Sequence comparison revealed that this sequence is identical to those in the beginning of a D4Z4 unit surrounding the intron 2a splice donor site (Coppée et al.).

FIG. 31 schematically shows the position of the antisense oligonucleotides 2245 and 2250 on the DUX4 genomic sequence fragment available in Genbank under accession no. AF117653 (sequence version 2, i.e., AF117653.2). (see FIG. 3 and legend thereto). This sequence fragment includes intron 1 (italics), exon 2 (bold), exon 3 (italics, bold) and the stop codon of the DUX4 ORF (boxed), antisense oligonucleotides 2245 (underlined) and 2250 (underlined, bold).

DETAILED DESCRIPTION OF THE INVENTION

Figure 1:
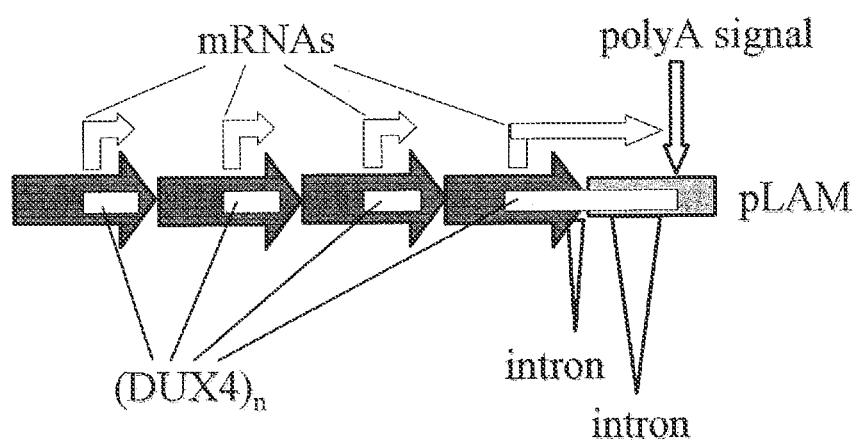
FIG. 1 illustrates a schematic representation of the DUX4 transcripts expressed from an exemplary pathogenic D4Z4 repeat array containing four D4Z4 units (grey arrows) at the 4q35 locus. Each of the four D4Z4 units contains the DUX4 open reading frame (ORF) (white boxes) and a transcription start site (white bended arrows). The repeat array is flanked on its telomeric end by the pLAM region (grey box) which is only present on the 4qA allele uniquely linked to FSHD. The alternative 4qB allele is not linked to FSHD (Lemmers et al. 2004 (Am J Hum Genet 75(6): 1124-30)).
Figure 2:
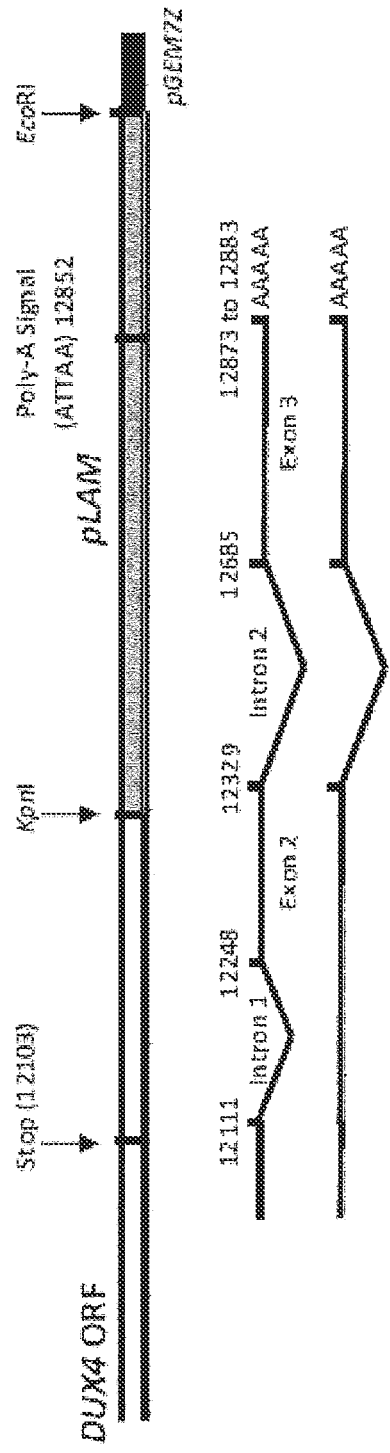
FIG. 2 illustrates a scheme of an EcoRI genomic fragment cloned in pGEM7Z and encompassing the 3'portion of the DUX4 ORF and its 3' UTR. The stop codon of the DUX4 ORF, the pLAM region and the poly-A addition signal (ATTAAA) are indicated in the upper panel. The lower panel captures the mapping of the 3' mRNA ends and illustrates the location of introns 1 and 2. Intron 1 is alternatively spliced. The nucleotide positions are as shown in the sequence in FIG. 3.

As used herein, the singular forms "a", "an", and "the" include both singular and plural referents unless the context clearly dictates otherwise.

The terms "comprising", "comprises" and "comprised of" as used herein are synonymous with "including", "includes"

or "containing", "contains", and are inclusive or open-ended and do not exclude additional, non-recited members, elements or method steps.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, term definitions may be included to better appreciate the teaching of the present invention.

For general methods relating to the invention, reference is made inter alia to well-known textbooks, including, e.g., "Molecular Cloning: A Laboratory Manual, 2nd Ed." (Sambrook et al., 1989), Animal Cell Culture (R. I. Freshney, ed., 1987), the series Methods in Enzymology (Academic Press), Gene Transfer Vectors for Mammalian Cells (J. M. Miller & M. P. Calos, eds., 1987); "Current Protocols in Molecular Biology and Short Protocols in Molecular Biology, 3rd Ed." (F. M. Ausubel et al., eds., 1987 & 1995); Recombinant DNA Methodology II (R. Wu ed., Academic Press 1995).

General techniques in cell culture and media uses are outlined inter alia in Large Scale Mammalian Cell Culture (Hu et al. 1997. Curr Opin Biotechnol 8: 148); Serum-free Media (K. Kitano. 1991. Biotechnology 17: 73); or Large Scale Mammalian Cell Culture (Curr Opin Biotechnol 2: 375, 1991).

As used herein, the terms "double homeobox 4" and "DUX4" are synonymous and refer to genes, gene products, nucleic acids, proteins and polypeptides commonly known under these designations in the art. The terms encompass such genes, gene products, nucleic acids, proteins and polypeptides of any organism where found, and particularly of animals, preferably vertebrates, more preferably mammals, including humans and non-human mammals, even more preferably of humans.

The terms particularly encompass such genes, gene products, nucleic acids, proteins and polypeptides with a native sequence, i.e., ones of which the primary sequence is the same as that of DUX4 found in or derived from nature. A skilled person understands that native sequences of DUX4 may differ between different species due to genetic divergence between such species. Moreover, the native sequences of DUX4 may differ between or within different individuals of the same species due to normal genetic diversity (genetic variation) or due to mutation within a given species. Also, the native sequences of DUX4 may differ between or even within different individuals of the same species due to post-transcriptional or post-translational modifications. Accordingly, all DUX4 sequences found in or derived from nature are considered "native".

The terms encompass DUX4 genes, gene products, nucleic acids, proteins and polypeptides when forming a part of a living organism, organ, tissue or cell, when forming a part of a biological sample, as well as when at least partly isolated from such sources. The terms also encompass genes, gene products, nucleic acids, proteins and polypeptides when produced by recombinant or synthetic means.

DUX4 gene as intended herein may particularly denote a DUX4 gene present in the distal-most unit of a D4Z4 array on chromosome 4q35, particularly wherein the DUX4 gene extends into the pLAM region flanking the telomeric side of the D4Z4 array, more particularly wherein said pLAM region provides a polyadenylation signal, such as preferably ATTAAA. Such DUX4 gene leads to production of comparably stable mRNA(s) (Dixit et al. 2007, supra).

Figure 26:
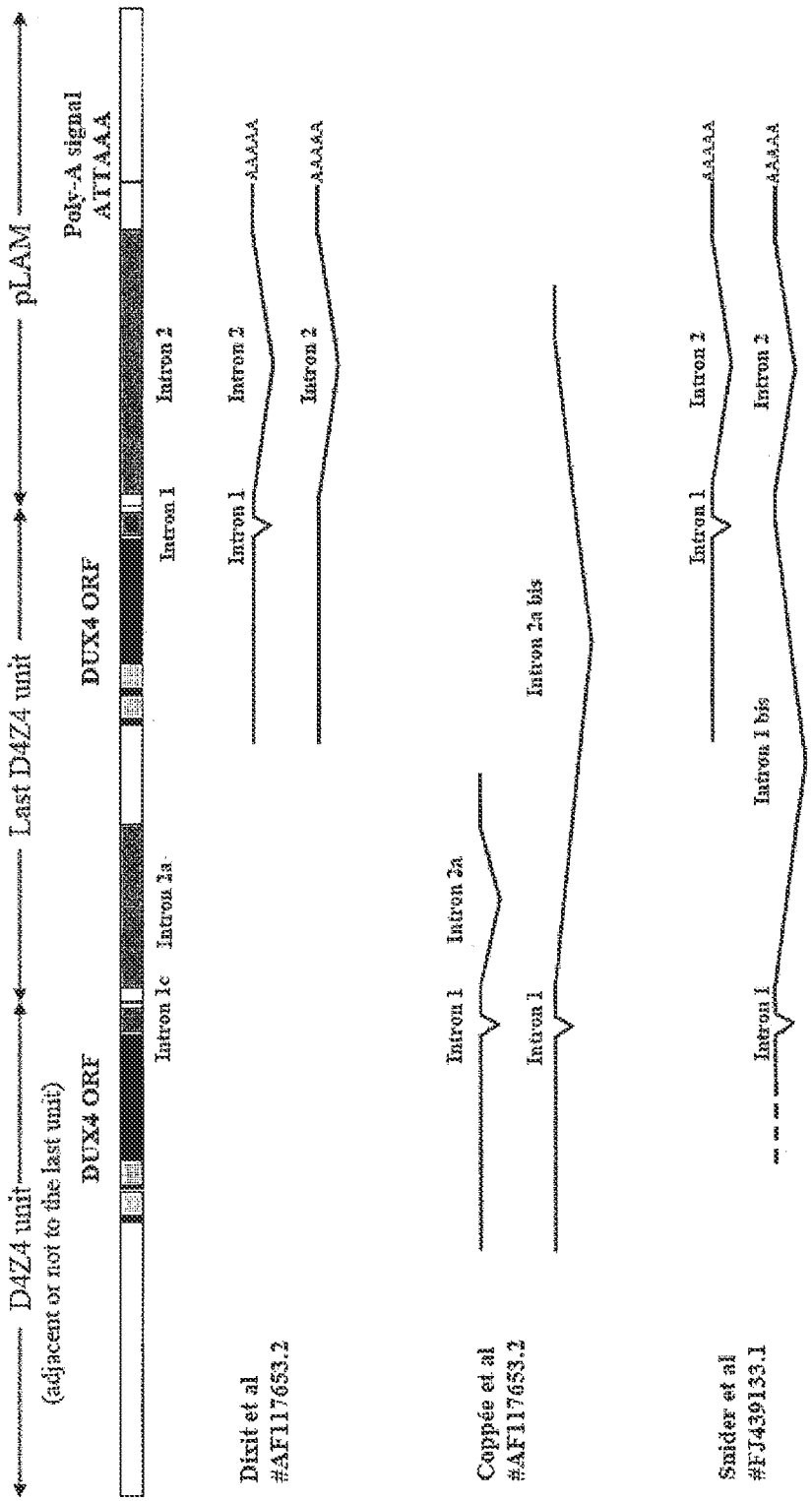
FIG. 26 illustrates exemplary transcripts derived from one or more D4Z4 units and comprising the pLAM region or not. The upper panel schematically shows genomic fragments of a D4Z4 unit and the pLAM region. The DUX4 ORF is represented in black with the two homeobox regions in grey. The positions of the different introns are indicated (dark grey boxes). The pLAM region encompasses an intron (dark grey box) and the poly-A signal (ATTAAA). The lower panels illustrate the location of introns 1, 2, 2a, 1 bis and 2a bis. The first transcript published (Dixit et al., supra) begins in the last D4Z4 unit with alternative splicing of intron 1 in the D4Z4 sequence, then extending into the pLAM region where intron 2 is always spliced out, and ending 6 to 16 bp after the poly-A signal. We found a second transcript (Coppée et al., unpublished) that begins in a D4Z4 unit (adjacent or not to the last unit) that has the same intron 1 as reported above. The transcript continues in the adjacent D4Z4 unit where another intron is found that is named either 2a if the splice acceptor site is in the D4Z4 unit or 2a bis if this splice acceptor site is in the pLAM region. No poly-A signals were reported at proximity Snider et al., supra found a DUX4 transcript corresponding to those described in Dixit et al. and a DUX4 transcript with 2 copies of exon 2.
Figure 28:
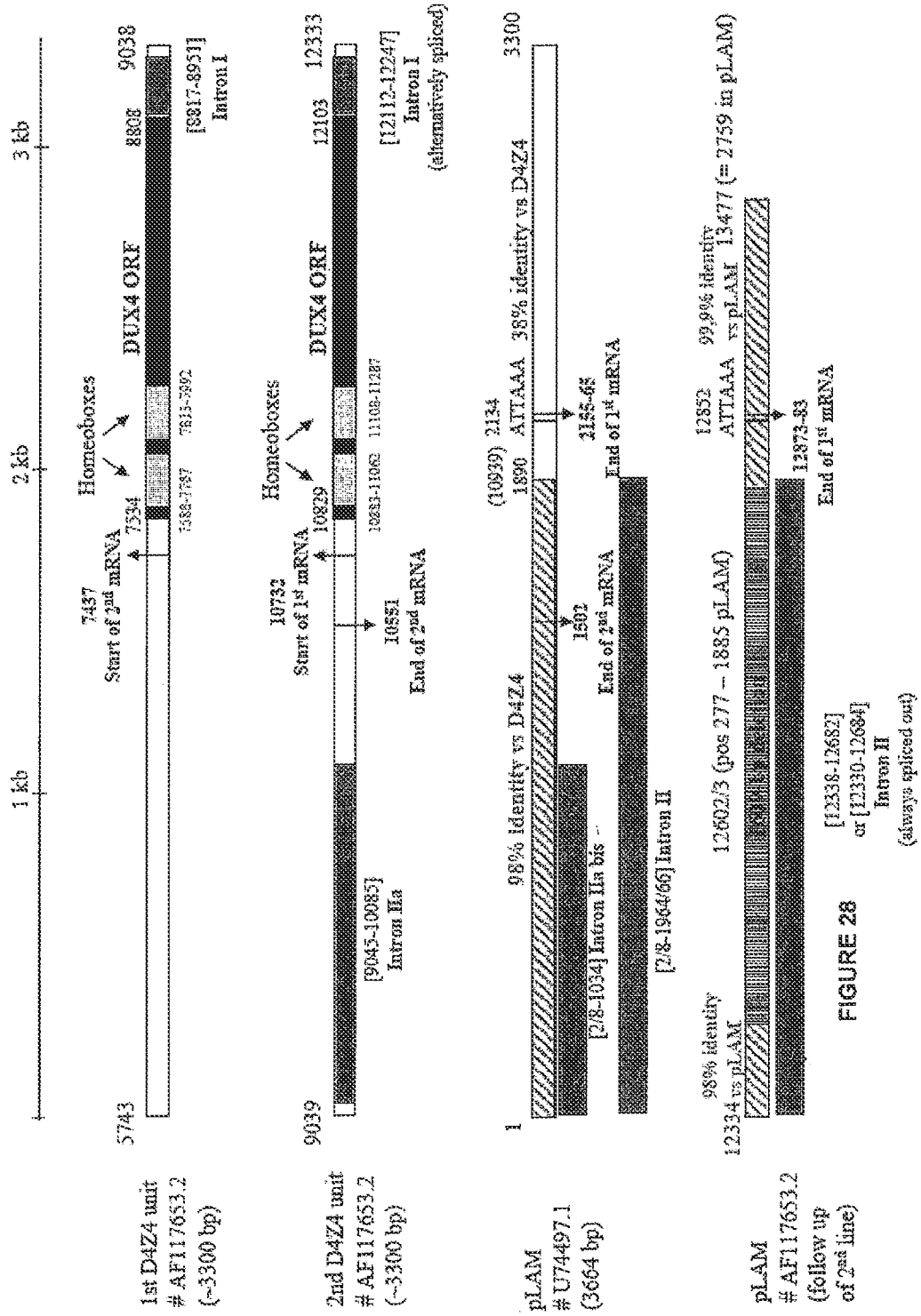
FIG. 28 schematically shows the DUX4 gene structure by aligning D4Z4 and pLAM variants. Two adjacent D4Z4 units are represented to scale from GenBank accession number AF117653.1 (first and second line) as well as the flanking pLAM region (fourth line). This region differs from that represented in the third line (GenBank accession number U74497.1) by a deletion of a 1609-bp segment (vertical stripes). This pLAM region (third line) is nearly identical to a D4Z4 unit over 1890 bp (grey stripes) and diverges in further distal sequences. The 1609-bp deletion in the pLAM region of the fourth line is found in the region nearly identical to D4Z4. The DUX4 ORF is represented in black with the two homeobox regions in grey. The positions of the different introns are indicated (dark grey boxes). The DUX4 mRNA start sites are indicated by black upward arrows for the 1" mRNA (Dixit et al. 2007) and the 2' mRNA (Coppée et al., unpublished). The DUX4 mRNA ends are indicated by black downwards arrows. Different ends were found: 6 to 16 bp downstream from the poly-A signal (Dixit et al., 2007) for the 1" mRNA, and two possible ends (either in D4Z4 or in pLAM) for the 2' mRNA.

While additional DUX4 transcripts have been identified that may span several D4Z4 units and may display alternative splicing, and preferably also comprise the pLAM region (Snider et al. 2009, supra; Coppée et al., unpublished), DUX4 gene as intended herein may also particularly denote such D4Z4-resident transcription units, particularly ones that give rise to a transcript leading to production of comparably stable mRNA comprising DUX4 sequences, even more particularly wherein the transcript comprises the pLAM region, still more particularly wherein said pLAM region provides a polyadenylation signal, such as preferably ATTAAA. Such DUX4 transcripts and mRNA are schematically illustrated in FIGS. 26 and 28 with reference to an exemplary but non-limiting genomic sequence as shown in FIG. 27.

It shall also be appreciated that the pLAM region may display polymorphisms, such as without limitation the presence or absence of a 1.6-kb sequence within its intron (Gabriéls et al. 1999, supra; van Deutekom et al. 2009, supra).

Even more particularly, DUX4 gene as intended herein denotes DUX4 gene as above as present in a pathogenic D4Z4 array associated with facioscapulohumeral muscular dystrophy (FSHD).

Exemplary DUX4 gene includes without limitation human DUX4 gene having nucleic acid sequence as annotated under NCBI Genbank (http://www.ncbi.nlm.nih.gov/) accession number AF117653 (sequence version no. 2 revised on Nov. 30, 2009, i.e., AF117653.2), more particularly the DUX4 gene at positions about 10650 to about 12873 of AF117653.2, also particularly at positions about 10829 to about 12873 of AF117653.2.

Exemplary but non-limiting DUX4 cDNA (and respective mRNA) includes without limitation human DUX4 cDNA having nucleic acid sequence as annotated under Genbank accession number NM_033178 (sequence version 2 revised on Feb. 28, 2010, i.e., NM_033178.2). Further exemplary but non-limiting DUX4 cDNA (and respective mRNA) include without limitation human DUX4 cDNA having nucleic acid sequence as set out in SEQ ID NO: 42 (FIG. 4) or SEQ ID NO: 43 (FIG. 5).

Exemplary DUX4 protein or polypeptide includes without limitation human DUX4 protein or polypeptide having primary amino acid sequence as annotated under Genbank accession no. NP_149418 (sequence version 3 revised on Feb. 28, 2010, i.e., NP_149418.3), also reproduced in FIG. 20 as SEQ ID NO: 59.

As used herein, the terms "double homeobox 4c" and "DUX4c" are synonymous and refer to genes, gene products, nucleic acids, proteins and polypeptides commonly known under these designations in the art. The terms encompass such genes, gene products, nucleic acids, proteins and polypeptides of any organism where found, and particularly of animals, preferably vertebrates, more preferably mammals, including humans and non-human mammals, even more preferably of humans.

The terms particularly encompass such genes, gene products, nucleic acids, proteins and polypeptides with a native sequence, i.e., ones of which the primary sequence is the same as that of DUX4c found in or derived from nature. A skilled person understands that native sequences of DUX4c may differ between different species due to genetic divergence between such species. Moreover, the native sequences of DUX4c may differ between or within different individuals of the same species due to normal genetic diversity (genetic variation) or due to mutation within a given species. Also, the native sequences of DUX4c may differ between or even within different individuals of the same species due to post-transcriptional or post-translational modifications. Accordingly, all DUX4c sequences found in or derived from nature are considered "native".

The terms encompass DUX4c genes, gene products, nucleic acids, proteins and polypeptides when forming a part of a living organism, organ, tissue or cell, when forming a part of a biological sample, as well as when at least partly isolated from such sources. The terms also encompass genes, gene products, nucleic acids, proteins and polypeptides when produced by recombinant or synthetic means.

Exemplary DUX4c gene includes without limitation human DUX4c gene having nucleic acid sequence as annotated under Genbank accession number AY500824 (sequence version 1 revised on Dec. 1, 2009, i.e., AY500824.1). A further exemplary DUX4c gene includes without limitation human DUX4c gene having nucleic acid sequence as annotated under Genbank accession number NC_000004 range 190940254 . . . 190945505, complement (sequence version 11 revised on Jun. 10, 2009, i.e., NC_000004.11).

Exemplary but non-limiting DUX4c cDNA (and respective mRNA) includes without limitation human DUX4c cDNA having nucleic acid sequence as set out in SEQ ID NO: 50 (FIG. 6) or SEQ ID NO: 51 (FIG. 7). A further exemplary but non-limiting DUX4c cDNA (and respective mRNA) includes without limitation human DUX4c cDNA having nucleic acid sequence as annotated under Genbank accession no. XR_041199 (sequences version 2 revised on Jun. 10, 2009, i.e., XR_041199.2) also reproduced in FIG. 8.

Exemplary DUX4c protein or polypeptide includes without limitation human DUX4c protein or polypeptide having primary amino acid sequence as annotated under Genbank accession no. AAS15569 (sequence version 1 revised on Dec. 1, 2009, i.e., AAS15569.1), also reproduced in FIG. 21 as SEQ ID NO: 60.

It shall be appreciated that other DUX genes homologous to DUX4 and/or DUX4c are present in and transcribed from the human genome but are not linked to FSHD. Consequently, antisense and siRNA agents as intended herein preferably target DUX4 and/or DUX4c genes specifically, i.e., substantially to the exclusion of other DUX genes. In particular, such specific agents may display adequate sequence identity to DUX4 and/or DUX4c sequences but not to said other DUX genes. The particular antisense and siRNA agents as taught herein are highly advantageous in this respect.

The reference herein to DUX4 and DUX4c genes, gene products, nucleic acids, proteins and polypeptides also encompasses fragments and/or variants of the respective substances.

The term "fragment" with reference to a protein or polypeptide generally denotes a N- and/or C-terminally truncated form of a protein or polypeptide. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said protein or polypeptide.

The term "fragment" with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid.

The term "variant" of a given recited nucleic acid (polynucleotide), protein or polypeptide refers to nucleic acids, proteins or polypeptides the sequence (i.e., nucleotide sequence or amino acid sequence, respectively) of which is substantially identical (i.e., largely but not wholly identical) to the sequence of said recited nucleic acid, protein or polypeptide, e.g., at least about 80% identical or at least about 85% identical, e.g., preferably at least about 90% identical, e.g., at least 91% identical, 92% identical, more preferably at least about 93% identical, e.g., at least 94% identical, even more preferably at least about 95% identical, e.g., at least 96% identical, yet more preferably at least about 97% identical, e.g., at least 98% identical, and most preferably at least 99% identical. Preferably, a variant may display such degrees of identity to a recited nucleic acid, protein or polypeptide when the whole sequence of the recited nucleic acid, protein or polypeptide is queried in the sequence alignment (i.e., overall sequence identity).

Also included among fragments and variants of a given recited nucleic acid, protein or polypeptide are fusion products of said nucleic acid, protein or polypeptide with another, usually unrelated, nucleic acid, protein or polypeptide, respectively. Particularly included among fragments and variants as intended herein are thus fusion genes between the DUX4 or DUX4c gene and other genes, leading to the expression of fusion (i.e., chimeric) proteins. More specifically included are such fusion genes arising through chromosomal rearrangements, even more specifically wherein said fusion genes and their chimeric proteins cause or contribute to a pathology. Hence, examples of DUX4 or DUX4c fragments and variants which are encompassed herein and may benefit from targeting by the antisense or RNAi agents of the present invention include fusions between CIC, a human homolog of *Drosophila capicua*, and DUX4, as seen in Ewing's family tumours (EFTs) (Kawamura-Saito et al. 2006, supra) and paediatric undifferentiated soft tissue sarcomas (USTS) (Yoshimoto et al. 2009, supra), and fusions between EWSRJ and DUX4, as seen in rhabdomyosarcomas (RMS) (Sirvent et al. 2009, supra). More generally, fusions containing the C-terminal fragment of DUX4 are intended, since the resultant chimeric proteins acquire an enhanced transcriptional activity, which may lead to tumour formation.

Sequence identity may be determined using suitable algorithms for performing sequence alignments and determination of sequence identity as know per se. Exemplary but non-limiting algorithms include those based on the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250), for example using the published default settings or other suitable settings (such as, e.g., for the BLASTN algorithm: cost to open a gap=5, cost to extend a gap=2, penalty for a mismatch=−2, reward for a match=1, gap x_dropoff=50, expectation value=10.0, word size=28; or for the BLASTP algorithm: matrix=Blosum62, cost to open a gap=11, cost to extend a gap=1, expectation value=10.0, word size=3).

In an embodiment, a variant of a given nucleic acid (polynucleotide), protein or polypeptide may be a homologue (e.g., orthologue or paralogue) of said nucleic acid, protein or polypeptide. As used herein, the term "homology" generally denotes structural similarity between two macromolecules, particularly between two nucleic acids, proteins or polypeptides, from same or different taxons, wherein said similarity is due to shared ancestry.

Where the present specification refers to variants and/or fragments of substances such as of antisense or RNAi agents, nucleic acids, proteins or polypeptides, this particularly denotes variants and/or fragments which are "functional", i.e., which at least partly retain the biological activity or intended functionality of the respective agents, nucleic acids, proteins or polypeptides.

By means of an example and not limitation, a functional variant and/or fragment of a DUX4 or DUX4c gene, gene product, nucleic acid, protein or polypeptide shall at least partly retain the biological activity of DUX4 or DUX4c, respectively. For example, such functional variant and/or fragment may retain one or more aspects of the biological activity of DUX4 or DUX4c, such as, e.g., ability to participate in one or more cellular pathways, ability to regulate transcription of one or more genes, etc.

By means of an example and not limitation, a functional variant and/or fragment of an anti-DUX4 and/or anti-DUX4c antisense agent or RNAi agent shall at least partly retain the functionality of said agent, i.e., its ability to reduce or abolish the expression of the target molecule such as DUX4 and/or DUX4c.

Preferably, a functional variant and/or fragment may retain at least about 20%, e.g., at least 30%, or at least about 40%, or at least about 50%, e.g., at least 60%, more preferably at least about 70%, e.g., at least 80%, yet more preferably at least about 85%, still more preferably at least about 90%, and most preferably at least about 95% or even about 100% or higher of the intended biological activity or functionality compared to the corresponding recited substance such as an agent, gene, gene product, nucleic acid, protein or polypeptide.

The term "nucleic acid" as used herein typically refers to a polymer (preferably a linear polymer) of any length composed essentially of nucleoside units. A nucleoside unit commonly includes a heterocyclic base and a sugar group. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Exemplary modified nucleobases include without limitation 5-substituted pyrimidines, 6-azapyrimidines and N-2, N-6 and 0-6 substituted purines, including 2-aminopropyladenine, 5-propynyluracil and 5-propynylcytosine. In particular, 5-methylcytosine substitutions have been shown to increase nucleic acid duplex stability and may be preferred base substitutions in for example antisense agents, even more particularly when combined with 2'-O-methoxyethyl sugar modifications. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups (such as without limitation 2'-O-alkylated, e.g., 2'-O-methylated or 2'-O-ethylated sugars such as ribose; 2'-O-alkyloxyalkylated, e.g., 2'-O-methoxyethylated sugars such as ribose; or 2'-O,4'-C-alkylene-linked, e.g., 2'-O,4'-C-methylene-linked or 2'-O,4'-C-ethylene-linked sugars such as ribose; 2'-fluoro-arabinose, etc.). Nucleoside units may be linked to one another by any one of numerous known inter-nucleoside linkages, including inter alia phosphodiester linkages common in naturally-occurring nucleic acids, and further modified phosphate- or phosphonate-based linkages such as phosphorothioate, alkyl phosphorothioate such as methyl phosphorothioate, phosphorodithioate, alkylphosphonate such as methylphosphonate, alkylphosphonothioate, phosphotriester such as alkylphosphotriester, phosphoramidate, phosphoropiperazidate, phosphoromorpholidate, bridged phosphoramidate, bridged methylene phosphonate, bridged phosphorothioate; and further siloxane, carbonate, sulfamate, carboalkoxy, acetamidate, carbamate such as 3'-N-carbamate, morpholino, borano, thioether, 3'-thioacetal, and sulfone inter-nucleoside linkages. Preferably, inter-nucleoside linkages may be phosphate-based linkages including modified phosphate-based linkages, such as more preferably phosphodiester, phosphorothioate or phosphorodithioate linkages or combinations thereof. The term "nucleic acid" also encompasses any other nucleobase containing polymers such as nucleic acid mimetics, including, without limitation, peptide nucleic acids (PNA), peptide nucleic acids with phosphate groups (PHONA), locked nucleic acids (LNA), morpholino phosphorodiamidate-backbone nucleic acids (PMO), cyclohexene nucleic acids (CeNA), tricyclo-DNA (tcDNA), and nucleic acids having backbone sections with alkyl linkers or amino linkers (see, e.g., Kurreck 2003 (Eur J Biochem 270: 1628-1644)). "Alkyl" as used herein particularly encompasses lower hydrocarbon moieties, e.g., C1-C4 linear or branched, saturated or unsaturated hydrocarbon, such as methyl, ethyl, ethenyl, propyl, 1-propenyl, 2-propenyl, and isopropyl. Nucleic acids as intended herein may include naturally occurring nucleosides, modified nucleosides or mixtures thereof. A modified nucleoside may include a modified heterocyclic base, a modified sugar moiety, a modified inter-nucleoside linkage or a combination thereof. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g. chemically synthesised) DNA, RNA or DNA/RNA hybrids. A nucleic acid can be naturally occurring, e.g., present in or isolated from nature, can be recombinant, i.e., produced by recombinant DNA technology, and/or can be, partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

Nucleic acids and particularly antisense oligonucleotides or RNAi agents may be herein denoted as comprising uracil (U) bases. It shall be appreciated that U may be optionally substituted by thymine (T) in (at least some) such nucleic acids and agents. For example, as 2'-O-methyl phosphorothioate antisense oligonucleotides are more 'RNA-like', U may be used and denoted in such molecules. With other antisense chemistries, such as peptide nucleic acids or morpholino backbones, T bases may be preferably denoted and used.

The term "oligonucleotide" as used herein refers to a nucleic acid (including nucleic acid analogues and mimetics) oligomer or polymer as defined herein. Preferably, an oligonucleotide, such as more particularly an antisense oligonucleotide, is (substantially) single-stranded. Oligonucleotides as intended herein may be preferably between about 10 and about 100 nucleoside units (i.e., nucleotides or nucleotide analogues) in length, preferably between about 15 and about 50, more preferably between about 20 and about 40, also preferably between about 20 and about 30. Preferably, oligonucleotides as intended herein may comprise one or more or all non-naturally occurring heterocyclic bases and/or one or more or all non-naturally occurring sugar groups and/or one or more or all non-naturally occurring inter-nucleoside linkages, the inclusion of which may improve properties such as, for example, enhanced cellular uptake, increased stability in the presence of nucleases and increased hybridization affinity, increased tolerance for mismatches, etc. Further, oligonucleotides as intended herein may be configured to not activate RNAse H, accordance with known techniques (see, e.g., U.S. Pat. No. 5,149,797).

Antisense agents such as oligonucleotides as taught herein may be further conjugated (e.g., covalently or non-covalently, directly or via a suitable linker) to one or more moieties or conjugates that enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

It is not necessary for all positions in a given agent to be uniformly modified, and in fact more than one of the aforementioned modifications may be incorporated in a single agent or even at a single nucleoside within an oligonucleotide. Further included are antisense compounds that are chimeric compounds. "Chimeric" antisense compounds or "chimeras" are antisense molecules, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the increased resistance to nuclease degradation, increased cellular uptake, and an additional region for increased binding affinity for the target nucleic acid.

The term "antisense" generally refers to an agent (e.g., an oligonucleotide) configured to specifically anneal with (hybridise to) a given sequence in a target nucleic acid, such as for example in a target DNA, hnRNA, pre-mRNA or mRNA, and typically comprises, consist essentially of or consist of a nucleic acid sequence that is complementary or substantially complementary to said target nucleic acid sequence. Antisense agents suitable for use herein may typically be capable of annealing with (hybridising to) the respective target nucleic acid sequences at high stringency conditions, and capable of hybridising specifically to the target under physiological conditions.

The terms "complementary" or "complementarity" as used herein with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C-U-3'.

The term "bind" or "binding" as used herein preferably refers to specific binding, i.e., where an agent binds to (anneals with) one or more targets of interest, such as to one or more pre-mRNA molecules or fragments or variants thereof, substantially to the exclusion of other molecules which are random or unrelated, and optionally substantially to the exclusion of other molecules that are structurally related. Binding of an agent to a target may be evaluated inter alia using conventional interaction-querying methods, such as in silico sequence analysis or nucleic acid hybridisation experiments, e.g., to verify specific hybridisation, e.g., under high stringency conditions.

Specific binding does not necessarily require that an agent binds exclusively to its intended target(s). For example, an agent may be said to specifically bind to a given pre-mRNA of interest or fragments or variants thereof if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold or at least about 1000-fold or more greater, than its affinity for a non-target molecule, such as non-target other DUX genes.

The sequence of an antisense agent need not be 100% complementary to that of its target sequence to bind or hybridise specifically with the latter. An antisense agent may be said to be specifically hybridisable when binding of the agent to a target nucleic acid molecule interferes with the normal function of the target nucleic acid such as to attain an intended outcome (e.g., loss of utility), and there is a sufficient degree of complementarity to avoid non-specific binding of the antisense agent to non-target sequences under conditions in which specific binding is desired, i.e., under physiological conditions in the case of in vivo assays or therapeutic treatment, and in the case of in vitro assays, under conditions in which the assays are performed. Thus, "specifically hybridisable" and "complementary" may indicate a sufficient degree of complementarity or precise pairing such that stable and specific binding occurs between an antisense agent and a nucleic acid target. Agents as intended herein preferably specifically bind to the desired DUX4 and/or DUX4c targets substantially to the exclusion of other DUX genes.

Preferably, to ensure specificity of antisense agents towards the desired DUX4 and/or DUX4c targets over unrelated molecules, such as over other DUX genes, the sequence of said antisense agents may be at least about 80% identical, preferably at least about 90% identical, more preferably at least about 95% identical, such as, e.g., about 96%, about 97%, about 98%, about 99% and up to 100% identical to the respective target DUX4 and/or DUX4c sequence.

The term "reduce" generally denotes a qualitative and/or quantitative alteration, change or variation leading to decrease of that which is being reduced (e.g., production and/or level of a given protein). The term covers any extent of such reduction. For example, where reduction effects a determinable or measurable variable, then such reduction may encompass a decrease in the value of said variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100% (abolishment), compared to a reference situation without said reduction. Preferably, reduction of the production and/or level of intended target(s) may be specific or selective, i.e., the production and/or level of the intended target(s) may be modulated without substantially altering the production and/or level of random, unrelated targets.

Agents such as antisense or RNAi agents as taught herein may without limitation reduce or abolish the production and/or level of DUX4 and/or DUX4c pre-mRNA and/or mRNA, whereby such agents may be capable of reducing or abolishing the production of DUX4 and/or DUX4c proteins.

Reference to the "level" of a target may preferably encompass the quantity and/or the availability (e.g., availability for performing its biological activity) of the target, e.g., within a cell, tissue, organ or an organism.

The terms "splicing", "splicing of a gene" and similar as used herein are synonymous and have their art-established meaning. By means of additional explanation, splicing denotes the process and means of removing intervening sequences (introns) from pre-mRNA in the process of producing mature mRNA. The reference to splicing particularly aims at native splicing such as occurs under normal physiological conditions. The terms "pre-mRNA" and "transcript" are used herein to denote RNA species that precede mature mRNA, such as in particular a primary RNA transcript and any partially processed forms thereof. Sequence elements required for splicing refer particularly to cis elements in the sequence of pre-mRNA which direct the cellular splicing machinery (spliceosome) towards correct and precise removal of introns from the pre-mRNA. Sequence elements involved in splicing are generally known per se and can be further determined by known techniques including inter alia mutation or deletion analysis. By means of further explanation, "splice donor site" or "5' splice site" generally refer to a conserved sequence immediately adjacent to an exon-intron boundary at the 5' end of an intron. Commonly, a splice donor site may contain a dinucleotide GU, and may involve a consensus sequence of about 8 bases at about positions +2 to −6. "Splice acceptor site" or "3' splice site" generally refers to a conserved sequence immediately adjacent to an intron-exon boundary at the 3' end of an intron. Commonly, a splice acceptor site may contain a dinucleotide AG, and may involve a consensus sequence of about 16 bases at about positions −14 to +2 (see, e.g., FIG. 1 of WO 2006/00057 for illustrative consensus sequences of splice donor and splice acceptor sites).

The terms "polyadenylation", "polyadenylation of a gene" and similar are used interchangeably herein and have their art-established meaning. By means of additional explanation, polyadenylation denotes the process and means of adding a polyadenylic acid (poly(A)) tail, i.e., multiple adenosine monophosphates, to an RNA molecule. In particular, polyadenylation may denote the process and means of adding a poly(A) tail to a pre-mRNA molecule, in the process of producing mature mRNA. The reference to polyadenylation particularly aims at native polyadenylation such as occurs under normal physiological conditions.

Sequence elements required for polyadenylation refer particularly to cis elements in the sequence of pre-mRNA which the cellular polyadenylation machinery recognises such as to which it binds, such as for example the polyadenylation signal. These sequence such as the polyadenylation signal may vary between groups of eukaryotes. For example, in humans the polyadenylation signal sequence may typically be AATAAA (i.e., AAUAAA in RNA such as pre-mRNA), but variants of it exist, such as ATTAAA.

The term "cell-penetrating peptide" or "CPP" generally refers to peptides capable of entering into cells. This ability can be exploited for the delivery of agents as disclosed herein to cells. Exemplary but non-limiting CPP include HIV-1 Tat-derived CPP (see, e.g., Frankel et al. 1988 (Science 240: 70-73)); Antennapedia peptides or penetratins (see, e.g., Derossi et al. 1994 (J Biol Chem 269: 10444-10450)); peptides derived from HSV-1 VP22 (see, e.g., Aints et al. 2001 (Gene Ther 8: 1051-1056)); transportans (see, e.g., Pooga et al. 1998 (FASEB J 12: 67-77)); protegrin 1 (PG-1) anti-microbial peptide SynB (Kokryakov et al. 1993 (FEBS Lett 327: 231-236)); model amphipathic (MAP) peptides (see, e.g., Oehlke et al. 1998 (Biochim Biophys Acta 1414: 127-139)); signal sequence-based cell-penetrating peptides (NLS) (see, e.g., Lin et al. 1995 (J Biol Chem 270: 14255-14258)); hydrophobic membrane translocating sequence (MTS) peptides (see, e.g., Lin et al. 1995, supra); and polyarginine, oligoarginine and arginine-rich peptides (see, e.g., Futaki et al. 2001 (J Biol Chem 276: 5836-5840)). The carrier peptides that have been derived from these proteins show little sequence homology with each other, but are all highly cationic and arginine or lysine rich.

CPP can be of any length. For example CPP may be less than or equal to 500, 250, 150, 100, 50, 25, 10 or 6 amino acids in length. For example CPP may be greater than or equal to 4, 5, 6, 10, 25, 50, 100, 150 or 250 amino acids in length. Preferably, a CPP may be between 4 and 25 amino acids in length. The suitable length and design of the CPP will be easily determined by those skilled in the art. As a general reference on CPPs can serve inter alia "Cell penetrating peptides: processes and applications" (ed. Ulo Langel, 1st ed., CRC Press 2002); Advanced Drug Delivery Reviews 57: 489-660 (2005); Dietz & Bahr 2004 (Moll Cell Neurosci 27: 85-131)).

An agent as disclosed herein may be conjugated with a CPP directly or indirectly, e.g., by means of a suitable linker, such as without limitation a PEG-based linker "RNA interference" or "RNAi" technology is known in the art, and refers generally to the process and means of sequence-specific post-transcriptional gene silencing mediated particularly by short interfering nucleic acids (siNA). For teaching on RNAi molecules and design thereof, see inter alia Elbashir et al. 2001 (Nature 411: 494-501), Reynolds et al. 2004 (Nat Biotechnol 22: 326-30), http://rnaidesigner.invitrogen.com/rnaiexpress, Wang & Mu 2004 (Bioinformatics 20: 1818-20), Yuan et al. 2004 (Nucleic Acids Res 32 (Web Server issue): W130-4), by M Sohail 2004 ("Gene Silencing by RNA Interference: Technology and Application", 1" ed., CRC, ISBN 0849321417), U Schepers 2005 ("RNA Interference in Practice: Principles, Basics, and Methods for Gene Silencing in *C. elegans, Drosophila*, and Mammals", $1^{st}$ ed., Wiley-VCH, ISBN 3527310207), and D R Engelke & J J Rossi 2005 ("Methods in Enzymology, Volume 392: RNA Interference", $1^{st}$ ed., Academic Press, ISBN 0121827976).

An RNAi agent typically comprises, consists essentially of or consists of a double-stranded portion or region (notwithstanding the optional and potentially preferred presence of single-stranded overhangs) of annealed complementary strands, one of which has a sequence corresponding to a target nucleotide sequence (hence, to at least a portion of an mRNA) of the target gene to be down-regulated. The other strand of the RNAi agent is complementary to said target nucleotide sequence.

Whereas the sequence of an RNAi agent need not be completely identical to a target sequence to be downregulated, the number of mismatches between a target sequence and a nucleotide sequence of the RNAi agent is preferably no more than 1 in 5 bases, or 1 in 10 bases, or 1 in 20 bases, or 1 in 50 bases.

Preferably, to ensure specificity of RNAi agents towards the desired DUX4 and/or DUX4c targets over unrelated molecules, such as over other DUX genes, the sequence of said RNAi agents may be at least about 80% identical, preferably at least about 90% identical, more preferably at least about 95% identical, such as, e.g., about 96%, about 97%, about 98%, about 99% and up to 100% identical to the respective target DUX4 and/or DUX4c sequence.

An RNAi agent may be formed by separate sense and antisense strands or, alternatively, by a common strand providing for fold-back stem-loop or hairpin design where the two annealed strands of an RNAi agent are covalently linked.

An siRNA molecule may be typically produced, e.g., synthesised, as a double stranded molecule of separate, substantially complementary strands, wherein each strand is about 18 to about 35 bases long, preferably about 19 to about 30 bases, more preferably about 20 to about 25 bases and even more preferably about 21 to about 23 bases.

shRNA is in the form of a hairpin structure. shRNA can be synthesized exogenously or can be formed by transcribing from RNA polymerase III promoters in vivo. Preferably, shRNAs can be engineered in host cells or organisms to ensure continuous and stable suppression of a desired gene. It is known that siRNA can be produced by processing a hairpin RNA in cells.

RNAi agents as intended herein may include any modifications as set out herein for nucleic acids and oligonucleotides, in order to improve their therapeutic properties.

In embodiments, at least one strand of an RNAi molecules may have a 3' overhang from about 1 to about 6 bases in length, e.g., from 2 to 4 bases, more preferably from 1 to 3 bases. For example, one strand may have a 3' overhang and the other strand may be either blunt-ended or may also have a 3'overhang. The length of the overhangs may be the same or different for each strand. The 3' overhangs can be stabilised against degradation. For example, the RNA may be stabilised by including purine nucleotides, such as A or G nucleotides. Alternatively, substitution of pyrimidine nucleotides by modified analogues, e.g., substitution of U 3' overhangs by 2'-deoxythymidine is tolerated and does not affect the efficiency of RNAi.

An exemplary but non-limiting siRNA molecule may by characterized by any one or more, and preferably by all of the following criteria:
at least about 80% sequence identity, more preferably at least about 90% or at least about 95% or at least about 97% sequence identity to target mRNA, e.g., DUX4 and/or DUX4c mRNA;
having a sequence which targets an area of the target gene present in mature mRNA (e.g., an exon or alternatively spliced intron);
showing a preference for targeting the 3' end of the target gene.

The exemplary siRNA may be further characterised by one or more or all of the following criteria:
having a double-stranded nucleic acid length of between 16 to 30 bases and preferably of between 18 to 23 bases, and preferably of 19 nucleotides;
having GC content between about 30 and about 50%
having a TT(T) sequence at 3' end;
showing no secondary structure when adopting the duplex form;
having a Tm (melting temperature) of lower than 20° C.
having the nucleotides indicated here below in the sequence of the nucleotides, wherein "h" is A, C, T/U but not G; wherein "d" is A, G, T/U but not C, and wherein "w" is A or T/U, but not G or C:

|  |  | — | — | 1 | 2 | 3 | 4 | 5 | 6 | 7 | 8 | 9 | 10 | 11 | 12 | 13 | 14 | 15 | 16 | 17 | 18 | 19 | — | — |
|---|---|---|---|---|---|---|---|---|---|---|---|---|---|---|---|---|---|---|---|---|---|---|---|---|
| mRNA | P'5 | A | A |  |  | A |  |  |  |  |  |  | U |  | h |  |  |  |  | w |  |  | 3'-OH |  |
| si-ASense | OH-3' | T | T |  |  | U |  |  |  |  |  |  | A |  | d |  |  |  |  | w |  |  | 5'-P |  |
| si-Sense | P-5' |  |  |  |  | A |  |  |  |  |  |  | U |  | h |  |  |  |  | w | T | T | 3'-OH |  |

Production of agents intended herein, such as antisense agents and RNAi agents, can be carried out by any processes known in the art, such as inter alia partly or entirely by chemical synthesis (e.g., routinely known solid phase synthesis; an exemplary an non-limiting method for synthesising oligonucleotides on a modified solid support is described in U.S. Pat. No. 4,458,066; in another example, diethylphosphoramidites are used as starting materials and may be synthesised as described by Beaucage et al. 1981 (Tetrahedron Letters 22: 1859-1862)), or partly or entirely by biochemical (enzymatic) synthesis, e.g., by in vitro transcription from a nucleic acid construct (template) using a suitable polymerase such as a T7 or SP6 RNA polymerase, or by recombinant nucleic acid techniques, e.g., expression from a vector in a host cell or host organism. Nucleotide analogues can be introduced by in vitro chemical or biochemical synthesis. In an embodiment, the antisense agents of the invention are synthesised in vitro and do not include antisense compositions of biological origin, or genetic vector constructs designed to direct the in vivo synthesis of antisense molecules.

The term "isolated" with reference to a particular component (such as for instance a nucleic acid) generally denotes that such component exists in separation from—for example, has been separated from or prepared and/or maintained in separation from—one or more other components of its natural environment. For instance, an isolated human or animal nucleic acid may exist in separation from a human or animal body where it naturally occurs.

The term "isolated" as used herein may preferably also encompass the qualifier "purified". By means of example, the term "purified" with reference to a substance (e.g., an agent or a nucleic acid) does not require absolute purity. Instead, it denotes that such substances are in a discrete environment in which their abundance (conveniently expressed in terms of mass or weight or concentration) relative to other relevant substances is greater than in a biological sample. A discrete environment denotes a single medium, such as for example a single solution, gel, precipitate, lyophilisate, etc. Purified substances may be obtained by known methods including, for example, laboratory or recombinant synthesis, chromatography, preparative electrophoresis, centrifugation, precipitation, affinity purification, etc.

By means of example and not limitation, purified nucleic acids (including NA-based or NA-comprising agents) may preferably constitute by weight ≥about 10%, more preferably ≥about 50%, such as ≥about 60%, yet more preferably ≥about 70%, such as ≥about 80%, and still more preferably ≥about 90%, such as ≥about 95%, ≥about 96%, ≥about 97%, ≥about 98%, ≥about 99% or even 100%, of the nucleic acid content of the discrete environment. For example, purity of a nucleic acid may be determined by measuring absorbance $A_{260}/A_{280}$. Also, an isolated nucleic acid may be purified to homogeneity as determined by agarose- or polyacrylamide-gel electrophoresis and ethidium bromide or similar staining.

By "encoding" is particularly meant that a nucleic acid sequence or part(s) thereof corresponds to another nucleic acid sequence in a template—transcription product (e.g., RNA or RNA analogue) relationship, or corresponds, by virtue of the genetic code of an organism in question, to a particular amino acid sequence, e.g., the amino acid sequence of one or more desired proteins or polypeptides.

Preferably, a nucleic acid encoding one or more proteins or polypeptides may comprise an open reading frame (ORF) encoding said protein or polypeptide. An "open reading frame" or "ORF" refers to a succession of coding nucleotide triplets (codons) starting with a translation initiation codon and closing with a translation termination codon known per se, and not containing any internal in-frame translation termination codon, and potentially capable of encoding a protein or polypeptide. Hence, the term may be synonymous with "coding sequence" as used in the art.

Expression of transcription products or proteins and polypeptides can be achieved through operably linking nucleic acid sequences or ORFs encoding the intended transcription products or proteins and polypeptides with regulatory sequences allowing for expression of the nucleic acids or ORFs, e.g., in vitro, in a host cell, host organ and/or host organism. Such expression may be achieved, e.g., under suitable (culture) conditions or upon addition of inducers (e.g., where inducible regulatory sequences are used).

An "operable linkage" is a linkage in which regulatory sequences and sequences sought to be expressed are connected in such a way as to permit said expression. For example, sequences, such as, e.g., a promoter and an ORF, may be said to be operably linked if the nature of the linkage between said sequences does not: (1) result in the introduction of a frame-shift mutation, (2) interfere with the ability of the promoter to direct the transcription of the ORF, (3) interfere with the ability of the ORF to be transcribed from the promoter sequence.

The precise nature of regulatory sequences or elements required for expression may vary between expression environments, but may typically include a promoter and a transcription terminator, and optionally an enhancer, as known per se.

The term "vector" generally refers to a nucleic acid molecule, typically DNA, to which nucleic acid segments may be inserted and cloned, i.e., propagated. Hence, a vector will typically contain one or more unique restriction sites, and may be capable of autonomous replication in a defined host or vehicle organism such that the cloned sequence is reproducible. Vectors may include, without limitation, plasmids, phagemids, bacteriophages, bacteriophage-derived vectors, PAC, BAC, linear nucleic acids, e.g., linear DNA, viral vectors, etc., as appropriate. Expression vectors are generally configured to allow for and/or effect the expression of nucleic acids or ORFs introduced thereto in a desired expression system, e.g., in vitro, in a host cell, host organ and/or host organism. For example, expression vectors may advantageously comprise suitable regulatory sequences.

Preferred vectors for use herein are viral vectors, which are well known and include vectors derived from for example, but without limitation, retroviruses, vaccinia viruses, poxviruses, adenoviruses, and adeno-associated viruses (AAV). Such viral vectors may me be engineered by recombinant techniques as known per se to introduce thereto nucleic acid sequence(s) encoding any one of the antisense or RNAi agents disclosed herein.

For example, a retroviral vector may be used herein. Generally, retroviral vectors may comprise the retroviral genomic sequences encoding components necessary for the integration of the recombinant viral genome (randomly) into the host cell genome and the nucleic acid sequence(s) of interest, such as in particular the nucleic acid sequence(s) encoding any one of the antisense or RNAi agents disclosed herein. Such retroviral vectors may be readily constructed using standard recombinant techniques (e.g., Sambrook et al., Molecular Cloning: A Laboratory Manual, 2d ed., Cold Spring Harbor Laboratory Press, 1989) from a wide variety of retroviruses, including for example, B, C, and D type retroviruses as well as spumaviruses and lentiviruses (see RNA Tumor Viruses, Second Edition, Cold Spring Harbor Laboratory, 1985).

Recombinant adenoviral vectors may also be contemplated for delivery and expression of antisense or RNAi agents as disclosed herein in a host cell. Adenovirus-based viral vectors have the advantage of being capable of infecting non-dividing host cells, but the recombinant viral genome is not integrated into the host cell genome. For example, a suitable adenoviral vector, a method for constructing a recombinant adenoviral vector thereof, and a method for delivering the recombinant vector into host cells, are described in Xia H et al. (2002) (Nat. Biotech. 20: 1006-1010). Use of recombinant AAV (RAAV) vectors is also contemplated herein. RAAV vectors can infect both dividing and non-dividing cells and may incorporate its recombinant viral genome into that of the host cell. RAAV vectors may be generated from a variety of adeno-associated viruses, including for example, serotypes 1 through 6. Generally, RAAV vectors may comprise, in order, a 5' adeno-associated virus inverted terminal repeat (ITR), a nucleic acid of interest, such as in particular a nucleic acid sequence encoding any one of the antisense or RNAi agents disclosed herein, operatively linked to a sequence which regulates its expression in a host cell or host organism, and a 3' adeno-associated virus ITR. In addition, the rAAV vector may preferably have a polyadenylation signal. Suitable RAAV vectors are described inter alia in WO 1994/13788, WO 1993/24641, and in Goyenvalle et al. 2004 (Science 306: 1796-1799) where antisense sequences are linked to a modified U7 small nuclear RNA.

Other preferred viral vectors for use herein are vectors derived from a pox virus such as a vaccinia virus, for example an attenuated vaccinia virus such as Modified Virus Ankara (MVA) or NYVAC, an avipox virus such as fowl pox virus or canary pox virus.

The terms "host cell" and "host organism" may suitably refer to cells or organisms encompassing both prokaryotes, such as bacteria, and eukaryotes, such as yeast, fungi, protozoan, plants and animals. Contemplated as host cells are inter alia unicellular organisms, such as bacteria (e.g., *E. coli, Salmonella tymphimurium, Serratia marcescens*, or *Bacillus subtilis*), yeast (e.g., *Saccharomyces cerevisiae* or *Pichia pastoris*), (cultured) plant cells (e.g., from *Arabidopsis thaliana* or *Nicotiana tobaccum*) and (cultured) animal cells (e.g., vertebrate animal cells, mammalian cells, primate cells, human cells or insect cells). Contemplated as host organisms are inter alia multi-cellular organisms, such as plants and animals, preferably animals, more preferably warm-blooded animals, even more preferably vertebrate animals, still more preferably mammals, yet more preferably primates; particularly contemplated are such animals and animal categories which are non-human.

The reference to antisense agents and RNAi agents as used herein also encompasses any pharmaceutically acceptable salts, esters, or salts of such esters, or any other compound which, upon administration to an animal including a human, is capable of providing (directly or indirectly) the biologically active metabolite or residue thereof. Accordingly, for example, also encompassed in the disclosure are pro-drugs and pharmaceutically acceptable salts of the compounds of the invention, pharmaceutically acceptable salts of such pro-drugs, and other bio-equivalents.

The term "pharmaceutically acceptable salts" refers to physiologically and pharmaceutically acceptable salts of the agents disclosed herein, wherein said salts retain the desired biological activity of the parent agent and do not impart undesired toxicological effects thereto. For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The various active substances of the present disclosure, such as inter alia antisense agents, RNAi agents, vectors and cells as taught herein or pharmaceutically acceptable derivatives thereof, may be formulated into pharmaceutical compositions or formulations with one or more pharmaceutically acceptable carriers/excipients.

The term "pharmaceutically acceptable" as used herein is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline, phosphate buffered saline, or optionally Tris-HCl, acetate or phosphate buffers), solubilisers (such as, e.g., Tween 80, Polysorbate 80), colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives (such as, e.g., Thimerosal™, benzyl alcohol), antioxidants (such as, e.g., ascorbic acid, sodium metabisulfite), tonicity controlling agents, absorption delaying agents, adjuvants, bulking agents (such as, e.g., lactose, mannitol) and the like. The use of such media and agents for pharmaceutical active substances is well known in the art. Except insofar as any conventional media or agent is incompatible with the active substance, its use in the therapeutic compositions may be contemplated. Suitable pharmaceutical carriers are described inter alia in Remington's Pharmaceutical Sciences, 18th ed., Mack Publishing Co., Easton, PA (1990).

Illustrative, non-limiting carriers for use in formulating the pharmaceutical compositions include, for example, oil-in-water or water-in-oil emulsions, aqueous compositions with or without inclusion of organic co-solvents suitable for intravenous (IV) use, liposomes or surfactant-containing vesicles, particulate preparations with polymeric compounds such as inter alia polylactic acid or polyglycolic acid, microspheres, microbeads and microsomes, powders, tablets, capsules, suppositories, aqueous suspensions, aerosols, and other carriers apparent to one of ordinary skill in the art.

Pharmaceutical carriers may comprise sterile liquids, such as water and oils, including those of petroleum, animal, vegetable or synthetic origin, such as peanut oil, soybean oil, mineral oil, sesame oil and the like.

Pharmaceutical compositions of the invention may be formulated for essentially any route of administration, such as without limitation, oral administration (such as, e.g., oral ingestion or inhalation), intranasal administration (such as, e.g., intranasal inhalation or intranasal mucosal application), pulmonary (such as, e.g., by inhalation or insufflation of powders or aerosols), parenteral administration (such as, e.g., subcutaneous, intravenous, intra-arterial, intramuscular, intraperitoneal or intrasternal injection or infusion, or intracranial, e.g., intrathecal or intraventricular administration), epidermal and transdermal, or transmucosal (such as, e.g., oral, sublingual, intranasal) administration, topical administration (including inter alia ophthalmic administration), rectal, vaginal or intra-tracheal instillation, and the like. In this way, the therapeutic effects attainable by the methods and compositions of the invention can be, for example, systemic, local, tissue-specific, etc., depending of the specific needs of a given application of the invention. Oligonucleotides with at least one 2'-O-methoxyethyl modification are believed to be particularly useful for oral administration.

For example, for oral administration, pharmaceutical compositions may be formulated in the form of pills, tablets, lacquered tablets, coated (e.g., sugar-coated) tablets, granules, hard and soft gelatin capsules, aqueous, alcoholic or oily solutions, syrups, emulsions or suspensions. In an example, without limitation, preparation of oral dosage forms may be is suitably accomplished by uniformly and intimately blending together a suitable amount of the active compound in the form of a powder, optionally also including finely divided one or more solid carrier, and formulating the blend in a pill, tablet or a capsule. Exemplary but non-limiting solid carriers include calcium phosphate, magnesium stearate, talc, sugars (such as, e.g., glucose, mannose, lactose or sucrose), sugar alcohols (such as, e.g., mannitol), dextrin, starch, gelatin, cellulose, polyvinylpyrrolidine, low melting waxes and ion exchange resins. Compressed tablets containing the pharmaceutical composition can be prepared by uniformly and intimately mixing the active ingredient with a solid carrier such as described above to provide a mixture having the necessary compression properties, and then compacting the mixture in a suitable machine to the shape and size desired. Moulded tablets maybe made by moulding in a suitable machine, a mixture of powdered compound moistened with an inert liquid diluent. Suitable carriers for soft gelatin capsules and suppositories are, for example, fats, waxes, semisolid and liquid polyols, natural or hardened oils, etc.

For example, for oral or nasal aerosol or inhalation administration, pharmaceutical compositions may be formulated with illustrative carriers, such as, e.g., as in solution with saline, polyethylene glycol or glycols, DPPC, methylcellulose, or in mixture with powdered dispersing agents, further employing benzyl alcohol or other suitable preservatives, absorption promoters to enhance bioavailability, fluorocarbons, and/or other solubilising or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Illustratively, delivery may be by use of a single-use delivery device, a mist nebuliser, a breath-activated powder inhaler, an aerosol metered-dose inhaler (MDI) or any other of the numerous nebuliser delivery devices available in the art. Additionally, mist tents or direct administration through endotracheal tubes may also be used.

Examples of carriers for administration via mucosal surfaces depend upon the particular route, e.g., oral, sublingual, intranasal, etc. When administered orally, illustrative examples include pharmaceutical grades of mannitol, starch, lactose, magnesium stearate, sodium saccharide, cellulose, magnesium carbonate and the like, with mannitol being preferred. When administered intranasally, illustrative examples include polyethylene glycol, phospholipids, glycols and glycolipids, sucrose, and/or methylcellulose, powder suspensions with or without bulking agents such as lactose and preservatives such as benzalkonium chloride, EDTA. In a particularly illustrative embodiment, the phospholipid 1,2 dipalmitoyl-sn-glycero-3-phosphocholine (DPPC) is used as an isotonic aqueous carrier at about 0.01-0.2% for intranasal administration of the compound of the subject invention at a concentration of about 0.1 to 3.0 mg/ml.

For example, for parenteral administration, pharmaceutical compositions may be advantageously formulated as solutions, suspensions or emulsions with suitable solvents, diluents, solubilisers or emulsifiers, etc. Suitable solvents are, without limitation, water, physiological saline solution or alcohols, e.g. ethanol, propanol, glycerol, in addition also sugar solutions such as glucose, invert sugar, sucrose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. The compounds and pharmaceutically acceptable salts thereof of the invention can also be lyophilised and the lyophilisates obtained used, for example, for the production of injection or infusion preparations. For example, one illustrative example of a carrier for intravenous use includes a mixture of 10% USP ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Water or saline solutions and aqueous dextrose and glycerol solutions may be preferably employed as carriers, particularly for injectable solutions. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Where aqueous formulations are preferred, such may comprise one or more surfactants. For example, the composition can be in the form of a micellar dispersion comprising at least one suitable surfactant, e.g., a phospholipid surfactant. Illustrative examples of phospholipids include diacyl phosphatidyl glycerols, such as dimyristoyl phosphatidyl glycerol (DPMG), dipalmitoyl phosphatidyl glycerol (DPPG), and distearoyl phosphatidyl glycerol (DSPG), diacyl phosphatidyl cholines, such as dimyristoyl phosphatidylcholine (DPMC), dipalmitoyl phosphatidylcholine (DPPC), and distearoyl phosphatidylcholine (DSPC); diacyl phosphatidic acids, such as dimyristoyl phosphatidic acid (DPMA), dipahnitoyl phosphatidic acid (DPPA), and distearoyl phosphatidic acid (DSPA); and diacyl phosphatidyl ethanolamines such as dimyristoyl phosphatidyl ethanolamine (DPME), dipalmitoyl phosphatidyl ethanolamine (DPPE) and distearoyl phosphatidyl ethanolamine (DSPE). Typically, a surfactant:active substance molar ratio in an aqueous formulation will be from about 10:1 to about 1:10, more typically from about 5:1 to about 1:5, however any effective amount of surfactant may be used in an aqueous formulation to best suit the specific objectives of interest.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquidify and/or dissolve in the rectal cavity to release the drug.

Suitable carriers for microcapsules, implants or rods are, for example, copolymers of glycolic acid and lactic acid.

One skilled in this art will recognize that the above description is illustrative rather than exhaustive. Indeed, many additional formulations techniques and pharmaceutically-acceptable excipients and carrier solutions are well-known to those skilled in the art, as is the development of suitable dosing and treatment regimens for using the particular compositions described herein in a variety of treatment regimens.

Further, there are several well-known methods of introducing nucleic acids (e.g., antisense and RNAi agents) into animal cells, any of which may be used herein. At the simplest, the nucleic acid can be directly injected into the target cell/target tissue. Other methods include fusion of the recipient cell with bacterial protoplasts containing the nucleic acid, the use of compositions like calcium chloride, rubidium chloride, lithium chloride, calcium phosphate, DEAE dextran, cationic lipids or liposomes or methods like receptor-mediated endocytosis, biolistic particle bombardment ("gene gun" method), infection with viral vectors, for example such as taught herein, electroporation, and the like. Other techniques or methods which are suitable for delivering nucleic acid molecules to target cells include the continuous delivery of an NA molecule from poly (lactic-Co-Glycolic Acid) polymeric microspheres or the direct injection of protected (stabilized) NA molecule(s) into micropumps delivering the product. Another possibility is the use of implantable drug-releasing biodegradable microspheres. Also envisaged is encapsulation of NA in various types of liposomes (immunoliposomes, PEGylated (immuno) liposomes), cationic lipids and polymers, nanoparticules or dendrimers, poly (lactic-Co-Glycolic Acid) polymeric microspheres, implantable drug-releasing biodegradable microspheres, etc; and co-injection of NA with protective agent like the nuclease inhibitor aurintricarboxylic acid. It shall be clear that also a combination of different above-mentioned delivery modes or methods may be used.

A preferred method of intracellular delivery of the antisense agents and RNAi agents disclosed herein may include infection with viral vectors as taught herein. In such method, a recombinant viral vector as taught herein, is brought in contact with a host cell, such as introduced (e.g., locally or systemically) to a host organism, and incubated at conditions favourable to viral infection and hence, makes use of the natural ability of a virus to infect a cell. For example, a retrovirus obtains entry to a host cell via the interaction of a retroviral protein with a transmembrane protein acting as a receptor on the surface of the host cell. Another approach of viral vector-mediated delivery of antisense and RNAi agents as disclosed herein may encompass a physical cell entry-based technique, such as for example the use of ultrasound and microbubbles, in combination with viral vector-mediated delivery as described in WO 2006/129080.

Further ways of delivery of nucleic acids such as antisense agents and RNAi agents may employ previously published methods. For example, intracellular delivery of the nucleic acids may be via a composition comprising an admixture of the nucleic acid molecule and an effective amount of a block copolymer. An example of this method is described in US 2004/0248833.

Other methods of delivery of nucleic acids to the nucleus are described in Mann et al. 2001 (Proc Natl Acad Science 98(1): 42-47) and in Gebski et al. 2003 (Human Molecular Genetics 12(15): 1801-1811).

A method for introducing a nucleic acid molecule into a cell by way of an expression vector either as naked DNA or complexed to lipid carriers, is described in U.S. Pat. No. 6,806,084.

It may be desirable to deliver a nucleic acid molecule in a colloidal dispersion system. Colloidal dispersion systems include macromolecule complexes, nanocapsules, microspheres, beads, and lipid-based systems including oil-in-water emulsions, micelles, mixed micelles, and liposomes or liposome formulations. Liposomes are artificial membrane vesicles which are useful as delivery vehicles in vitro and in vivo. These formulations may have net cationic, anionic or neutral charge characteristics and are useful characteristics with in vitro, in vivo and ex vivo delivery methods. It has been shown that large unilamellar vesicles (LUV), which range in size from 0.2-4.0 PHI.m can encapsulate a substantial percentage of an aqueous buffer containing large macromolecules. RNA, and DNA can be encapsulated within the aqueous interior and be delivered to cells in a biologically active form (Fraley et al. 1981 (Trends Biochem ScL 6: 77).

In order for a liposome to be an efficient gene transfer vehicle, the following characteristics should be present: (1) encapsulation of the nucleic acid molecule of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al. 1988 (Biotechniques 6: 682).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Alternatively, the nucleic acid molecule may be combined with other pharmaceutically acceptable carriers or diluents to produce a pharmaceutical composition. Suitable carriers and diluents include isotonic saline solutions, for example phosphate-buffered saline. The composition may be formulated for parenteral, intramuscular, intravenous, subcutaneous, intraocular, oral or transdermal administration.

The routes of administration described are intended only as a guide since a skilled practitioner will be able to determine readily the optimum route of administration and any dosage for any particular animal and condition. Multiple approaches for introducing functional new genetic material into cells, both in vitro and in vivo have been attempted (Friedmann 1989 (Science 244: 1275-1280)). These approaches include integration of the gene to be expressed into modified retroviruses (Friedmann 1989, supra; Rosenberg 1991 (Cancer Research 51(18), suppl.: 5074S-5079S)); integration into non-retrovirus vectors (Rosenfeld et al. 1992 (Cell 68: 143-155); Rosenfeld et al. 1991 (Science 252: 431-434)); or delivery of a transgene linked to a heterologous promoter-enhancer element via liposomes (Friedmann 1989, supra; Brigham et al. 1989 (Am J Med Sci 298: 278-281); Nabel et al. 1990 (Science 249: 1285-1288); Hazinski et al. 1991 (Am J Resp Cell Molec Biol 4: 206-209); and Wang and Huang 1987 (Proc Natl Acad Sci USA, 84: 7851-7855)); coupled to ligand-specific, cation-based transport systems (Wu and Wu 1988 (J Biol Chem 263: 14621-14624)) or the use of naked DNA, expression vectors (Nabel et al. 1990, supra); Wolff et al. 1990 (Science 247: 1465-1468)). Direct injection of transgenes into tissue produces only localized expression (Rosenfeld 1992, supra; Rosenfeld et al. 1991, supra; Brigham et al. 1989, supra; Nabel 1990, supra; and Hazinski et al. 1991, supra). The Brigham et al. group (Am J Med Sci 298: 278-281 (1989) and Clinical Research 39 (abstract) (1991)) have reported in vivo transfection only of lungs of mice following either intravenous or intratracheal administration of a DNA liposome complex. An example of a review article of human gene therapy procedures is: Anderson 1992 (Science 256: 808-813).

The pharmaceutical formulations as disclosed herein, which may conveniently be presented in unit dosage form, may be prepared according to conventional techniques well known in the pharmaceutical industry. Such techniques may generally include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The present active substances may be used alone or in combination with any other pharmaceutically or biologically active ingredient, particularly which is suitable for the treatment of diseases as taught herein ("combination therapy"). Combination therapies as contemplated herein may comprise the administration of at least one active substance of the present invention and at least one other pharmaceutically or biologically active ingredient. Said present active substance(s) and said pharmaceutically or biologically active ingredient(s) may be administered in either the same or different pharmaceutical formulation(s), simultaneously or sequentially in any order.

The dosage or amount of the present active substances used, optionally in combination with one or more other active compound to be administered, depends on the individual case and is, as is customary, to be adapted to the individual circumstances to achieve an optimum effect. Thus, it depends on the nature and the severity of the disorder to be treated, and also on the sex, age, body weight, general health, diet, mode and time of administration, and individual responsiveness of the human or animal to be treated, on the route of administration, efficacy, metabolic stability and duration of action of the compounds used, on whether the therapy is acute or chronic or prophylactic, or on whether other active compounds are administered in addition to the agent(s) of the invention.

Without limitation, depending on the type and severity of the disease, a typical daily dosage might range from about 1 μg/kg to 100 mg/kg of body weight or more, depending on the factors mentioned above. For repeated administrations over several days or longer, depending on the condition, the treatment is sustained until a desired suppression of disease symptoms occurs. A preferred dosage of the active substance of the invention may be in the range from about 0.05 mg/kg to about 10 mg/kg of body weight. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every two or three weeks.

In an embodiment, a pharmaceutical composition may comprise between about 10 nM and about 1 μM, preferably between about 20 nM and about 600 nM, such as, e.g., about 100 nM or about 200 nM, or about 300 nM, or about 400 nM or about 500 nM of antisense agent or RNAi agent as taught herein.

Except when noted, "subject" or "patient" are used interchangeably and refer to animals, preferably warm-blooded animals, more preferably vertebrates, even more preferably mammals, still more preferably primates, and specifically includes human patients and non-human mammals and primates. Preferred patients are human subjects.

As used herein, a phrase such as "a subject in need of treatment" includes subjects that would benefit from treatment of a given condition, particularly of facioscapulohumeral muscular dystrophy (FSHD) or a tumour, such as preferably a sarcoma, such as more preferably a sarcoma selected from Ewing's family tumours, paediatric undifferentiated soft tissue sarcomas and rhabdomyosarcomas. Such subjects may include, without limitation, those that have been diagnosed with said condition, those prone to contract or develop said condition and/or those in whom said condition is to be prevented.

The terms "treat" or "treatment" encompass both the therapeutic treatment of an already developed disease or condition, such as the therapy of an already developed FSHD or tumour, such as preferably a sarcoma, such as more preferably a sarcoma selected from Ewing's family tumours, paediatric undifferentiated soft tissue sarcomas and rhabdomyosarcomas, as well as prophylactic or preventative measures, wherein the aim is to prevent or lessen the chances of incidence of an undesired affliction, such as to prevent the chances of contraction and progression of FSHD or a tumour, such as preferably a sarcoma, such as more preferably a sarcoma selected from Ewing's family tumours, paediatric undifferentiated soft tissue sarcomas and rhabdomyosarcomas. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

The term "prophylactically effective amount" refers to an amount of an active compound or pharmaceutical agent that inhibits or delays in a subject the onset of a disorder as being sought by a researcher, veterinarian, medical doctor or other clinician. The term "therapeutically effective amount" as used herein, refers to an amount of active compound or pharmaceutical agent that elicits the biological or medicinal response in a subject that is being sought by a researcher, veterinarian, medical doctor or other clinician, which may include inter alia alleviation of the symptoms of the disease or condition being treated. Methods are known in the art for determining therapeutically and prophylactically effective doses for the present compounds.

Reference to "diseases or conditions comprising increased levels and/or increased activity of double homeobox 4 and/or double homeobox 4c" generally covers diseases and conditions in which the level and/or activity of DUX4 and/or DUX4c is increased by any (measurable) extent compared to a reference non-disease state, such as without limitation is increased by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference non-disease state. The term also covers situations in which a reference non-disease state comprises no demonstrable level and/or activity of DUX4 and/or DUX4c whereas a disease state comprises some demonstrable level and/or activity of DUX4 and/or DUX4c. The level and/or activity of DUX4 and/or DUX4c may be increased in any cells, tissues and/or organs of a patient, preferably in cells, tissues and/or organs relevant to or affected in a disease or condition. For example, the level and/or activity of DUX4 and/or DUX4c may be increased in muscle cells and muscle tissues, such as, e.g., in myoblasts and/or in myocytes, in smooth muscles and/or in striated muscles such as in skeletal and or cardiac muscles, etc.

The level of DUX4 and/or DUX4c may be measured at any one or more stages, such as at the stage of pre-mRNA or mRNA (e.g., by qualitative or quantitative RT-PCR) and/or protein (e.g., immunoassay methods). The activity of DUX4 and/or DUX4c protein may be measured by any suitable biochemical or cellular assays, e.g., measuring its trans-activation potential on known targets.

Facioscapulohumeral muscular dystrophy (FSHD, FSHMD or FSH) also known as Landouzy-Dejerine muscular dystrophy encompasses all diseases and condition known under these designations in the art. More particularly, FSHD as intended herein is an autosomal dominant muscle disorder genetically linked to contractions of the D4Z4 repeat array on the 4q35 subtelomeric region, more particularly where FSHD patients have between 1 and 10 D4Z4 copies, such as e.g., 2, 3, 4, 5, 6, 7, 8 or 9 copies. Also particularly, FSHD may be linked to the 4qA allele, even more particularly to the permissive alleles 4A161, 4A161L, 4A159 or 4A168.

Moreover, although a small group of patients with a typical FSHD phenotype presents more than 10 copies of the D4Z4 element, these patients show sub-normal DNA methylation level at the repeat, similar to that found in contracted D4Z4 arrays. Consequently, FSHD can be generally concluded when DNA hypomethylation is observed at the D4Z4 repeat, irrespective of the number of D4Z4 units.

Diseases or conditions the treatment of which can benefit from reducing the expression of double homeobox 4 and/or double homeobox 4c also specifically encompass those which comprise expression of DUX4 and/or DUX4c fragments or variants, more particularly expression of fusion proteins between DUX4 or DUX4c (preferably DUX4) and other, unrelated proteins, more preferably, such fusion proteins comprising the C-terminal fragment of DUX4 or DUX4c (preferably DUX4), even more preferably such fusion proteins with CIC, a human homolog of *Drosophila capicua*, or with EWSR1. Said fusion proteins are commonly expressed as a result of chromosomal rearrangements and favour cell proliferation and hence, may cause tumours, such as in particular Ewing's family tumours (EFTs) (Kawamura-Saito et al. 2006, supra) and paediatric undifferentiated soft tissue sarcomas (Yoshimoto et al. 2009, supra) and rhabdomyosarcomas (Sirvent et al. 2009, supra), respectively. Since said fusion mRNAs include the sequence elements of the DUX4 or DUX4c genes (preferably the DUX4 gene) that are targeted by the antisense agents and/or RNAi agents as described herein, these tools may reduce the expression of said fusion proteins similarly as they reduce the expression of the full length DUX4 or DUX4c protein. Hence, diseases and conditions intended herein also include tumours, more particularly sarcomas, even more particularly the aforementioned tumour types. As used herein, the term "tumour" refers to an abnormal mass of tissue that results from excessive cell division. A tumour comprises "tumour cells" which are neoplastic cells with abnormal growth properties and may also comprise "tumour-associated non-tumour cells", e.g., vascular cells which form blood vessels to supply the tumour. A tumour may be benign or malignant. The term "sarcoma" encompasses tumour types involving connective tissue cells, such as for example but without limitation bone, cartilage, fat cells, muscles and blood vessels.

It is apparent that there have been provided in accordance with the invention products, methods and uses that provide for substantial advantages as set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The above aspects and embodiments are further supported by the following non-limiting examples.

EXAMPLES

Example 1: Antisense Oligonucleotides Directed Against Sequence Elements Involved in Splicing of DUX4 Pre-mRNA are Highly Effective in Down-Regulating Double Homeobox 4 Expression Antisense oligomers (AO) were designed based on the sequence of the DUX4 gene 3' UTR (FIG. 1). The 7 AO include one (JSR1521 pLAM2A) directed against positions −7+18 of DUX4 intron 1—exon 2 boundary (incl. intron 1 splice acceptor site), and six AO directed against DUX4 intron 2—exon 3 boundary (incl. intron 2 splice acceptor site), denoted JSR1522 pLam3A (−7+18), JSR1523 pLAM3A (−12+13), JSR1524 pLAM3A (−2+23), JSR1696 pLAM3A (−7+18), JSR1719 pLAM3A (−12+18) and JSR1720 pLAM3A (−17+13). An AO targeting dystrophin was used as negative control.

```
Anti-DUX4 AO:
JSR 1521 pLAM2A (-7+18):
                                      (SEQ ID NO: 16)
CUCUCACCGGGCCUAGACCUAGAAG JSR 1522 pLam3A (-7+18):
                                      (SEQ ID NO: 17)
UGCGCACUGCGCGCAGGUCUAGCCA JSR1523 pLAM3A (-12+13):
                                      (SEQ ID NO: 18)
ACUGCGCGCAGGUCUAGCCAGGAAG JSR1524 pLAM3A (-2+23):
                                      (SEQ ID NO: 19)
CGGGGUGCGCACUGCGCGCAGGUCU JSR1696 pLAM3A (-7+18):
                                      (SEQ ID NO: 17)
UGCGCACUGCGCGCAGGUCUAGCCA JSR1719 pLAM3A(-12+18):
                                      (SEQ ID NO: 20)
UGCGCACUGCGCGCAGGUCUAGCCAGGAAG JSR1720 pLAM3A (-17+13):
                                      (SEQ ID NO: 21)
ACUGCGCGCAGGUCUAGCCAGGAAGCGGGC AO targeting dystrophin (negative controls)
JSR1662 mGMCSF3A (-05+20):
UCCCACAGAAGCUAACAUGUGUGCAGAC
```

All AO used in this example had 2'-O-methyl-phosphorothioate backbone. AO having phosphorodiamidate morpholino backbone are used with at least comparable or superior results. AO conjugated to a cell penetrating peptide (CPP) are used with at least comparable or superior results. Testing C2C12 Mouse Myoblasts Transiently Expressing Dux4

The efficacy of antisense oligonucleotides (AO) against the DUX4 pre-mRNA was evaluated in transient expression in C2C12 mouse myoblasts grown in vitro. These cells were transfected with the pCIneo-DUX4 expression vector that contains the DUX4 coding region of the last D4Z4 element and the flanking pLAM region under the strong CMV promoter.

$10^5$ C2C12 mouse myoblasts were seeded per well of 6-well dishes and grown at 37° C. and 5% $CO_2$ in DMEM, 10% foetal bovine serum gold (PAA), 1% antibiotics (penicillin, streptomycin, fungizon). They were transfected 24 hours later with 500 ng per well of expression vector pCIneo-DUX4 alone or combined with the indicated AO. The negative control is AO 1662 that targets the dystrophin mRNA. The transfection reagent was Lipofectamine™ 2000 (Invitrogen) used at a ratio of 1 μg AO/1 μl reagent, and 600 nM AO concentration. The cells were lysed 24 hours after transfection, and total protein extracts were prepared in NuPAGE® LDS sample buffer (Invitrogen). 15 μg of protein extracts were separated by electrophoresis (SDS-PAGE 12%), and transferred to a nitrocellulose membrane. DUX4 (52 kDa) was detected on this Western blot with the 9A12 monoclonal antibody followed by anti-mouse IgG antibodies coupled to peroxidase (HRP), and revealed with Lumi- Light kit (Roche) detected on a film. After striping these antibodies, the same membrane was incubated with an anti-actin antibody to provide a loading control. The mouse monoclonal antibody (MAb 9A12) was raised as described in Dixit et al. 2007 (supra) directed against the carboxyl terminal part of DUX4. Whereas this antibody cross reacts with DUX4c, the two proteins can be readily distinguished in Western blot based on their different apparent molecular weights, i.e., 52 kDa for DUX4 and 47 kDa for DUX4c.

Figure 9:
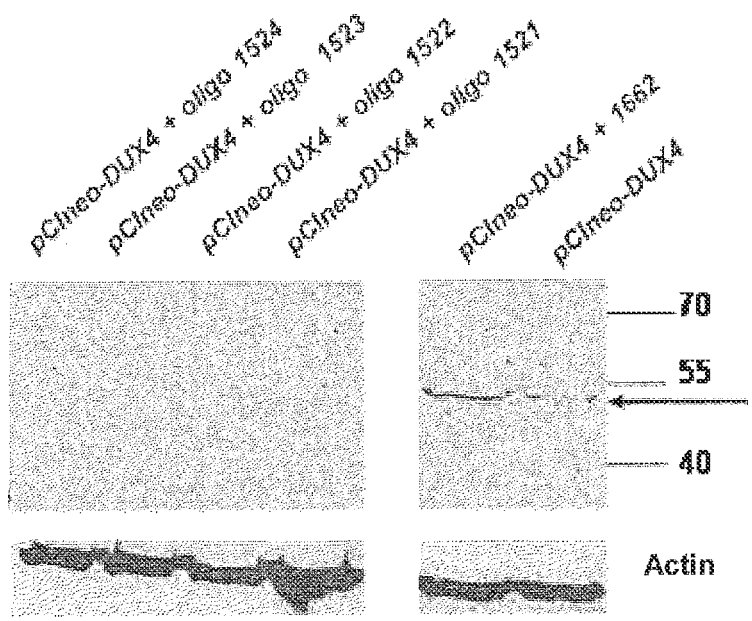
FIG. 9 illustrates the inhibitory effect of anti-DUX4 pre-mRNA antisense oligomers on DUX4 protein expression.
Figure 10:
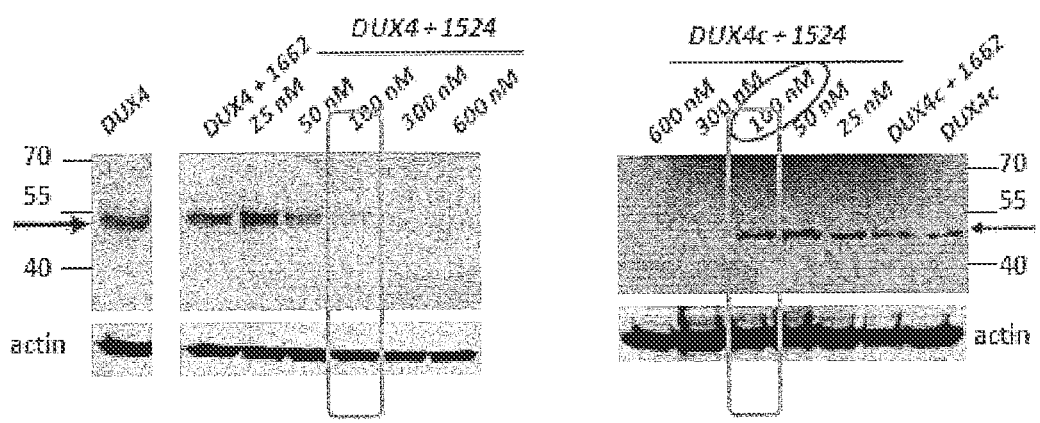
FIGS. 10 and 11 illustrate that antisense oligomer 1524 can exert a specific inhibitory effect on DUX4 protein expression.
Figure 11:
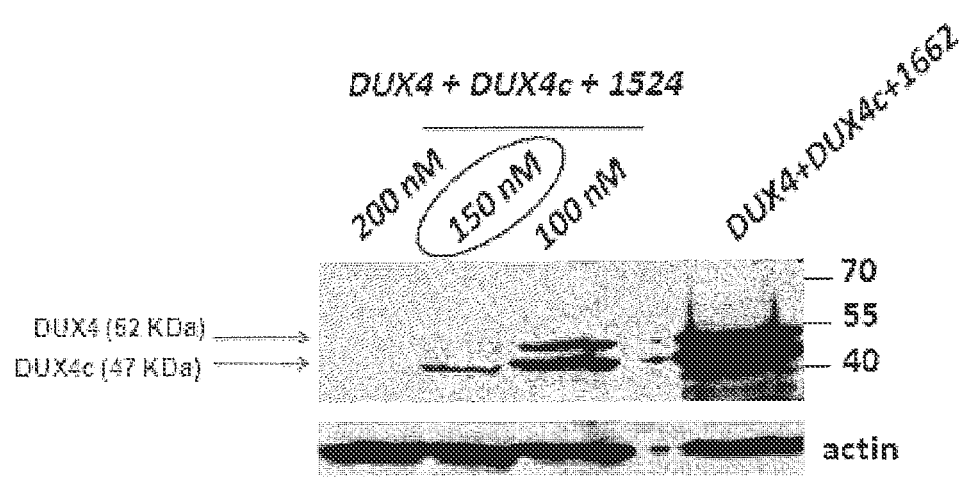

The results are shown in FIG. 9. No DUX4 protein (arrow) could be detected by Western blot using the 9A12 monoclonal antibody following the addition of different AO directed against the DUX4 pre-mRNA. In contrast the DUX4 protein was clearly expressed with the AO directed against the dystrophin pre-mRNA or in the absence of AO.
Testing C2C12 Mouse Myoblasts Transiently Expressing Dux4 or Dux4c Another experiment demonstrates, using the above-explained transient expression approach, that AO 1524 can achieve specific downregulation of DUX4 expression without affecting DUX4c protein expression (FIG. 10). C2C12 cells were transfected with either the expression vector pCIneo-DUX4 or pCIneo-DUX4c, alone or with different concentrations of AO 1524 targeting the DUX4 mRNA, or the negative control AO 1662 (concentration of 600 nM). DUX4 and DUX4c proteins were detected on a Western blot of cell protein extracts as described above. In this experiment 100 nM AO (boxed in FIG. 10) substantially suppressed DUX4 protein detection on the Western blot but did not affect DUX4c levels, thereby demonstrating specificity of the targeting by this AO.
Testing C2C12 Mouse Myoblasts Transiently Expressing Dux4 and Dux4c Similar results have been obtained in a co-transfection experiment in C2C12 cells using both DUX4 and DUX4c pCIneo expression vectors, so that both mRNAs were present simultaneously in the same cells. C2C12 cells were co-transfected with both pCIneo-DUX4 and pCIneo-DUX4c expression vectors, with different concentrations of AO 1524 targeting the DUX4 mRNA, or the negative control AO 1662 (600 nM). The DUX4 and DUX4c proteins were detected on a Western blot of cell protein extracts as described above. In this experiment 150 nM AO (FIG. 11) substantially suppressed DUX4 protein detection on the Western blot but did not affect DUX4c levels, thereby further corroborating specificity of the targeting by this AO.

Figure 12:
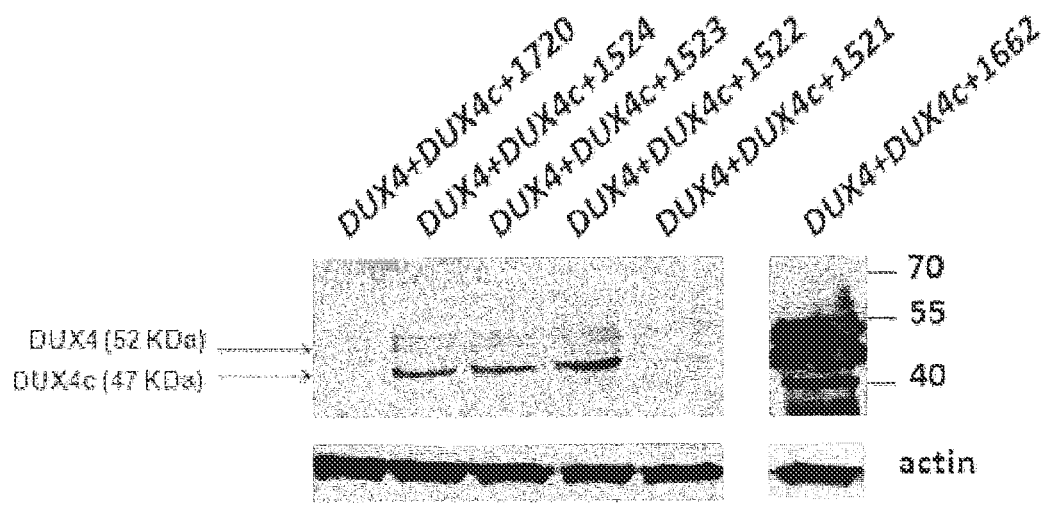
FIG. 12 illustrates that antisense oligomers 1524, 1523 and 1522 can exert a specific inhibitory effect on DUX4 protein expression.

In analogous co-transfection studies using the other AO, comparable specificity for DUX4 was also demonstrated for AO 1522 and 1523 (using 150 nM AO, see FIG. 12) and AO 1521 (using 50 nM AO, not shown). Moreover, lower concentrations in this experiment achieve comparable specificity for AO1719 and 1720.
Testing FSHD Primary Myoblasts Endogenously Expressing DUX4

To test the efficacy of AOs 1521 pLAM2A (−7+18) and 1523 pLAM3A (−12+13) on endogenous DUX4 expression, primary FSHD myoblasts were transfected with 50 nM 1521 pLAM2A (−7+18) or with 150 nM 1523 pLAM3A (−12+13) or with 600 nM of the negative control AO (nc-AO; JSR 1662 mGMCSF3A (−5+20)). Differentiation was induced 4 hours after transfection and three days later myotubes were lysed for total RNA extraction. Reverse transcription (RT) was performed on 500 ng of DNase-treated myotube total RNA using the FirstChoice®RLM-RACE kit (Ambion). 5 µl of the resulting cDNA were amplified by nested PCR with primers previously shown to be specific of the DUX4 mRNA 3'UTR (Dixit et al. 2007. supra). GAPDH mRNA amplification was used as an internal control. The RT-PCR products were analysed by electrophoresis on a 1% agarose gel. A densitometry of the bands was performed for quantification. Data were normalized to GAPDH mRNA levels.

Figure 29A:
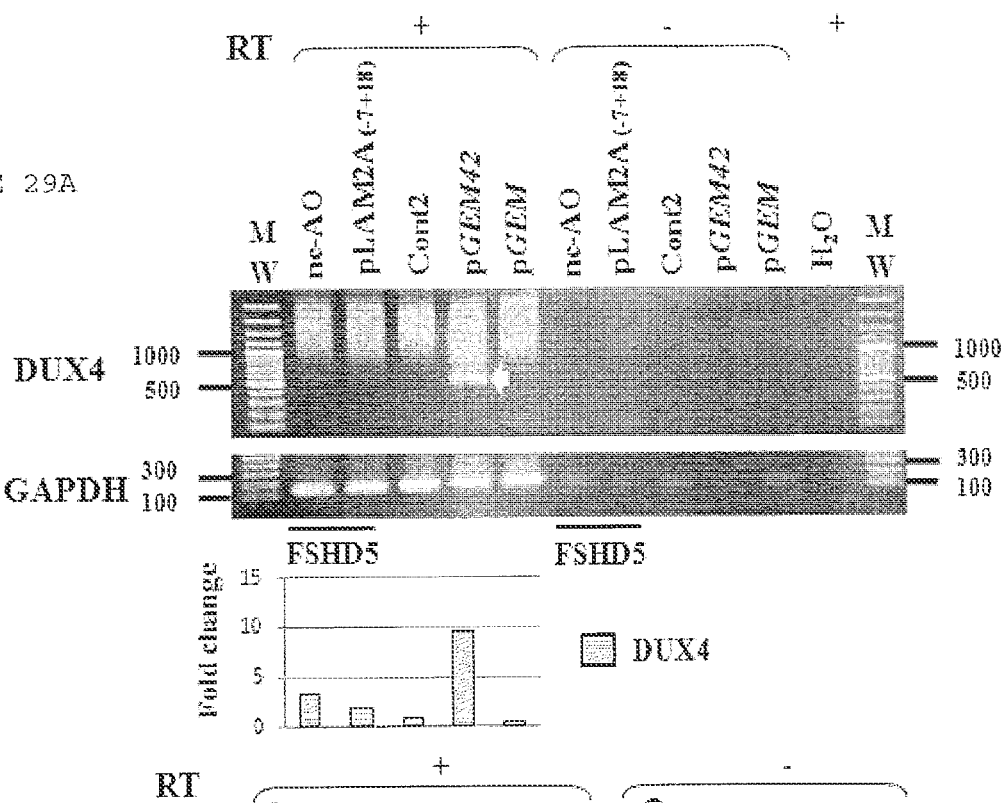
FIGS. 29A and 29B illustrate the efficiency of the antisense oligonucleotides 1521 (a) and 1523 (b) in decreasing endogenous DUX4 mRNA amount in FSHD primary myotubes.
Figure 29B:
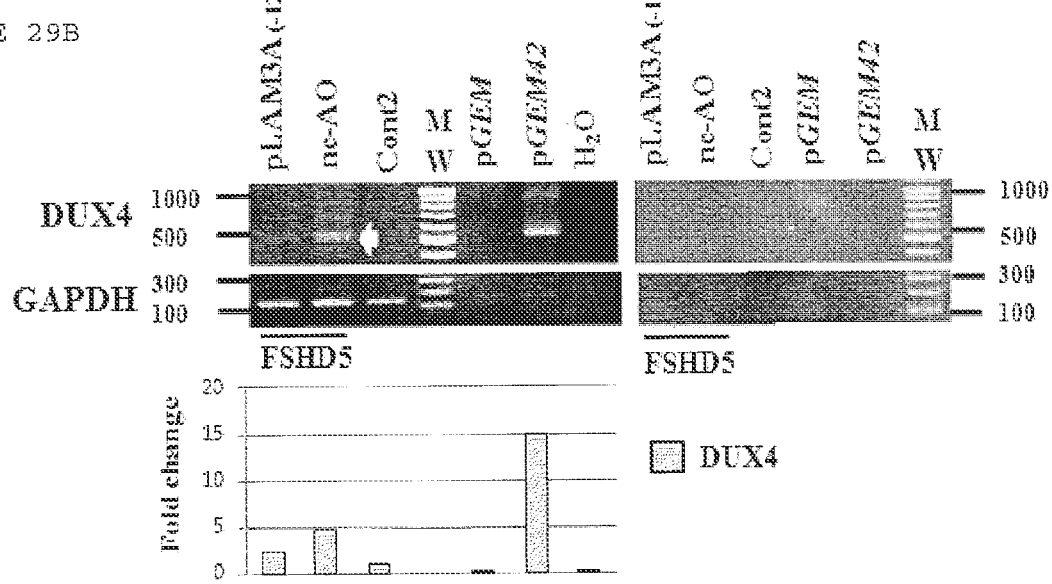

FIG. 29 shows that the expected 550 bp DNA fragment was detected in FSHD myotubes treated with nc-AO and at a 30% and 50% reduced intensity in cells treated with AOs 1521 pLAM2A (−7+18) (FIG. 29a) or 1523 pLAM3A (−12+13) (FIG. 29b), respectively. This amplicon was also observed in the positive control, i.e. C2C12 cells transfected with pGEM42, but not in the negative controls, i.e. either C2C12 cells transfected with the empty pGEM vector, or primary myoblasts from a healthy donor, or upon omission of reverse transcriptase. The RT-PCR products were cloned and sequenced to confirm DUX4 mRNA amplification (data not shown).

Example 2: siRNA (Small Interfering RNA) Directed Against 3'UTR Region of DUX4 or DUX4c mRNA Achieve Specific Silencing of DUX4 or DUX4c Expression Anti-DUX4 siRNA agents were developed based on and comprising the following DUX4 mRNA sequences:

```
siRNA-DUX41:
                              (SEQ ID NO: 47)
acaccuggcuggcuacgga siRNA-DUX42:
                              (SEQ ID NO: 48)
ggucuaggcccggugagag siRNA-DUX43:
                              (SEQ ID NO: 49)
ccuggauuagaguuacauc.
```

Anti-DUX4c siRNA agents were developed based on the following DUX4c mRNA sequences:

```
siRNA-DUX4c1:
                              (SEQ ID NO: 56)
ccagaguuucagcaaaagg;

siRNA-DUX4c2:
                              (SEQ ID NO: 57)
ggagggcugucauucuuuc;

siRNA-DUX4c3:
                              (SEQ ID NO: 58)
gcguucuucagucgaguug.
```

Cells were transfected using the "Silencer siRNA Starter Kit" (Ambion) containing the transfection agent SiPORT™ NeoFX™ (Ambion). TE671 cells (cells derived from a human alveolar rhabdomyosarcoma) were used for transfections, using the "reverse" method recommended by the supplier, in which the transfection reagent is introduced into the culture dish before seeding the cells. This method was three times superior than the traditional method in our hands. Transfection conditions were optimised using control anti-GAPDH siRNA supplied with the above kit. The optimised conditions included 2 µl SiPORT™ NeoFX™ reagent, 10 nM siRNA, and $5 \times 10^4$ cells/ml cell density.
Testing a TE671 Cell Line with an Inducible DUX4c Transgene The efficiency of siRNA directed against the DUX4c mRNA was tested using stable TE671-DUX4c lines established previously. These cells have incorporated the pAC1M2-DUX4c expression vector in which DUX4c transcription is inducible by doxycycline (DOX).

The cells were first transfected using the above conditions, which lead to only a weak DUX4c inhibition. Therefore the siRNA concentration was increased to 20 nM that was not toxic to the cells.

The cells were seeded at a density of $1\times10^5$ cells/well of a 6 well culture dish and transfected with siRNA-DUX4c1 20 nm ("si") by the reverse transfection method (Ambion). 4 hours after transfection, the expression of DUX4c was induced ("I") by adding 1 mg/ml of doxycycline in the culture medium. The 3rd or 5th day after induction, the cells were lysed and 20 µg of protein extracts were analyzed by SDS-PAGE electrophoresis (10%), and transferred to a nitrocellulose membrane. The membrane was incubated with the anti-DUX4c rabbit serum directed against a peptide in the carboxyterminal domain followed by a secondary antibody coupled to peroxidase and revealed with the kit LiteABlot® (Euroclone). DUX4c protein expression (nuclear staining) was also analysed by immunohistochemistry in TE-DUX4c cells transfected with siRNA-DUX4c1. The cells were transfected and DUX4c expression was induced as explained above. The 3rd or 5th day after induction, cells were fixed in PAF and incubated with anti-DUX4c rabbit serum and secondary antibodies coupled to a red dye (Alexa Fluor®). Pictures were taken under a fluorescence microscope after selecting a field where many cells were visible in white light.

Figure 13:
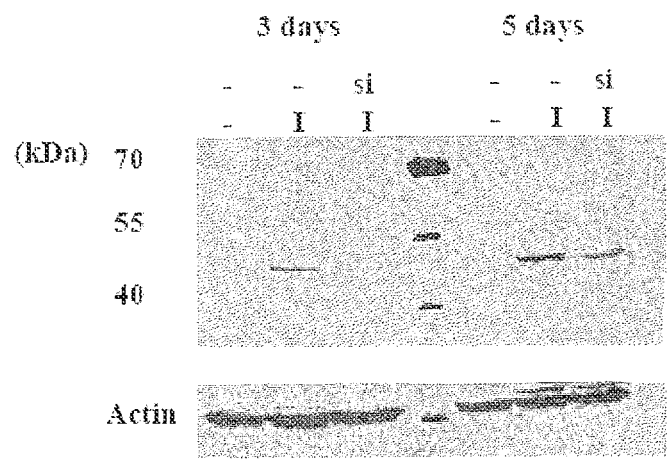
FIGS. 13A, 13B and 14 illustrate evaluation of siRNA targeting DUX4c.
Figure 13:
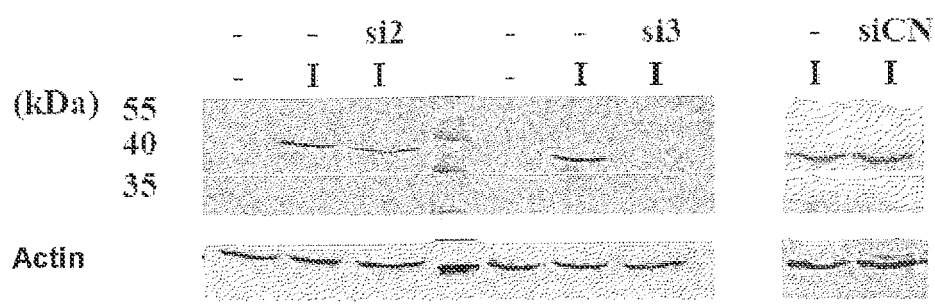

After three days, a significant decrease of the DUX4c protein amount could be observed in extracts from cells treated with siRNA 1 compared to untreated cells as well by Western blot (FIG. 13A) as by immunofluorescence (not shown). After five days, DUX4c expression increased again in the transfected cells (FIG. 13A), which could be explained by a possible degradation or dilution of the siRNA with time. Similar data has been obtained using siRNA-DUX4c 2 ("si2") or 3 ("si3") compared to a negative control siRNA ("SiCN") at 3rd day after induction of DUX4c expression (FIG. 13B).

Testing a TE671 Cell Line Transiently Expressing DUX4c

To confirm the results obtained on stable TE671-DUX4c line, we repeated the experiment on TE671 cells. We transfected cells with the siRNA and four hours later with the pCIneo-DUX4c expression vector which contains the strong cytomegalovirus promoter/enhancer.

The cells were transfected with siRNA-DUX4c 20 nM ("si1", "si2" and "si3") or negative control siRNA ("SiCN") using reverse transfection (Ambion) and 4 hours later with the pCIneo-DUX4c vector (DUX4c). The protein extracts were prepared and cells were fixed the third day after transfection of the pCIneo-DUX4c vector. The methodologies for the Western blot and immunofluorescence were as set out above.

Figure 14:
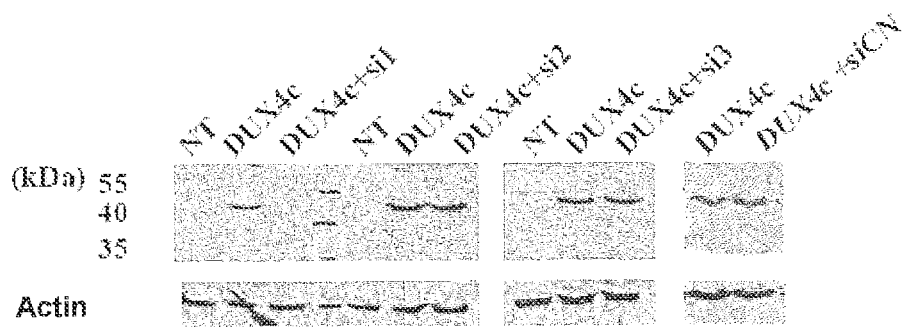

An inhibition of DUX4c expression similar to the previous experiment was observed by Western blot (FIG. 14) and immunofluorescence (not shown). We selected siRNA 1 as the most effective.

Testing a TE671 Cell Line Transiently Expressing DUX4

Figure 15:
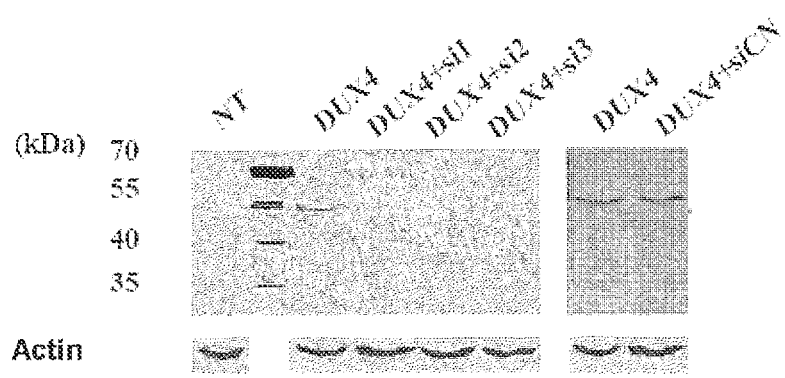
FIG. 15 illustrates evaluation of siRNA targeting DUX4.

Using similar methodology as in the previous section (except that the gel is a SDS-PAGE 12%, the primary antibody is the 9A12monoclonal antibody), we first transfected TE671 cells using the reverse transfection method with each of the three siRNA against DUX4. Four hours later we transfected these cells with the pCIneo-DUX4 expression vector. Three days after the second transfection, the DUX4 expression had completely disappeared in cells treated with siRNA as well on Western blot (FIG. 15) as in immunofluorescence (not shown). We selected the siRNA 3 for further studies as it targets a region particularly specific of DUX4.

Specificity of the Selected siRNAs

TE671 cells were transfected with siRNA-DUX4c ("siDUX4c") or siRNA-DUX4 ("siDUX4") (20 nM) using reverse transfection and 4 hours later with the pCIneo-DUX4 ("DUX4") or pCIneo-DUX4c ("DUX4c") expression vector. The protein extracts were prepared on the third day after pCIneo vectors transfection and revealed by Western blot with the 9A12 monoclonal antibody and secondary antibodies coupled to HRP. The antibodies were then stripped, and the same membrane developed with an anti-actin serum (internal control).

Figure 16:
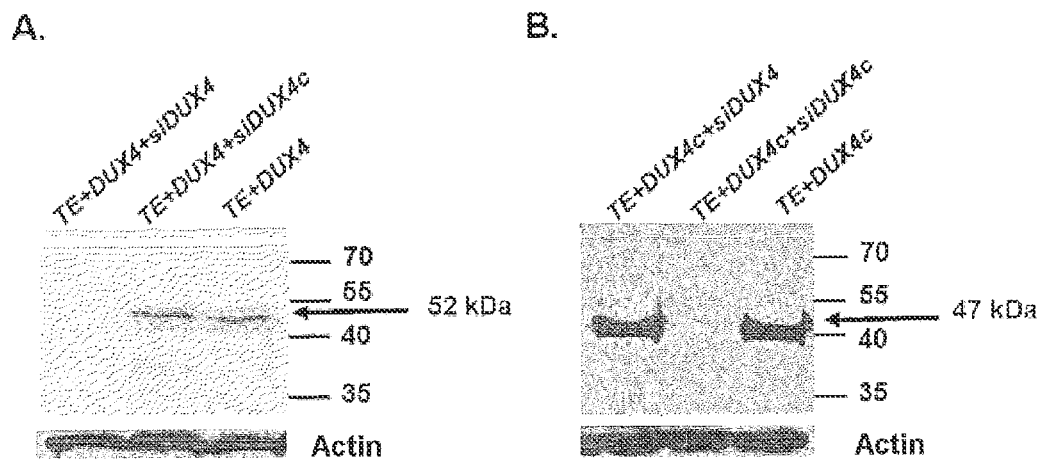
FIG. 16 illustrates evaluation of anti-DUX4c and anti-DUX4 siRNA specificity by Western blot. (A) anti-DUX4 antibody, (B) anti-DUX4c antibody.

The siRNA specificity was confirmed by the disappearance, in western blot, of bands corresponding to the molecular weight of DUX4 or DUX4c following the addition of their respective siRNA and not with the siRNA of their homologue (FIG. 16).

Construction of shRNA (Small Hairpin RNA) Vectors

Figure 17:
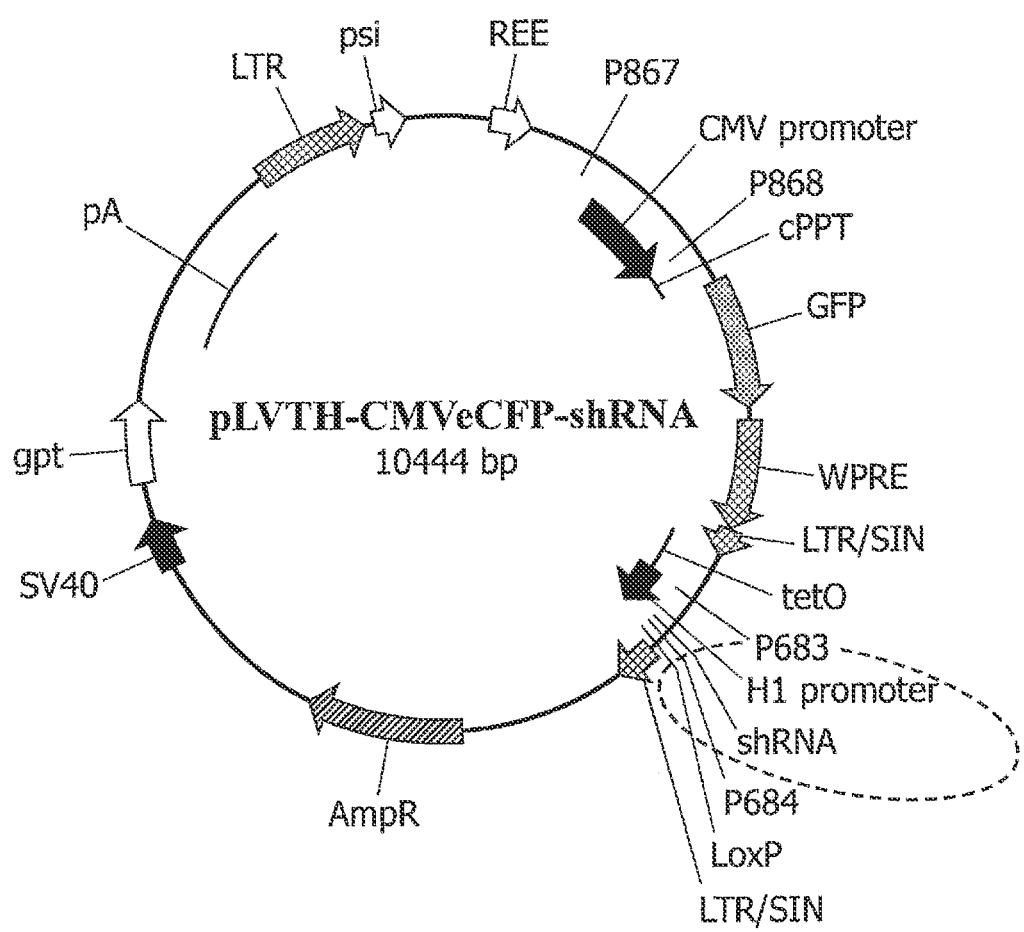
FIG. 17 illustrates pLVTH-shRNA expression vector.
Figure 18:
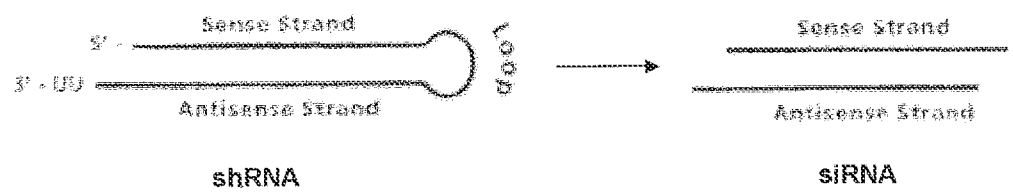
FIG. 18 schematically illustrates production of shRNA from an shRNA vector and its subsequence processing to siRNA by Dicer.

To test the effect of siRNA on FSHD myotubes, we used lentiviral vectors to produce shRNAs that are processed in the cell to yield identical siRNAs to those that we selected (FIG. 17). It has been previously demonstrated that myoblasts and myotubes could be efficiently transduced by such vectors. For this, synthetic DNA corresponding to the sequences of selected siRNA (sense sequence+loop (CTCGAG)+antisense sequence) were inserted into an expression vector containing the promoter of the histone H1 gene. Hence, the transcription unit contains the following element: H1 promoter ---CCGG(sense strand)loop(antisense strand)TTTTT---. Transcription produces shRNA which is processed to siRNA by Dicer (see FIG. 18). The H1-shRNA gene was sub-cloned in a pLVTH vector containing all the necessary elements for encapsidation.

Prior to encapsidation, we have checked the efficiency of pLVTH-shRNA vectors by Western blot on TE671 cells co-transfected with these vectors and with pCIneo-DUX4 or DUX4c expression vector.

Figure 19:
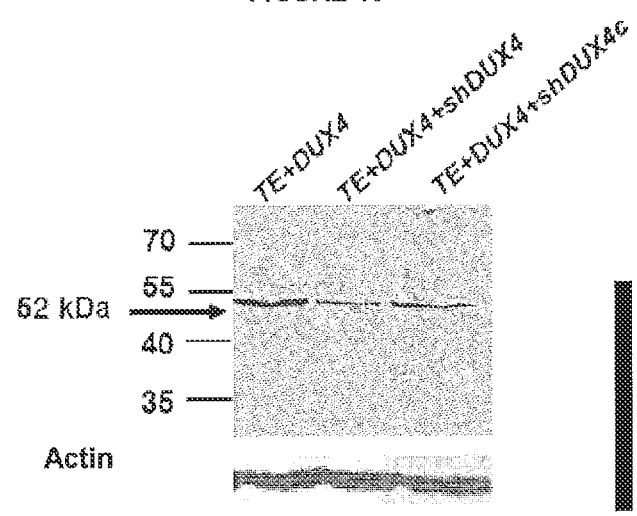
FIG. 19 illustrates efficiency and specificity of shRNA vectors in western blot.

FIG. 19 shows Western blot analysis of DUX4 protein expression on extracts of TE671 cells transfected with the pCIneo-DUX4 expression vector alone ("TE+DUX4") or with shRNA-DUX4 ("TE DUX4+shDUX4") or shRNA-DUX4c ("TE DUX4+shDUX4c") (Fugene 6, Roche Molecular Biochemical). 48 hours after transfection, proteins were extracted and 20 µg of these extracts were analyzed by SDS-PAGE electrophoresis (12%), then transferred to a nitrocellulose membrane. The membrane was incubated with 9A12 MAb followed by a secondary antibody coupled to peroxidase and revealed with the Lite-ABlot® kit (Euroclone). The antibodies were then stripped, and the same membrane revealed with an anti-actin serum (internal control). Immunofluorescence analysis of DUX4c protein expression (nuclear staining) in TE671 cells transfected with the pCIneo-DUX4c vector alone or with shRNA-DUX4 or shRNA-DUX4c was performed (Fugene 6). 48 hours after transfection, cells were fixed in 4% PAF and incubated with anti-DUX4c and a secondary antibody coupled to a red dye (Alexa Fluor®) (not shown).

A decrease in intensity of the band corresponding to 52 kDa DUX4 (FIG. 19) and of the DUX4c signal in immunofluorescence (not shown) was confirmed following the addition of their respective shRNA.

Once their efficiency was proven, we encapsidated the pLVTH-shRNA vectors. We then co-transduced immortal control myoblasts with recombinant lentivirus expressing either DUX4 or DUX4c and recombinant lentivirus expressing their respective shRNA. 72 hours after transduction, we detected by immunofluorescence the DUX4 and DUX4c proteins using monoclonal antibody 9A12. The presence of shRNA in the cells is confirmed by the expression of GFP encoded by the shRNA vector.

After 72 hours, a decreased expression of both proteins following the addition of their respective shRNA was visible by immunofluorescence (not shown).

Testing FSHD Primary Myoblasts Endogenously Expressing DUX4

Figure 22:
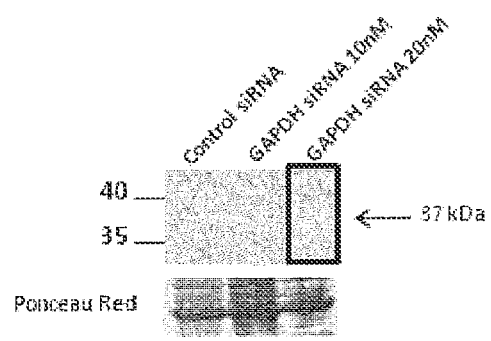
FIG. 22 illustrates optimal transfection conditions for FSHD primary myoblasts.

Human FSHD primary myoblasts, which are difficult to transfect, were transfected following the reverse transfection method as described above using the "Silencer siRNA Starter Kit" (Ambion). Optimal transfection conditions, defining an effective transfection reagent with low cytotoxicity for human primary myoblasts, were set up using control anti-GAPDH siRNA supplied with the above kit. 72 hours after transfection, cells were harvested and 10 μg of protein extracts were separated by SDS-PAGE (12%) and transferred to a nitrocellulose membrane. The protein transfer was confirmed by staining the membrane with Ponceau red. After rinsing the membrane, it was incubated with anti-GAPDH monoclonal antibody, followed by a secondary antibody coupled to horseradish peroxidase and revealed with the Lumilight substrate (Roche) followed by detection on a photographic film. Optimal transfection conditions included 4 μl SiPORT™ NeoFX™ reagent, 20 nM siRNA, and a cell density of $10^5$ cells in a 35 mm culture dish (FIG. 22).

To test the efficiency of siRNA directed against the DUX4 mRNA, we transfected FSHD primary myoblasts with the siRNA using the transfection conditions specified above.

The cells were seeded at a density of $10^5$ cells in a 35 mm culture dish and transfected with control siRNA or DUX4-siRNA3 following the reverse transfection method using 4 μl SiPORT™ NeoFX™ reagent. 3 different DUX4-siRNA3 concentrations were tested (10 nM, 20 nM and 30 nM) to determine the best concentration to use to reduce the endogenous DUX4 expression. Since the DUX4 protein is only detectable in myotubes, 4 hours after transfection, myoblasts differentiation was induced by replacing the culture medium by a medium without serum. Cells were harvested 72 h after differentiation and nuclear protein extracts were realised. 20 μg of these nuclear protein extracts and 5 μg of nuclear protein extract of TE671 cells that were transfected with the pCIneo-DUX4 expression vector (TE-DUX4), which was used as a positive control, were separated by SDS-PAGE (12%) and transferred onto a nitrocellulose membrane. Protein transfer was confirmed by staining the membrane with Ponceau red (not shown). After rinsing the membrane, it was incubated with the 9A12 monoclonal antibody followed by a secondary antibody coupled to horseradish peroxidase and revealed with the Femto Super Signal kit (Pierce) followed by detection on a photographic film. The antibodies were then stripped and the same membrane was immunostained with a TBP monoclonal antibody as a nuclear loading control.

Figure 23:
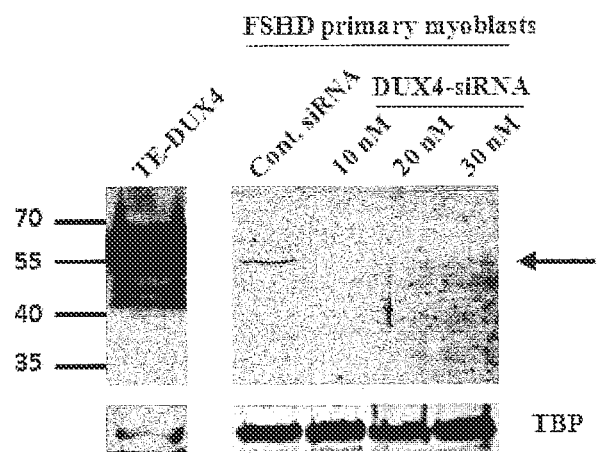
FIG. 23 illustrates evaluation of siRNA targeting DUX4 in FSHD primary myoblasts.
Figure 24:
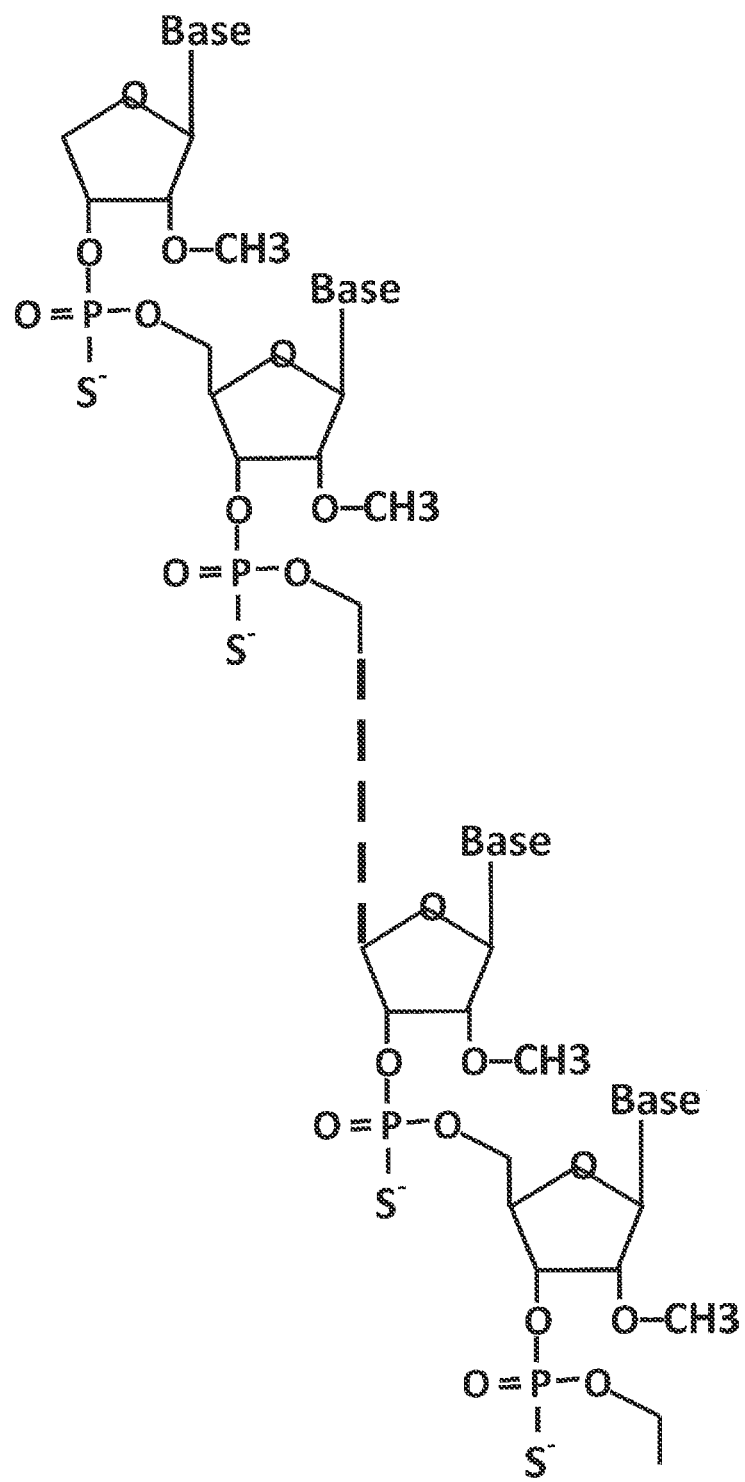
FIG. 24 illustrates a schematic representation of the structure of an oligonucleotide chemically modified with a 2'-O-methylated phosphorothioate backbone.
Figure 25:
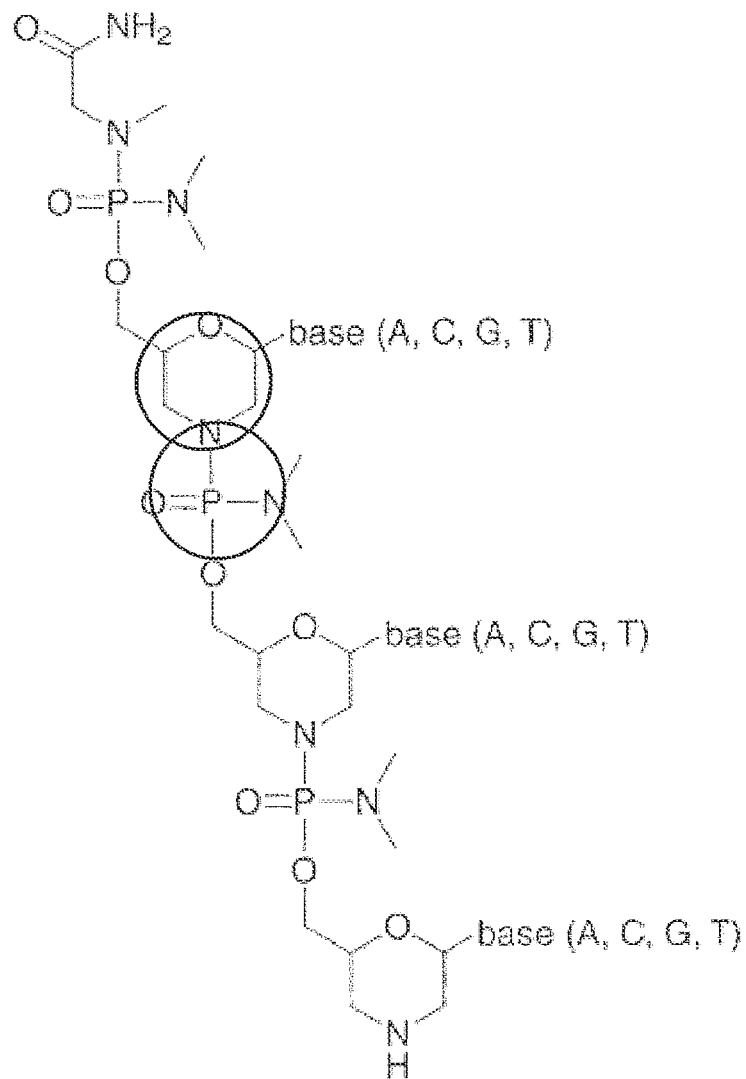
FIG. 25 illustrates a schematic representation of the structure of an oligonucleotide chemically modified with a phosphorodiamidate morpholino backbone.

After three days, a significant decrease of the DUX4 protein amount, as indicated by the red arrow, could be observed in protein extracts from cells treated with DUX4-siRNA compared to cells treated with the control siRNA by Western blot (FIG. 23).

The efficiency of the siRNA targeting the DUX4 mRNA was confirmed by RT-PCR as a decrease of endogenous DUX4 mRNA amount in FSHD primary myotubes. FSHD primary myoblasts were transfected with 10 nM DUX4-siRNA 3 or control siRNA (30 nM) using the transfection conditions specified above. 4 hours after transfection, myoblast differentiation was induced as specified above. Following differentiation for 3 days, total RNA was extracted from the myotubes. Reverse transcription (RT) was performed on 500 ng of DNase-treated myotube total RNA using the FirstChoice®RLM-RACE kit (Ambion). 5 μl of the resulting cDNA were amplified by nested PCR with primers previously shown to be specific of the DUX4 mRNA 3' UTR (Dixit et al. 2007. supra). GAPDH mRNA amplification was used as an internal control. The RT-PCR products were analysed by electrophoresis on a 1% agarose gel. A densitometry of the bands was performed for quantification. Data were normalized to GAPDH mRNA levels.

Figure 30:
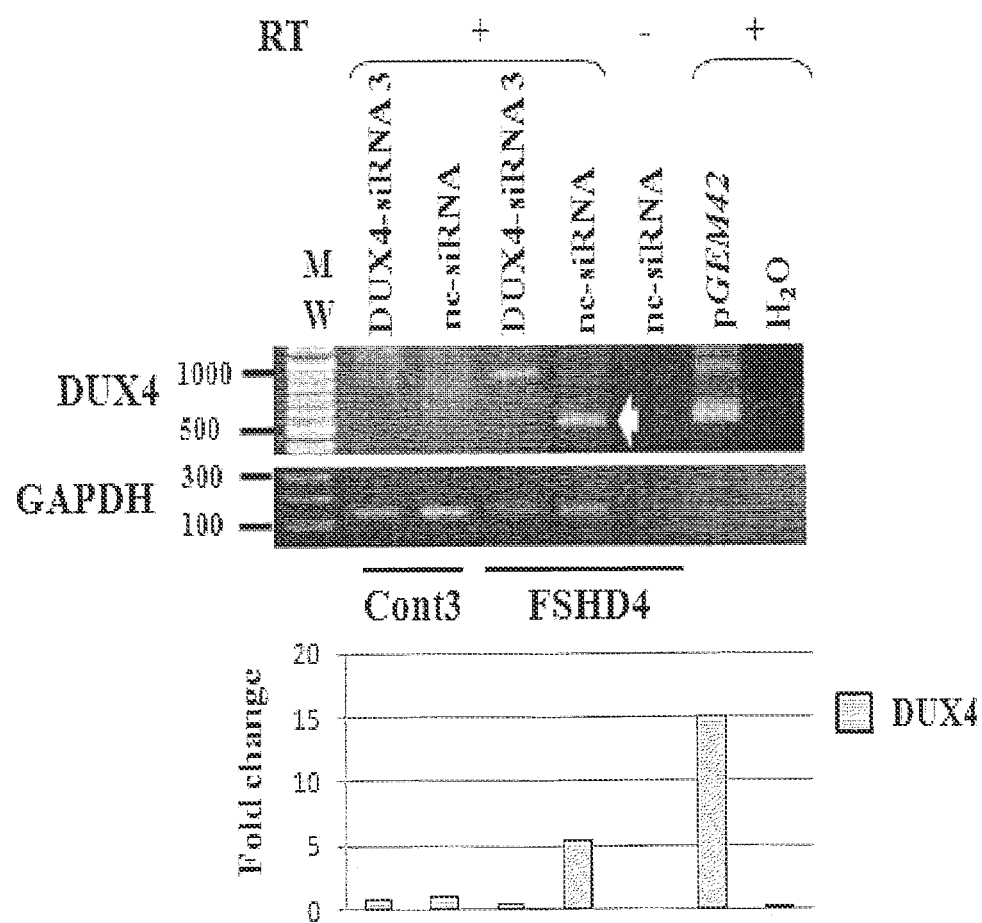
FIG. 30 illustrates the efficiency of anti-DUX4 siRNA3 in decreasing endogenous DUX4 mRNA amount in FSHD primary myotubes.

As shown in FIG. 30, the expected 550 bp DNA fragment was detected in FSHD myotubes transfected with the control siRNA (nc-siRNA) and at a 80% reduced intensity in cells treated with the DUX4-siRNA 3. This amplicon was also observed in the positive control i.e. C2C12 cells transfected with the pGEM42 vector containing two D4Z4 units (Gabriéls et al. 1999. supra) but not in primary myoblasts from a healthy donor (Cont), or upon omission of reverse transcriptase. The RT-PCR products were cloned and sequenced to confirm DUX4 mRNA amplification (data not shown).

Example 3: Further Antisense Oligonucleotides Directed Against DUX4 Pre-mRNA

Two further antisense oligomers (AO) directed against the DUX4 pre-mRNA were designed based on the DUX4 gene sequence. One of these AOs, JSR 2245 pLAM polyA (−13+6), is capable of binding to a sequence element required for polyadenylation of the DUX4 mRNA. The other AO, JSR 2250 pLAM1D (+7-18 around exon-1 intron-1 boundary), is capable of binding to a sequence element located in the 3' untranslated sequence of the DUX4 mRNA between the stop codon and the first intron (see FIG. 31). Whereas JSR 2250 pLAM1D binds to an exon-intron boundary, it does not in an initial experiment appear to interfere with splicing of DUX4.

```
JSR 2245 pLAM polyA (-13+6):
                              (SEQ ID NO: 65)
GGGCAUUUUAAUAUAUCUCUGAACU JSR 2250 pLAM1D (+7-18):
                              (SEQ ID NO: 64)
ACCCGACCCCGUCCCAACCCCGCGU
```

Both AOs had 2'-O-methyl-phosphorothioate backbone.

The efficacy of both AOs, JSR 2245 and JSR 2250, was evaluated in transient expression in C2C12 mouse myoblasts grown in vitro that were co-transfected with both DUX4 and DUX4c pCIneo expression vectors, so that both mRNAs were present simultaneously in the same cells.

$10^5$ C2C12 mouse myoblasts were seeded per well of 6-well dishes and grown at 37° C. and 5% $CO_2$ in DMEM, 10% foetal bovine serum gold (PAA), 1% antibiotics (penicillin, streptomycin, fungizon). They were co-transfected 24 hours later with 500 ng per well of the expression vectors pCIneo-DUX4 and pCIneo-DUX4c combined with the indicated AO. As the 150 nM concentration seemed to be most effective in previous experiments (see Example 1), we tested the effect of the AOs 2245 and 2250 targeting the DUX4 mRNA using this concentration. The negative control was AO 1662 that targets the dystrophin mRNA and was used at a concentration of 600 nM. The transfection reagent was Lipofectamine™ 2000 (Invitrogen) used at a ratio of 1 μg AO/1 μl reagent. The cells were lysed 24 hours after transfection, and total protein extracts were prepared in NuPAGE® LDS sample buffer (Invitrogen). 15 μg of protein extracts were separated by electrophoresis (SDS-PAGE 12%), and transferred to a nitrocellulose membrane. DUX4 (52 kDa) was detected on this Western blot with the 9A12 monoclonal antibody followed by anti-mouse IgG antibodies coupled to peroxidase (HRP), and revealed with Lumi-Light kit (Roche) detected on a film. After striping these antibodies, the same membrane was incubated with an anti-actin antibody to provide a loading control.

Figure 32:
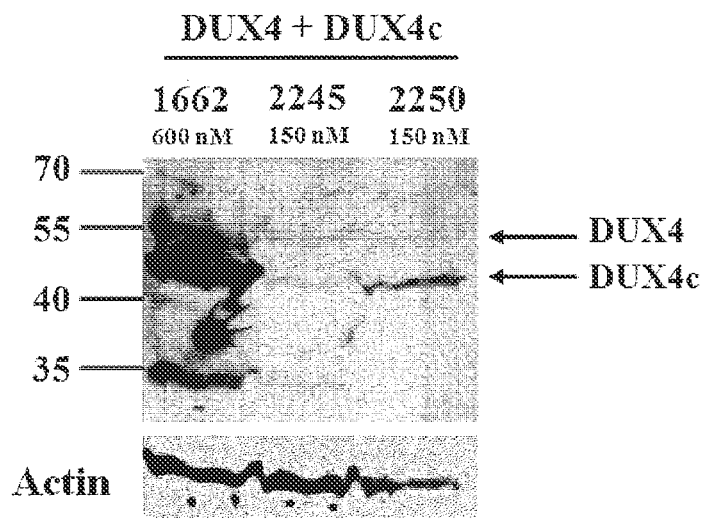
FIG. 32 illustrates the inhibitory effect of the antisense oligomers 2245 and 2250 on DUX4 protein expression.

The results are shown in FIG. 32. In the conditions as specified above, AO 2250 could strongly reduce DUX4 levels as compared to the negative control AO 1662 while DUX4c was still expressed. In contrast AO 2245 suppressed both DUX4 and DUX4c proteins at this concentration, suggesting that yet lower amounts may need to be used in case specific targeting of DUX4 production is intended (FIG. 32).

Figure 33:
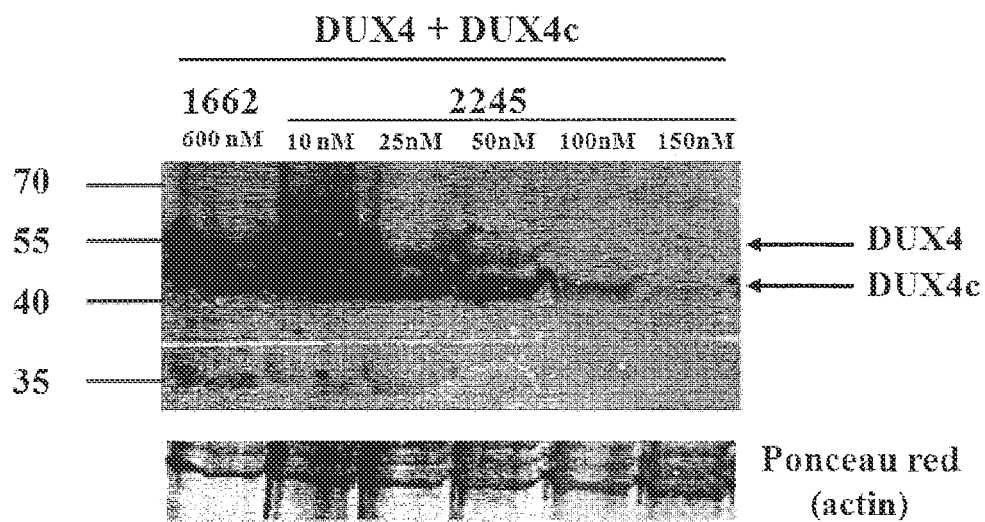
FIG. 33 illustrates optimal concentration of antisense oligomer 2245 for specific inhibition of DUX4 protein expression.

In a similar experiment, AO 2245 was used at a concentration of 10, 25, 50, 100 or 150 nM. The optimal concentration for specifically inhibiting DUX4 protein expression was found to be 50 nM (FIG. 33).

What is claimed is:

1. An oligonucleotide of 20 to 30 nucleotides in length that comprises at least 20 consecutive nucleotides that are complementary to the nucleotide sequence set forth as SEQ ID NO: 12 (CTTCCTGGCTAGACCTGCGCGCAGT), wherein the oligonucleotide comprises one or more modifications.

2. The oligonucleotide of claim 1, wherein the oligonucleotide is perfectly complementary to the nucleotide sequence set forth as SEQ ID NO: 12 (CTTCCTGGCTAGACCTGCGCGCAGT).

3. The oligonucleotide of claim 1, wherein the oligonucleotide comprises at least 20 consecutive nucleotides of SEQ ID NO: 18 (ACUGCGCGCAGGUCUAGCCAGGAAG).

4. The oligonucleotide of claim 1, wherein the oligonucleotide comprises at least 20 consecutive nucleotides of SEQ ID NO: 18 (ACUGCGCGCAGGUCUAGCCAGGAAG), wherein one or more uracil bases are replaced by thymine bases.

5. The oligonucleotide of claim 1, wherein the oligonucleotide comprises the nucleotide sequence set forth as SEQ ID NO: 18 (ACUGCGCGCAGGUCUAGCCAGGAAG), wherein one or more uracil bases are replaced by thymine bases.

6. The oligonucleotide of claim 1, wherein the oligonucleotide comprises the nucleotide sequence set forth as SEQ ID NO: 18 (ACUGCGCGCAGGUCUAGCCAGGAAG), wherein each uracil bases is replaced by a thymine base.

7. The oligonucleotide of claim 1, wherein the one or more modifications comprises a phosphorodiamidate morpholino backbone modification.

8. The oligonucleotide of claim 7, wherein each of the one or more modifications is a phosphorodiamidate morpholino backbone modification.

9. The oligonucleotide of claim 8, wherein the oligonucleotide is a phosphorodiamidate morpholino oligomer (PMO).

10. The oligonucleotide of claim 1, wherein the one or more modifications comprises a 2'—O—methoxyethyl sugar modification.

11. The oligonucleotide of claim 10, wherein each of the one or more modifications is a 2'—O—methoxyethyl sugar modification.

12. The oligonucleotide of claim 1, wherein the oligonucleotide is conjugated to a moiety that enhances the cellular uptake of the oligonucleotide.

13. The oligonucleotide of claim 12, wherein the moiety enhances uptake of the oligonucleotide into muscle cells.

14. The oligonucleotide of claim 13, wherein the moiety is a cell-penetrating peptide.

15. The oligonucleotide of claim 9, wherein the oligonucleotide is conjugated to a moiety that enhances the cellular uptake of the oligonucleotide.

16. The oligonucleotide of claim 15, wherein the moiety enhances uptake of the oligonucleotide into muscle cells.

17. A method for reducing the expression of DUX4 in a cell, comprising delivering the oligonucleotide of claim 1 to the cell in an amount effective to reduce expression of DUX4 in the cell.

18. The method of claim 17, wherein the cell is in vitro.

19. The method of claim 17, wherein the cell is in a subject.

20. The method of claim 17, wherein the cell is a muscle cell.

21. The method of claim 20, wherein the muscle cell is a muscle cell of a subject having facioscapulohumeral muscular dystrophy (FSHD).

22. The method of claim 21, wherein the subject is a human subject.

23. A method for reducing the expression of DUX4 in a cell, the method comprising delivering the oligonucleotide of claim 9 to the cell in an amount effective to reduce expression of DUX4 in the cell.

24. The method of claim 23, wherein the cell is in vitro.

25. The method of claim 23, wherein the cell is in a subject.

26. The method of claim 23, wherein the cell is a muscle cell.

27. The method of claim 26, wherein the muscle cell is a muscle cell of a subject having facioscapulohumeral muscular dystrophy (FSHD).

28. The method of claim 27, wherein the subject is a human subject.

29. The method of claim 23, wherein the oligonucleotide is conjugated to a moiety that enhances the cellular uptake of the oligonucleotide.

30. The method of claim 29, wherein the moiety enhances uptake of the oligonucleotide into muscle cells.

* * * * *

SEQUENCE LISTING

<160> NUMBER OF SEQ ID NOS: 69

<210> SEQ ID NO 1
<211> LENGTH: 1080
<212> TYPE: DNA
<213> ORGANISM: Homo sapiens

<400> SEQUENCE: 1

```
agaaacggag gccccggggg agctggaggc ctcggaagag gccgcctcgc tggaagcacc      60
cctcagcgag gaagaatacc gggctctgct ggaggagctt taggacgcgg ggttgggacg     120
gggtcgggtg gttcggggca gggccgtggc ctctctttcg cggggaacac ctggctggct    180
acggaggggc gtgtctccgc cccgccccct ccaccgggct gaccggcctg ggattcctgc    240
cttctaggtc taggcccggt gagagactcc acaccgcgga gaactgccat tctttcctgg    300
gcatcccggg gatcccagag ccggcccagg tacctgcgca cgcgcgggtt tgcgggcagc    360
cgcctgggct gtgggagcag cccgggcaga gctctcctgc ctctccacca gcccaccccg    420
ccgcctgacc gccccctccc cacccccac ccccaccccc cggaaaacgc gtcgtcccct     480
gggctgggtg gagaccccg tcccgcgaaa caccgggccc cgcgcagcgt ccgggcctga     540
ctccgctccg gcggctcgcc tcctgtgtgc ccccgcgcca ccgtcgcccg cccgcccggg    600
cccctgcagc ctcccagctg ccagcgcgga gctcctggcg gtcaaaagca tacctctgtc    660
tgtctttgcc cgcttcctgg ctagacctgc gcgcagtgcg caccccggct gacgtgcaag    720
ggagctcgct ggcctctctg tgcccttgtt cttccgtgaa attctggctg aatgtctccc    780
cccaccttcc gacgctgtct aggcaaacct ggattagagt tacatctcct ggatgattag    840
ttcagagata tattaaaatg ccccctccct gtggatccta tagaagattt gcatcttttg    900
tgtgatgagt gcagagatat gtcacaatat cccctgtaga aaaagcctga aattggttta    960
cataacttcg gtgatcagtg cagatgtgtt tcagaactcc atagtagact gaacctagag   1020
aatggttaca tcacttaggt gatcagtgta gagatatgtt aaaattctcg tgtagacaga   1080
```

<210> SEQ ID NO 2
<211> LENGTH: 60
<212> TYPE: DNA
<213> ORGANISM: Homo sapiens

<400> SEQUENCE: 2

```
ggctctgctg gaggagcttt aggacgcggg gttgggacgg ggtcgggtgg ttcggggcag      60
```

<210> SEQ ID NO 3
<211> LENGTH: 40
<212> TYPE: DNA
<213> ORGANISM: Homo sapiens

<400> SEQUENCE: 3

```
gaggagcttt aggacgcggg gttgggacgg ggtcgggtgg                            40
```

<210> SEQ ID NO 4
<211> LENGTH: 60

<212> TYPE: DNA
<213> ORGANISM: Homo sapiens

<400> SEQUENCE: 4
gctgaccggc ctgggattcc tgccttctag gtctaggccc ggtgagagac tccacaccgc    60

<210> SEQ ID NO 5
<211> LENGTH: 40
<212> TYPE: DNA
<213> ORGANISM: Homo sapiens

<400> SEQUENCE: 5
ctgggattcc tgccttctag gtctaggccc ggtgagagac                          40

<210> SEQ ID NO 6
<211> LENGTH: 60
<212> TYPE: DNA
<213> ORGANISM: Homo sapiens

<400> SEQUENCE: 6
ggcatcccgg ggatcccaga gccggcccag gtacctgcgc acgcgcgggt ttgcgggcag    60

<210> SEQ ID NO 7
<211> LENGTH: 40
<212> TYPE: DNA
<213> ORGANISM: Homo sapiens

<400> SEQUENCE: 7
ggatcccaga gccggcccag gtacctgcgc acgcgcgggt                          40

<210> SEQ ID NO 8
<211> LENGTH: 60
<212> TYPE: DNA
<213> ORGANISM: Homo sapiens

<400> SEQUENCE: 8
tctgtctgtc tttgcccgct tcctggctag acctgcgcgc agtgcgcacc ccggctgacg    60

<210> SEQ ID NO 9
<211> LENGTH: 40
<212> TYPE: DNA
<213> ORGANISM: Homo sapiens

<400> SEQUENCE: 9
tttgcccgct tcctggctag acctgcgcgc agtgcgcacc                          40

<210> SEQ ID NO 10
<211> LENGTH: 25
<212> TYPE: DNA
<213> ORGANISM: Homo sapiens

<400> SEQUENCE: 10
cttctaggtc taggcccggt gagag                                          25

<210> SEQ ID NO 11
<211> LENGTH: 25
<212> TYPE: DNA
<213> ORGANISM: Homo sapiens

<400> SEQUENCE: 11
tggctagacc tgcgcgcagt gcgca                                          25

<210> SEQ ID NO 12

```
<211> LENGTH: 25
<212> TYPE: DNA
<213> ORGANISM: Homo sapiens

<400> SEQUENCE: 12
cttcctggct agacctgcgc gcagt                                          25

<210> SEQ ID NO 13
<211> LENGTH: 25
<212> TYPE: DNA
<213> ORGANISM: Homo sapiens

<400> SEQUENCE: 13
agacctgcgc gcagtgcgca ccccg                                          25

<210> SEQ ID NO 14
<211> LENGTH: 30
<212> TYPE: DNA
<213> ORGANISM: Homo sapiens

<400> SEQUENCE: 14
cttcctggct agacctgcgc gcagtgcgca                                     30

<210> SEQ ID NO 15
<211> LENGTH: 30
<212> TYPE: DNA
<213> ORGANISM: Homo sapiens

<400> SEQUENCE: 15
gcccgcttcc tggctagacc tgcgcgcagt                                     30

<210> SEQ ID NO 16
<211> LENGTH: 25
<212> TYPE: RNA
<213> ORGANISM: Artificial
<220> FEATURE:
<223> OTHER INFORMATION: DUX4 antisense agent

<400> SEQUENCE: 16
cucucaccgg gccuagaccu agaag                                          25

<210> SEQ ID NO 17
<211> LENGTH: 25
<212> TYPE: RNA
<213> ORGANISM: Artificial
<220> FEATURE:
<223> OTHER INFORMATION: DUX4 antisense agent

<400> SEQUENCE: 17
ugcgcacugc gcgcaggucu agcca                                          25

<210> SEQ ID NO 18
<211> LENGTH: 25
<212> TYPE: RNA
<213> ORGANISM: Artificial
<220> FEATURE:
<223> OTHER INFORMATION: DUX4 antisense agent

<400> SEQUENCE: 18
acugcgcgca ggucuagcca ggaag                                          25

<210> SEQ ID NO 19
<211> LENGTH: 25
<212> TYPE: RNA
<213> ORGANISM: Artificial
```

```
<220> FEATURE:
<223> OTHER INFORMATION: DUX4 antisense agent

<400> SEQUENCE: 19
cggggugcgc acugcgcgca ggucu                                              25

<210> SEQ ID NO 20
<211> LENGTH: 30
<212> TYPE: RNA
<213> ORGANISM: Artificial
<220> FEATURE:
<223> OTHER INFORMATION: DUX4 antisense agent

<400> SEQUENCE: 20
ugcgcacugc gcgcaggucu agccaggaag                                         30

<210> SEQ ID NO 21
<211> LENGTH: 30
<212> TYPE: RNA
<213> ORGANISM: Artificial
<220> FEATURE:
<223> OTHER INFORMATION: DUX4 antisense agent

<400> SEQUENCE: 21
acugcgcgca ggucuagcca ggaagcgggc                                         30

<210> SEQ ID NO 22
<211> LENGTH: 60
<212> TYPE: DNA
<213> ORGANISM: Homo sapiens

<400> SEQUENCE: 22
acctccccac agcccacagc tcttgtcata gtgcgggaat agtgttctat cactacagga        60

<210> SEQ ID NO 23
<211> LENGTH: 40
<212> TYPE: DNA
<213> ORGANISM: Homo sapiens

<400> SEQUENCE: 23
agcccacagc tcttgtcata gtgcgggaat agtgttctat                              40

<210> SEQ ID NO 24
<211> LENGTH: 60
<212> TYPE: DNA
<213> ORGANISM: Homo sapiens

<400> SEQUENCE: 24
gcagagagga aagcggtctt ccgcctccag ggccagcggg acctcgcact ccgggaaaac        60

<210> SEQ ID NO 25
<211> LENGTH: 40
<212> TYPE: DNA
<213> ORGANISM: Homo sapiens

<400> SEQUENCE: 25
aagcggtctt ccgcctccag ggccagcggg acctcgcact                              40

<210> SEQ ID NO 26
<211> LENGTH: 60
<212> TYPE: DNA
<213> ORGANISM: Homo sapiens

<400> SEQUENCE: 26
```
gctcaccagc cctccggatc gccggcccgg gtcacttcat cccggagcaa ttcggacgaa    60

<210> SEQ ID NO 27
<211> LENGTH: 40
<212> TYPE: DNA
<213> ORGANISM: Homo sapiens

<400> SEQUENCE: 27
cctccggatc gccggcccgg gtcacttcat cccggagcaa    40

<210> SEQ ID NO 28
<211> LENGTH: 60
<212> TYPE: DNA
<213> ORGANISM: Homo sapiens

<400> SEQUENCE: 28
cgggttccac gctccttcgc cctctgcaag gggacctgtt gctcgcgtgt ctcccgcccc    60

<210> SEQ ID NO 29
<211> LENGTH: 40
<212> TYPE: DNA
<213> ORGANISM: Homo sapiens

<400> SEQUENCE: 29
gctccttcgc cctctgcaag gggacctgtt gctcgcgtgt    40

<210> SEQ ID NO 30
<211> LENGTH: 60
<212> TYPE: DNA
<213> ORGANISM: Homo sapiens

<400> SEQUENCE: 30
ttgcaggaaa caggaatccg tggtcaggcc gtgatgcacc cgacgtttct tttctctgca    60

<210> SEQ ID NO 31
<211> LENGTH: 40
<212> TYPE: DNA
<213> ORGANISM: Homo sapiens

<400> SEQUENCE: 31
caggaatccg tggtcaggcc gtgatgcacc cgacgtttct    40

<210> SEQ ID NO 32
<211> LENGTH: 60
<212> TYPE: DNA
<213> ORGANISM: Homo sapiens

<400> SEQUENCE: 32
agtcaagaca gcggcttcca gtttccatag aattactgga gaacctcaga gagccagccc    60

<210> SEQ ID NO 33
<211> LENGTH: 40
<212> TYPE: DNA
<213> ORGANISM: Homo sapiens

<400> SEQUENCE: 33
gcggcttcca gtttccatag aattactgga gaacctcaga    40

<210> SEQ ID NO 34
<211> LENGTH: 60
<212> TYPE: DNA
<213> ORGANISM: Homo sapiens

<400> SEQUENCE: 34

```
gaagaacacc gggctctgct ggaggagcag gttggagcgg ggttggggcg gggtggggc      60

<210> SEQ ID NO 35
<211> LENGTH: 40
<212> TYPE: DNA
<213> ORGANISM: Homo sapiens

<400> SEQUENCE: 35
gggctctgct ggaggagcag gttggagcgg ggttggggcg                           40

<210> SEQ ID NO 36
<211> LENGTH: 60
<212> TYPE: DNA
<213> ORGANISM: Homo sapiens

<400> SEQUENCE: 36
ctggattcca cgtttctttg ccctctgcag aggtgcctgt tgctcaagtc tctgccccg      60

<210> SEQ ID NO 37
<211> LENGTH: 40
<212> TYPE: DNA
<213> ORGANISM: Homo sapiens

<400> SEQUENCE: 37
cgtttctttg ccctctgcag aggtgcctgt tgctcaagtc                           40

<210> SEQ ID NO 38
<211> LENGTH: 60
<212> TYPE: DNA
<213> ORGANISM: Homo sapiens

<400> SEQUENCE: 38
ttccaggaat gcgtggaaca ccagcatcgt gtcggtgctc tcctttccag tttcaaacag     60

<210> SEQ ID NO 39
<211> LENGTH: 40
<212> TYPE: DNA
<213> ORGANISM: Homo sapiens

<400> SEQUENCE: 39
gcgtggaaca ccagcatcgt gtcggtgctc tcctttccag                           40

<210> SEQ ID NO 40
<211> LENGTH: 60
<212> TYPE: DNA
<213> ORGANISM: Homo sapiens

<400> SEQUENCE: 40
ctgtcctctt ggtgctgtgg gtcctgaaag ttgtcgagtg cgcccgtccc tgtggtggga     60

<210> SEQ ID NO 41
<211> LENGTH: 40
<212> TYPE: DNA
<213> ORGANISM: Homo sapiens

<400> SEQUENCE: 41
ggtgctgtgg gtcctgaaag ttgtcgagtg cgcccgtccc                           40

<210> SEQ ID NO 42
<211> LENGTH: 1990
<212> TYPE: DNA
<213> ORGANISM: Homo sapiens
```

<400> SEQUENCE: 42

```
ccacccccccc cccccaccac caccaccacc accaccccgc cggccggccc caggcctcga    60
cgccctgggt cccttccggg gtggggcggg ctgtcccagg ggggctcacc gccattcatg   120
aaggggtgga gcctgcctgc ctgtgggcct ttacaagggc ggctggctgg ctggctggct   180
gtccgggcag gcctcctggc tgcacctgcc gcagtgcaca gtccggctga ggtgcacggg   240
agcccgccgg cctctctctg cccgcgtccg tccgtgaaat tccggccggg gctcaccgcg   300
atggccctcc cgacaccctc ggacagcacc ctccccgcgg aagcccgggg acgaggacgg   360
cgacggagac tcgtttggac cccgagccaa agcgaggccc tgcgagcctg ctttgagcgg   420
aacccgtacc cgggcatcgc caccagagaa cggctggccc aggccatcgg cattccggag   480
cccagggtcc agatttggtt tcagaatgag aggtcacgcc agctgaggca gcaccggcgg   540
gaatctcggc cctggcccgg gagacgcggc ccgccagaag gccggcgaaa gcggaccgcc   600
gtcaccggat cccagaccgc cctgctcctc cgagcctttg agaaggatcg ctttccaggc   660
atcgccgccc gggaggagct ggccagagag acgggcctcc cggagtccag gattcagatc   720
tggtttcaga atcgaagggc caggcacccg ggacagggtg gcagggcgcc cgcgcaggca   780
ggcggcctgt gcagcgcggc ccccggccgg ggtcaccctg ctccctcgtg ggtcgccttc   840
gcccacaccg gcgcgtgggg aacggggctt cccgcacccc acgtgccctg cgcgcctggg   900
gctctcccac aggggctttt cgtgagccag gcagcgaggg ccgccccgc gctgcagccc    960
agccaggccg cgccggcaga ggggggtctcc caacctgccc cggcgcgcgg ggatttcgcc  1020
tacgccgccc cggctcctcc ggacggggcg ctctcccacc ctcaggctcc tcggtggcct  1080
ccgcacccgg gcaaaagccg ggaggaccgg gacccgcagc gcgacggcct gccgggcccc  1140
tgcgcggtgg cacagcctgg gcccgctcaa gcggggccgc agggccaagg ggtgcttgcg  1200
ccacccacgt cccaggggag tccgtggtgg ggctggggcc ggggtcccca ggtcgccggg  1260
gcggcgtggg aaccccaagc cggggcagct ccacctcccc agcccgcgcc ccggacgcc   1320
tccgcctccg cgcggcaggg gcagatgcaa ggcatcccgg cgccctccca ggcgctccag  1380
gagccggcgc cctggtctgc actccctctgc ggcctgctgc tggatgagct cctggcgagc  1440
ccggagtttc tgcagcaggc gcaacctctc ctagaaacgg aggccccggg ggagctggag  1500
gcctcggaag aggccgcctc gctggaagca cccctcagcg aggaagaata ccgggctctg  1560
ctggaggagc tttaggacgc ggggttggga cggggtcggg tggttcgggg cagggccgtg  1620
gcctctcttt cgcggggaac acctggctgg ctacggaggg gcgtgtctcc gccccgcccc  1680
ctccaccggg ctgaccggcc tgggattcct gccttctagg tctaggcccg gtgagagact  1740
ccacaccgcg gagaactgcc attctttcct gggcatcccg gggatcccag agccggccca  1800
gacctgcgcg cagtgcgcac cccggctgac gtgcaaggga gctcgctggc ctctctgtgc  1860
ccttgttctt ccgtgaaatt ctggctgaat gtctccccc accttccgac gctgtctagg  1920
caaacctgga ttagagttac atctcctgga tgattagttc agagatatat taaaatgccc  1980
cctccctgtg                                                         1990
```

<210> SEQ ID NO 43
<211> LENGTH: 1854
<212> TYPE: DNA
<213> ORGANISM: Homo sapiens

<400> SEQUENCE: 43

```
ccacccccccc cccccaccac caccaccacc accccccgc cggccggccc caggcctcga    60
```

```
cgccctgggt cccttccggg gtggggcggg ctgtcccagg ggggctcacc gccattcatg    120
aaggggtgga gcctgcctgc ctgtgggcct ttacaagggc ggctggctgg ctggctggct    180
gtccgggcag gcctcctggc tgcacctgcc gcagtgcaca gtccggctga ggtgcacggg    240
agcccgccgg cctctctctg cccgcgtccg tccgtgaaat tccggccggg gctcaccgcg    300
atggccctcc cgacaccctc ggacagcacc ctccccgcgg aagcccgggg acgaggacgg    360
cgacggagac tcgtttggac cccgagccaa agcgaggccc tgcgagcctg ctttgagcgg    420
aacccgtacc cgggcatcgc caccagagaa cggctggccc aggccatcgg cattccggag    480
cccagggtcc agatttggtt tcagaatgag aggtcacgcc agctgaggca gcaccggcgg    540
gaatctcggc cctggcccgg gagacgcggc ccgccagaag gccggcgaaa gcggaccgcc    600
gtcaccggat cccagaccgc cctgctcctc cgagcctttg agaaggatcg ctttccaggc    660
atcgccgccc gggaggagct ggccagagag acgggcctcc cggagtccag gattcagatc    720
tggtttcaga atcgaagggc caggcacccg ggacagggtg gcaggcgcc cgcgcaggca    780 ggcggcctgt gcagcgcggc ccccggcggg ggtcaccctg ctccctcgtg ggtcgccttc    840
gcccacaccg gcgcgtgggg aacggggctt cccgcacccc acgtgccctg cgcgcctggg    900
gctctcccac aggggctttt cgtgagccag gcagcgaggg ccgccccgc gctgcagccc    960 agccaggccg cgccggcaga gggggtctcc caacctgccc cggcgcgcgg ggatttcgcc   1020
tacgccgccc cggctcctcc ggacggggcg ctctcccacc ctcaggctcc tcggtggcct   1080
ccgcacccgg gcaaaagccg ggaggaccgg gacccgcagc gcgacggcct gccgggcccc   1140
tgcgcggtgg cacagcctgg gcccgctcaa gcggggccgc agggccaagg ggtgcttgcg   1200
ccacccacgt cccaggggag tccgtggtgg ggctggggcc ggggtcccca ggtcgccggg   1260
gcggcgtggg aaccccaagc cggggcagct ccacctcccc agcccgcgcc cccggacgcc   1320
tccgcctccg cgcggcaggg gcagatgcaa ggcatcccgg cgccctccca ggcgctccag   1380
gagccggcgc cctggtctgc actcccctgc ggcctgctgc tggatgagct cctggcgagc   1440
ccggagtttc tgcagcaggc gcaacctctc ctagaaacgg aggcccccgg ggagctggag   1500
gcctcggaag aggccgcctc gctggaagca ccccctcagcg aggaagaata ccgggctctg   1560
ctggaggagc tttaggacgc ggggtctagg cccggtgaga gactccacac cgcggagaac   1620
tgccattctt tcctgggcat cccggggatc ccagagccgg cccagacctg cgcgcagtgc   1680 gcacccggc tgacgtgcaa gggagctcgc tggcctctct gtgcccttgt tcttccgtga   1740
aattctggct gaatgtctcc ccccaccttc cgacgctgtc taggcaaacc tggattagag   1800
ttacatctcc tggatgatta gttcagagat atattaaaat gccccctccc tgtg          1854
```

<210> SEQ ID NO 44
<211> LENGTH: 35
<212> TYPE: RNA
<213> ORGANISM: Homo sapiens

<400> SEQUENCE: 44
cgcggggaac accuggcugg cuacggaggg gcgug                                35

<210> SEQ ID NO 45
<211> LENGTH: 35
<212> TYPE: RNA
<213> ORGANISM: Homo sapiens

<400> SEQUENCE: 45

```
gccuucuagg ucuaggcccg gugagagacu ccaca                              35

<210> SEQ ID NO 46
<211> LENGTH: 35
<212> TYPE: RNA
<213> ORGANISM: Homo sapiens

<400> SEQUENCE: 46
uaggcaaacc uggauuagag uuacaucucc uggau                              35

<210> SEQ ID NO 47
<211> LENGTH: 19
<212> TYPE: RNA
<213> ORGANISM: Artificial
<220> FEATURE:
<223> OTHER INFORMATION: DUX4 RNA interference agent

<400> SEQUENCE: 47
acaccuggcu ggcuacgga                                                19

<210> SEQ ID NO 48
<211> LENGTH: 19
<212> TYPE: RNA
<213> ORGANISM: Artificial
<220> FEATURE:
<223> OTHER INFORMATION: DUX4 RNA interference agent

<400> SEQUENCE: 48
ggucuaggcc cggugagag                                                19

<210> SEQ ID NO 49
<211> LENGTH: 19
<212> TYPE: RNA
<213> ORGANISM: Artificial
<220> FEATURE:
<223> OTHER INFORMATION: DUX4 RNA interference agent

<400> SEQUENCE: 49
ccuggauuag aguuacauc                                                19

<210> SEQ ID NO 50
<211> LENGTH: 1714
<212> TYPE: DNA
<213> ORGANISM: Homo sapiens

<400> SEQUENCE: 50
ggagggcggg ctaccccggg accttgggcc ccgagctcat gcatgttcat aacgcggtgg    60
aggtggtagg tctttctaag ggcctcctgg ctgcacctgc cgcagtgcac aggccggctg   120
aggtgcacgg gagcccgccg gcctctctct gcccgcgtcc gtccgtgaaa ttccggccgg   180
ggctcaccgc gatggccctc ccgacacctt cggacagcac cctccccgcg gaagcccggg   240
gacgaggacg cgcgacggag actcgtttgg accccgagcca aagcgaggcc ctgcgagcct   300
gctttgagcg gaacccgtac ccgggcatcg ccaccagaga acggctggcc caggccatcg   360
gcattccgga gcccagggtc cagatttggt ttcagaatga gaggtcacgc cagctgaggc   420
agcaccggcg ggaatctcgg ccctggcccg ggagacgcgg cccgccagaa ggccggcgaa   480
agcggaccgc cgtcaccgga tcccagaccg ccctgctcct ccgagccttt gagaaggatc   540
gctttccagg catcgccgcc cgggaggagc tggccagaga cgggcctc ccggagtcca   600 ggattcagat ctggtttcag aatcgaaggg ccaggcaccc gggacagggt ggcagggcgc   660
ccgcgcaggc aggcggcctg tgcagcgcgg ccccggcgg gggtcaccct gctccctcgt   720
```

```
gggtcgcctt cgcccacacc ggcgcgtggg gaacggggct tcccgcaccc cacgtgccct      780
gcgcgcctgg ggctctccca caggggcctt tcgtgagcca ggcagcgagg gccgcccccg      840
cgctgcagcc cagccaggcc gcgccggcag aggggatctc ccaacctgcc ccggcgcgcg      900
gggatttcgc ctacgccgcc ccggctcctc cggacgggc  gctctcccac cctcaggctc      960
ctcggtggcc tccgcacccg ggcaaaagcc gggaggaccg ggaccccgcag cgcgacggcc     1020 tgccgggccc ctgcgcggtg gcacagcctg ggcccgctca gcggggccg  cagggccaag     1080 gggtgcttgc gccacccacg tcccagggga gtccgtggtg gggctggggc cggggtcccc     1140
aggtcgccgg ggcggcgtgg gaaccccaag ccggggcagc tccacctccc cagcccgcgc     1200
ccccggacgc ctccgcggca agcacagatg ccagccatcc aggcgcctcc caaccgctcc     1260
aggagccggg gcgctcgtct acagtcacct ccagcctgtt atatgagctc ctgtagacac     1320
cagagtttca gcaaaaggca cgacctttcc tagatccggc gccactgggg agctgaagg      1380 acgtggaaga gcccgctctg ctggaaccac tcctcagcca ggaagaacac cgggctctgc     1440
tggaggagca ggttggagcg gggttggggc ggggtggggg caggacggcg ccctctcttt     1500
cgcggtgaac ctctgactcg gtatggagag gcgtgccttc ccttccagct gacctgtcta     1560
ggatccctga gttccaggtc cggtgagaga ctccacacag aggagggctg tcattctttc     1620
ctgagcatcc cggggatccc agggcccgcc caggtaccgg gaggtggact gtctactgcg     1680
catgcgcagg tttgcaggca gcagcctagg tttt                                 1714

<210> SEQ ID NO 51
<211> LENGTH: 1903
<212> TYPE: DNA
<213> ORGANISM: Homo sapiens

<400> SEQUENCE: 51
ggagggcggg ctaccccggg accttgggcc ccgagctcat gcatgttcat aacgcggtgg       60
aggtggtagg tctttctaag ggcctcctgg ctgcacctgc cgcagtgcac aggccggctg      120
aggtgcacgg gagcccgccg gcctctctct gcccgcgtcc gtccgtgaaa ttccggccgg      180
ggctcaccgc gatggccctc ccgacacctt cggacagcac cctccccgcg gaagcccggg      240
gacgaggacg gcgacggaga ctcgtttgga ccccgagcca aagcgaggcc ctgcgagcct      300
gctttgagcg gaacccgtac ccgggcatcg ccaccagaga acggctggcc caggccatcg      360
gcattccgga gcccagggtc cagatttggt ttcagaatga gaggtcacgc cagctgaggc      420
agcaccggcg ggaatctcgg ccctggcccg ggagacgcgg cccgcagaa  ggccggcgaa      480 agcggaccgc cgtcaccgga tcccagaccg ccctgctcct ccgagccttt gagaaggatc      540
gctttccagg catcgccgcc cgggaggagc tggccagaga cgggcctc  ccggagtcca      600 ggattcagat ctggtttcag aatcgaaggg ccaggcaccc gggacagggt ggcagggcgc      660
ccgcgcaggc aggcggcctg tgcagcgcgg ccccgcgg  gggtcaccct gctccctcgt      720
gggtcgcctt cgcccacacc ggcgcgtggg gaacggggct tcccgcaccc cacgtgccct      780
gcgcgcctgg ggctctccca caggggcctt tcgtgagcca ggcagcgagg gccgcccccg      840
cgctgcagcc cagccaggcc gcgccggcag aggggatctc ccaacctgcc ccggcgcgcg      900
gggatttcgc ctacgccgcc ccggctcctc cggacgggc  gctctcccac cctcaggctc      960
ctcggtggcc tccgcacccg ggcaaaagcc gggaggaccg ggaccccgcag cgcgacggcc    1020 tgccgggccc ctgcgcggtg gcacagcctg ggcccgctca gcggggccg  cagggccaag    1080
```

```
gggtgcttgc gccacccacg tcccagggga gtccgtggtg gggctggggc cggggtcccc    1140
aggtcgccgg ggcggcgtgg gaaccccaag ccggggcagc tccacctccc cagcccgcgc    1200
ccccggacgc tccgcggca agcacagatg ccagccatcc aggcgcctcc caaccgctcc     1260
aggagccggg gcgctcgtct acagtcacct ccagcctgtt atatgagctc ctgtagacac    1320
cagagtttca gcaaaaggca cgacctttcc tagatccggc gccactgggg gagctgaagg    1380
acgtggaaga gcccgctctg ctggaaccac tcctcagcca ggaagaacac cgggctctgc    1440
tggaggagca ggttggagcg gggttggggc ggggtggggg caggacggcg ccctctcttt    1500
cgcggtgaac ctctgactcg gtatggagag gcgtgccttc ccttccagct gacctgtcta    1560
ggatccctga gttccaggtc cggtgagaga ctccacacag aggagggctg tcattctttc    1620
ctgagcatcc cggggatccc agggcccgcc caggtaccgg gaggtggact gtctactgcg    1680
catgcgcagg tttgcaggca gcagcctagg ttttccaacc agcccaggcg gagctctcat    1740
tcctttttcc ccagcgttct tcagtcgagt tggcggagac ctcagtccgc gaagcgctgg    1800
gccggggcag aagccaggcc agttctcctt tccgtggctc gactcctctg cctcttcgct    1860
caccaacact tgccaacccc cgtcccgcca gcctcctcgc cag                     1903

<210> SEQ ID NO 52
<211> LENGTH: 2409
<212> TYPE: DNA
<213> ORGANISM: Homo sapiens

<400> SEQUENCE: 52
atgtcttatc gtcacttccg tgtcatccta tccctgacct ccccacagcc cacagctctt      60
gtcataggcc agcgggacct cgcactccgg gaaaacgtgg ggtgcccggt gcaggccgag     120
agctcggccc acagccgcgt ctgcttgcgg ggcgcccacc agctcaccag ccctccggat     180
cgccggcccg ggggacctgt tgctcgcgtg tctcccgccc ccgaaagcgc gaccacgttg     240
gctgtttccc gagctctgcg gggacacaga aacctccagc gaagcgtgga aaagcagcat     300
cgtgacttcg ctctcctttc cggtttccag accggccaca gtggagactc cccttgttgc     360
aggaaacagg aatccgtggt caggccaatt actggagaac ctcagagagc cagccccgga     420
agcccctctt tcccctccaa tccggccctg cacccaccca cccacaagg ccctggtccc      480 tgtggttttc ggcttcggag gcgggctac cccgggacct tgggccccga gctcatgcat      540
gttcataacg cggtggaggt ggtaggtctt tctaagggcc tcctggctgc acctgccgca     600
gtgcacaggc cggctgaggt gcacgggagc ccgccggcct ctctctgccc gcgtccgtcc     660
gtgaaattcc ggccggggct caccgcgatg gccctcccga cacctcggac agcacccctc     720
cccgcggaag cccggggacg aggacggcga cggagactcg tttggacccc gagccaaagc     780
gaggccctgc gagcctgctt tgagcggaac ccgtacccgg gcatcgccac cagagaacgg     840
ctggcccagg ccatcggcat tccggagccc agggtccaga tttggtttca gaatgagagg     900
tcacgccagc tgaggcagca ccggcgggaa tctcggcccct ggcccgggag acgcggcccg    960
ccagaaggcc ggcgaaagcg gaccgccgtc accggatccc agaccgccct gctcctccga    1020
gcctttgaga aggatcgctt tccaggcatc gccgccggg aggagctggc cagagagacg     1080
ggcctcccgg agtccaggat tcagatctgg tttcagaatc gaagggccag gcacccggga    1140
cagggtggca gggcgcccgc gcaggcaggc ggcctgtgca gcgcggcccc tggcgggggt    1200 cacccctgctc cctcgtgggt cgccttcgcc cacaccggcg cgtggggaac ggggcttccc    1260
gcaccccacg tgccctgcgc gcctggggct ctcccacagg gggctttcgt gagccaggca    1320
```

```
gcgagggccg cccccgcgct gcagcccagc caggccgcgc cggcagaggg ggtctcccaa    1380
cctgccccgg cgcgcgggga tttcgcctac gccgccccgg ctcctccgga cggggcgctc    1440
tcccaccctc aggctcctcg gtggcctccg cacccgggca aaagccggga ggaccgggac    1500
gcgcagcgcg acggcctgcc gggccctgc gcggtggcac agcctgggcc cgctcaagcg    1560
gggccgcagg gccaagggt gcttgcgcca cccacgtccc aggggagtcc gtggtggggc    1620
tggggccggg gtccccaggt cgccggggcg gcgtgggaac cccaagccgg ggcagctcca    1680
cctccccagc ccgcgccccc ggacgcctcc gcggcaagca cagatgccag ccatccaggc    1740
gcctcccaac cgctccagga gccggggcgc tcgtctacag tcacctccag cctgttatat    1800
gagctcctgt agacaccaga gtttcagcaa aaggcacgac cttttcctaga tccggcgcca    1860 ctggggagc tgaaggacgt ggaagagccc gctctgctgg aaccactcct cagccaggaa    1920
gaacaccggg ctctgctgga ggagcagagg tgcctgttgc tcaagtctct gccccgccc    1980 cccgaaagtg tgaccatgtt gactgtttgt ttcccgagct ctgtggggac ccagaaactt    2040
ccaggaatgc gtggaacacc agcatcgttt gtcgagtgcg cccgtccctg tggtgggagc    2100
agtggccccg agcgtgccca cgggcccgg cttgggtttc tctcgtgttt agaatggtat    2160
ggccgtagac aatggcggtg gcgcctggct ggtccaagag cccggtccag ctacgcgcgt    2220
ctgattccag gcgtcaccac caacccgggg ccgcgaggct gggatcaggc accccggag    2280 ccgctcgccc gcggccgggc tgctctcccc ctctatacgc ccaagcacca gtcgccgcgc    2340
tgcgttttcc gccggcctcg cagagcgtcc cgctatcgcc ggcggccaga ccacgcgcag    2400
gaccgctga                                                           2409

<210> SEQ ID NO 53
<211> LENGTH: 35
<212> TYPE: RNA
<213> ORGANISM: Homo sapiens

<400> SEQUENCE: 53
uguagacacc agaguuucag caaaaggcac gaccu                               35

<210> SEQ ID NO 54
<211> LENGTH: 35
<212> TYPE: RNA
<213> ORGANISM: Homo sapiens

<400> SEQUENCE: 54
cacacagagg agggcuguca uucuuuccug agcau                               35

<210> SEQ ID NO 55
<211> LENGTH: 35
<212> TYPE: RNA
<213> ORGANISM: Homo sapiens

<400> SEQUENCE: 55
uuuccccagc guucuucagu cgaguuggcg gagac                               35

<210> SEQ ID NO 56
<211> LENGTH: 19
<212> TYPE: RNA
<213> ORGANISM: Artificial
<220> FEATURE:
<223> OTHER INFORMATION: DUX4c RNA interference agent

<400> SEQUENCE: 56
```

```
ccagaguuuc agcaaaagg                                              19
```

```
<210> SEQ ID NO 57
<211> LENGTH: 19
<212> TYPE: RNA
<213> ORGANISM: Artificial
<220> FEATURE:
<223> OTHER INFORMATION: DUX4c RNA interference agent

<400> SEQUENCE: 57
ggagggcugu cauucuuuc                                              19

<210> SEQ ID NO 58
<211> LENGTH: 19
<212> TYPE: RNA
<213> ORGANISM: Artificial
<220> FEATURE:
<223> OTHER INFORMATION: DUX4c RNA interference agent

<400> SEQUENCE: 58
gcguucuuca gucgaguug                                              19

<210> SEQ ID NO 59
<211> LENGTH: 485
<212> TYPE: PRT
<213> ORGANISM: Homo sapiens

<400> SEQUENCE: 59
```

```
Met Lys Gly Trp Ser Leu Pro Ala Cys Gly Pro Leu Gln Gly Arg Leu
1               5                   10                  15

Ala Gly Trp Leu Ala Val Arg Ala Gly Leu Leu Ala Ala Pro Ala Ala
            20                  25                  30

Val His Ser Pro Ala Glu Val His Gly Ser Pro Pro Ala Ser Leu Cys
        35                  40                  45

Pro Arg Pro Ser Val Lys Phe Arg Pro Gly Leu Thr Ala Met Ala Leu
    50                  55                  60

Pro Thr Pro Ser Asp Ser Thr Leu Pro Ala Glu Ala Arg Gly Arg Gly
65                  70                  75                  80

Arg Arg Arg Arg Leu Val Trp Thr Pro Ser Gln Ser Glu Ala Leu Arg
                85                  90                  95

Ala Cys Phe Glu Arg Asn Pro Tyr Pro Gly Ile Ala Thr Arg Glu Arg
            100                 105                 110

Leu Ala Gln Ala Ile Gly Ile Pro Glu Pro Arg Val Gln Ile Trp Phe
        115                 120                 125

Gln Asn Glu Arg Ser Arg Gln Leu Arg Gln His Arg Arg Glu Ser Arg
    130                 135                 140

Pro Trp Pro Gly Arg Arg Gly Pro Pro Glu Gly Arg Arg Lys Arg Thr
145                 150                 155                 160

Ala Val Thr Gly Ser Gln Thr Ala Leu Leu Leu Arg Ala Phe Glu Lys
                165                 170                 175

Asp Arg Phe Pro Gly Ile Ala Ala Arg Glu Glu Leu Ala Arg Glu Thr
            180                 185                 190

Gly Leu Pro Glu Ser Arg Ile Gln Ile Trp Phe Gln Asn Arg Arg Ala
        195                 200                 205

Arg His Pro Gly Gln Gly Gly Arg Ala Pro Ala Gln Ala Gly Gly Leu
    210                 215                 220

Cys Ser Ala Ala Pro Gly Gly Gly His Pro Ala Pro Ser Trp Val Ala
225                 230                 235                 240
```

Phe Ala His Thr Gly Ala Trp Gly Thr Gly Leu Pro Ala Pro His Val
            245                 250                 255

Pro Cys Ala Pro Gly Ala Leu Pro Gln Gly Ala Phe Val Ser Gln Ala
        260                 265                 270

Ala Arg Ala Ala Pro Ala Leu Gln Pro Ser Gln Ala Ala Pro Ala Glu
    275                 280                 285

Gly Val Ser Gln Pro Ala Pro Ala Arg Gly Asp Phe Ala Tyr Ala Ala
290                 295                 300

Pro Ala Pro Pro Asp Gly Ala Leu Ser His Pro Gln Ala Pro Arg Trp
305                 310                 315                 320

Pro Pro His Pro Gly Lys Ser Arg Glu Asp Arg Asp Pro Gln Arg Asp
                325                 330                 335

Gly Leu Pro Gly Pro Cys Ala Val Ala Gln Pro Gly Pro Ala Gln Ala
            340                 345                 350

Gly Pro Gln Gly Gln Gly Val Leu Ala Pro Pro Thr Ser Gln Gly Ser
        355                 360                 365

Pro Trp Trp Gly Trp Gly Arg Gly Pro Gln Val Ala Gly Ala Ala Trp
    370                 375                 380

Glu Pro Gln Ala Gly Ala Ala Pro Pro Gln Pro Ala Pro Pro Asp
385                 390                 395                 400

Ala Ser Ala Ser Ala Arg Gln Gly Gln Met Gln Gly Ile Pro Ala Pro
                405                 410                 415

Ser Gln Ala Leu Gln Glu Pro Ala Pro Trp Ser Ala Leu Pro Cys Gly
            420                 425                 430

Leu Leu Leu Asp Glu Leu Leu Ala Ser Pro Glu Phe Leu Gln Gln Ala
        435                 440                 445

Gln Pro Leu Leu Glu Thr Glu Ala Pro Gly Glu Leu Glu Ala Ser Glu
    450                 455                 460

Glu Ala Ala Ser Leu Glu Ala Pro Leu Ser Glu Glu Tyr Arg Ala
465                 470                 475                 480

Leu Leu Glu Glu Leu
            485

<210> SEQ ID NO 60
<211> LENGTH: 374
<212> TYPE: PRT
<213> ORGANISM: Homo sapiens

<400> SEQUENCE: 60

Met Ala Leu Pro Thr Pro Ser Asp Ser Thr Leu Pro Ala Glu Ala Arg
1               5                   10                  15

Gly Arg Gly Arg Arg Arg Leu Val Trp Thr Pro Ser Gln Ser Glu
            20                  25                  30

Ala Leu Arg Ala Cys Phe Glu Arg Asn Pro Tyr Pro Gly Ile Ala Thr
        35                  40                  45

Arg Glu Arg Leu Ala Gln Ala Ile Gly Ile Pro Glu Pro Arg Val Gln
    50                  55                  60

Ile Trp Phe Gln Asn Glu Arg Ser Arg Gln Leu Arg Gln His Arg Arg
65                  70                  75                  80

Glu Ser Arg Pro Trp Pro Gly Arg Gly Pro Pro Glu Gly Arg Arg
                85                  90                  95

Lys Arg Thr Ala Val Thr Gly Ser Gln Thr Ala Leu Leu Leu Arg Ala
            100                 105                 110

Phe Glu Lys Asp Arg Phe Pro Gly Ile Ala Ala Arg Glu Glu Leu Ala
        115                 120                 125

```
Arg Glu Thr Gly Leu Pro Glu Ser Arg Ile Gln Ile Trp Phe Gln Asn
    130                 135                 140

Arg Arg Ala Arg His Pro Gly Gln Gly Gly Arg Ala Pro Ala Gln Ala
145                 150                 155                 160

Gly Gly Leu Cys Ser Ala Ala Pro Gly Gly His Pro Ala Pro Ser
                165                 170                 175

Trp Val Ala Phe Ala His Thr Gly Ala Trp Thr Gly Leu Pro Ala
                180                 185                 190

Pro His Val Pro Cys Ala Pro Gly Ala Leu Pro Gln Gly Ala Phe Val
            195                 200                 205

Ser Gln Ala Ala Arg Ala Pro Ala Leu Gln Pro Ser Gln Ala Ala
    210                 215                 220

Pro Ala Glu Gly Ile Ser Gln Pro Ala Pro Ala Arg Gly Asp Phe Ala
225                 230                 235                 240

Tyr Ala Ala Pro Ala Pro Pro Asp Gly Ala Leu Ser His Pro Gln Ala
                245                 250                 255

Pro Arg Trp Pro Pro His Pro Gly Lys Ser Arg Glu Asp Arg Asp Pro
                260                 265                 270

Gln Arg Asp Gly Leu Pro Gly Pro Cys Ala Val Ala Gln Pro Gly Pro
    275                 280                 285

Ala Gln Ala Gly Pro Gln Gly Gln Gly Val Leu Ala Pro Pro Thr Ser
    290                 295                 300

Gln Gly Ser Pro Trp Trp Gly Trp Gly Arg Gly Pro Gln Val Ala Gly
305                 310                 315                 320

Ala Ala Trp Glu Pro Gln Ala Gly Ala Ala Pro Pro Gln Pro Ala
                325                 330                 335

Pro Pro Asp Ala Ser Ala Ala Ser Thr Asp Ala Ser His Pro Gly Ala
                340                 345                 350

Ser Gln Pro Leu Gln Glu Pro Gly Arg Ser Ser Thr Val Thr Ser Ser
    355                 360                 365

Leu Leu Tyr Glu Leu Leu
    370
```

<210> SEQ ID NO 61
<211> LENGTH: 1800
<212> TYPE: DNA
<213> ORGANISM: Homo sapiens

<400> SEQUENCE: 61

```
ctctgctgga ggagctttag gacgcggggt tgggacgggg tcgggtggtt cggggcaggg    60
ccgtggcctc tctttcgcgg ggaacacctg gctggctacg gaggggcgtg tctccgcccc   120
gcccctcca  ccgggctgac cggcctggga ttcctgcctt ctaggtctag gcccggtgag   180
agactccaca ccgcggagaa ctgccattct ttcctgggca tcccgggat  cccagagccg   240
gcccaggtac cagcaggtgg gccgcctact gcgcacgcgc gggtttgcgg gcagccgcct   300
gggctgtggg agcagcccgg gcagagctct cctgcctctc caccagccca ccccgccgcc   360
tgaccgcccc ctccccaccc cccaccccccc acccccggaa aacgcgtcgt ccctgggct   420
gggtggagac ccccgtcccg cgaaacaccg gccccgcgc  agcgtccggg cctgacaccg   480
ctccggcggc tcgcctccta tgcgccccg  cgccaccgtc gcccgccgc  ccgggcccct   540
gcagccgccc aggtgccagc acggagcgcc tggcggcgga acgcagaccc caggcccggc   600
gcacaccggg gacgctgagc gttccaggcg ggagggaagg cgggcagaga tggagagagg   660
```

| | |
|---|---|
| aacgggagac ctagaggggc ggaaggacgg gcggagggac gttaggaggg agggagggag | 720 |
| gcagggaggc agggaggaac ggagggaaag acagagcgac gcaggactg ggggcgggcg | 780 |
| ggagggagcc ggggaacggg gggaggaagg cagggaggaa aagcggtcct cggcctccgg | 840 |
| gagtagcggg accccgccc tccgggaaaa cggtcagcgt ccggcgcggg ctgagggctg | 900 |
| ggcccacagc cgccgcgccg gccggcgggg caccacccat tcgccccggt tccgtggccc | 960 |
| agggagtggg cggtttcctc cgggacaaaa gaccgggact cgggttgccg tcgggtcttc | 1020 |
| acccgcgcgg ttcacagacc gcacatcccc aggctgagcc ctgcaacgcg gcgcgaggcc | 1080 |
| gacagccccg gccacggagg agccacacgc aggacgacgg aggcgtgatt ttggtttccg | 1140 |
| cgtggctttg ccctccgcaa ggcggcctgt tgctcacgtc tctccggccc ccgaaaggct | 1200 |
| ggccatgccg actgtttgct cccggagctc tgcgggcacc cggaaacatg cagggaaggg | 1260 |
| tgcaagcccg gcacggtgcc ttcgctctcc ttgccaggtt ccaaaccggc cacactgcag | 1320 |
| actcccacg ttgccgcacg cgggaatcca tcgtcaggcc atcacgccgg ggaggcatct | 1380 |
| cctctctggg gtctcgctct ggtcttctac gtggaaatga acgagagcca cacgcctgcg | 1440 |
| tgtgcgagac cgtcccggca acggcgacgc ccacaggcat tgcctccttc acggagagag | 1500 |
| ggcctggcac actcaagact cccacggagg ttcagttcca cactcccctc caccctccca | 1560 |
| ggctggtttc tccctgctgc cgacgcgtgg gagcccagag agcggcttcc cgttcccgcg | 1620 |
| ggatccctgg agaggtccgg agagccgcc ccgaaacgc gccccctcc ccctcccc | 1680 |
| ctctcccct tcctcttcgt ctctccggcc ccaccaccac caccgccacc acgccctccc | 1740 |
| ccccccccc cccccccac caccaccacc accacccgc cggccggccc caggcctcga | 1800 |

<210> SEQ ID NO 62
<211> LENGTH: 1229
<212> TYPE: DNA
<213> ORGANISM: Homo sapiens

<400> SEQUENCE: 62

| | |
|---|---|
| ctctgctgga ggagctttag gacgcggggt tgggacgggg tcgggtggtt cggggcaggg | 60 |
| ccgtggcctc tctttcgcgg ggaacacctg gctggctacg gaggggcgtg tctccgcccc | 120 |
| gccccctcca ccgggctgac cggcctggga ttcctgcctt ctaggtctag gcccggtgag | 180 |
| agactccaca ccgcggagaa ctgccattct ttcctgggca tcccggggat cccagagccg | 240 |
| gcccaggtac ctgcgcacgc gcgggttgc gggcagccgc ctgggctgtg ggagcagccc | 300 |
| gggcagagct ctcctgcctc tccaccagcc caccccgccg cctgaccgcc cctccccac | 360 |
| ccccaccc ccaccccgg aaaacgcgtc gtccctggg ctgggtggag accccgtcc | 420 |
| cgcgaaacac cgggccccgc gcagcgtccg ggcctgactc cgctccggcg gctcgcctcc | 480 |
| tgtgtgcccc cgcgccaccg tcgcccgccc gcccgggccc ctgcagcctc ccagctgcca | 540 |
| gcgcggagct cctggcggtc aaaagcatac ctctgtctgt cttgcccgc ttcctggcta | 600 |
| gacctgcgcg cagtgcgcac cccggctgac gtgcaaggga gctcgctggc ctctctgtgc | 660 |
| ccttgttctt ccgtgaaatt ctggctgaat gtctccccc accttccgac gctgtctagg | 720 |
| caaacctgga ttagagttac atctcctgga tgattagttc agagatatat taaaatgccc | 780 |
| cctccctgtg gatcctatag aagatttgca tcttttgtgt gatgagtgca gagatatgtc | 840 |
| acaatatccc ctgtagaaaa agcctgaaat tggtttacat aacttcggtg atcagtgcag | 900 |
| atgtgtttca gaactccata gtagactgaa cctagagaat ggttacatca cttaggtgat | 960 |
| cagtgtagag atatgttaaa attctcgtgt agacagagcc tagacaattg ttacatcacc | 1020 |

| tagtgatcag tgcagggata agtcataaag cctcctgtag gcagagtgta ggcaagtgtt | 1080 |
| cccctccctgg gctgatcagt gcagagatat ctcacaaagc ccctataagc caaaccttga | 1140 |
| caagggttac atcacctgtt tgagcagtgg aaatatatat cacaaagccc cctgtagaca | 1200 |
| aagcccagac aattttaca tctcctgag | 1229 |

<210> SEQ ID NO 63
<211> LENGTH: 1246
<212> TYPE: DNA
<213> ORGANISM: Homo sapiens

<400> SEQUENCE: 63

| ctctgctgga ggagctttag gacgcggggt tgggacgggg tcgggtggtt cggggcaggg | 60 |
| ccgtggcctc tctttcgcgg ggaacacctg gctggctacg gaggggcgtg tctccgcccc | 120 |
| gcccccctcca ccgggctgac cggcctggga ttcctgcctt ctaggtctag gcccggtgag | 180 |
| agactccaca ccgcggagaa ctgccattct ttcctgggca tcccggggat cccagagccg | 240 |
| gcccaggtac cagcaggtgg gccgcctact gcgcacgcgc gggtttgcgg gcagccgcct | 300 |
| gggctgtggg agcagcccgg gcagagctct cctgcctctc caccagccca ccccgccgcc | 360 |
| tgaccgcccc ctccccaccc ccaccccccca cccccggaaa acgcgtcgtc ccctgggctg | 420 |
| ggtggagacc cccgtcccgc gaaacaccgg gccccgcgca gcgtccgggc ctgacaccgc | 480 |
| tccggcggct cgcctcctct gcgcccccgc gccaccgtcg cccgcccgcc cgggcccctg | 540 |
| cagcctccca gctgccagcg cggagctcct ggcggtcaaa agcataccctc tgtctgtctt | 600 |
| tgcccgcttc ctggctagac ctgcgcgcag tgcgcacccc ggctgacgtg caagggagct | 660 |
| cgctggcctc tctgtgccct tgttcttccg tgaaattctg gctgaatgtc tcccccccacc | 720 |
| ttccgacgct gtctaggcaa acctggatta gagttacatc tcctggatga ttagttcaga | 780 |
| gatatattaa aatgcccccct ccctgtggat cctatagaag atttgcatct tttgtgtgat | 840 |
| gagtgcagag atatgtcaca atatcccctg tagaaaaagc ctgaaattgg tttacataac | 900 |
| ttcggtgatc agtgcagatg tgtttcagaa ctccatagta gactgaacct agagaatggt | 960 |
| tacatcactt aggtgatcag tgtagagata tgttaaaatt ctcgtgtaga cagagcctag | 1020 |
| acaattgtta catcacctag tgatcagtgc agggataagt cataaagcct cctgtaggca | 1080 |
| gagtgtaggc aagtgttccc tccctgggct gatcagtgca gagatatctc acaaagcccc | 1140 |
| tataagccaa accttgacaa gggttacatc acctgtttga gcagtggaaa tatatatcac | 1200 |
| aaagccccct gtagacaaag cccagacaat ttttacatct cctgag | 1246 |

<210> SEQ ID NO 64
<211> LENGTH: 25
<212> TYPE: RNA
<213> ORGANISM: Artificial
<220> FEATURE:
<223> OTHER INFORMATION: DUX4 antisense agent

<400> SEQUENCE: 64

| acccgacccc gucccaaccc cgcgu | 25 |

<210> SEQ ID NO 65
<211> LENGTH: 25
<212> TYPE: RNA
<213> ORGANISM: Artificial
<220> FEATURE:
<223> OTHER INFORMATION: DUX4 antisense agent

```
<400> SEQUENCE: 65
gggcauuuua auauaucucu gaacu                                          25

<210> SEQ ID NO 66
<211> LENGTH: 25
<212> TYPE: DNA
<213> ORGANISM: Homo sapiens

<400> SEQUENCE: 66
acgcggggtt gggacggggt cgggt                                          25

<210> SEQ ID NO 67
<211> LENGTH: 66
<212> TYPE: DNA
<213> ORGANISM: Homo sapiens

<400> SEQUENCE: 67
acatctcctg gatgattagt tcagagatat attaaaatgc cccctccctg tggatcctat    60
agaaga                                                               66

<210> SEQ ID NO 68
<211> LENGTH: 46
<212> TYPE: DNA
<213> ORGANISM: Homo sapiens

<400> SEQUENCE: 68
gatgattagt tcagagatat attaaaatgc cccctccctg tggatc                   46

<210> SEQ ID NO 69
<211> LENGTH: 25
<212> TYPE: DNA
<213> ORGANISM: Homo sapiens

<400> SEQUENCE: 69
agttcagaga tatattaaaa tgccc                                          25
```